(12) United States Patent
Saltzman et al.

(10) Patent No.: US 10,765,638 B2
(45) Date of Patent: Sep. 8, 2020

(54) PARTICLE FORMULATION WITH POLYCATION COMPLEX

(71) Applicant: Yale University, New Haven, CT (US)

(72) Inventors: W. Mark Saltzman, New Haven, CT (US); Joseph Contessa, Guilford, CT (US); Amanda King, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/179,605

(22) Filed: Nov. 2, 2018

(65) Prior Publication Data

US 2019/0133962 A1 May 9, 2019

Related U.S. Application Data

(60) Provisional application No. 62/581,311, filed on Nov. 3, 2017.

(51) Int. Cl.
*A61K 47/69* (2017.01)
*A61K 9/51* (2006.01)
(Continued)

(52) U.S. Cl.
CPC .......... *A61K 9/5146* (2013.01); *A61K 9/5153* (2013.01); *A61K 31/506* (2013.01);
(Continued)

(58) Field of Classification Search
None
See application file for complete search history.

(56) References Cited

U.S. PATENT DOCUMENTS 6,254,890 B1 7/2001 Hirosue
6,265,389 B1 7/2001 Burke
(Continued)

FOREIGN PATENT DOCUMENTS

WO 03087384 10/2003
WO 2006023491 3/2006
(Continued)

OTHER PUBLICATIONS

Xiao et al. Recent advances in PEG-PLA block copolymers nanoparticles, International Journal of Nanomedicine, 2010:5 1057-1065). (Year: 2010).*
(Continued)

*Primary Examiner* — Robert A Wax
*Assistant Examiner* — Melissa S Mercier
(74) *Attorney, Agent, or Firm* — Pabst Patent Group LLP

(57) ABSTRACT

Compositions and methods for efficient delivery of therapeutic agents in vivo are provided. Typically, the compositions are in the form of polymeric particles formed from one or more therapeutic agent complexed with a polycationic polymer which is further encapsulated in one or more amphiphilic polymers, preferably diblock copolymer of a polyalkylene oxide and a polyester such as poly(D,L-lactide)-poly(ethylene glycol) (PLA-PEG). In the preferred embodiments, the chemotherapeutic agent reduces, or inhibits N-glycosylation of one or more receptor tyrosine kinases of cancer cells. Methods of using the particles to treat cancer are also provided.

22 Claims, 14 Drawing Sheets

Specification includes a Sequence Listing.

(51) Int. Cl.
　　　A61K 31/506　　(2006.01)
　　　A61P 35/00　　(2006.01)
　　　A61K 45/06　　(2006.01)
　　　A61K 31/635　　(2006.01)
　　　A61K 47/59　　(2017.01)
(52) U.S. Cl.
　　　CPC ............ *A61K 31/635* (2013.01); *A61K 45/06* (2013.01); *A61K 47/59* (2017.08); *A61K 47/6935* (2017.08); *A61K 47/6937* (2017.08); *A61P 35/00* (2018.01)

(56) References Cited

U.S. PATENT DOCUMENTS

| | | | |
|---|---|---|---|
| 6,509,323 | B1 | 1/2003 | Davis |
| 6,770,740 | B1 | 8/2004 | Rice |
| 9,241,898 | B2 | 1/2016 | Saltzman |
| 9,822,364 | B2 | 11/2017 | Saltzman |
| 2002/0012652 | A1 | 1/2002 | Levy |
| 2006/0084617 | A1 | 4/2006 | Satishchandran |
| 2006/0205635 | A1 | 9/2006 | Corey |
| 2009/0011004 | A1 | 1/2009 | Lutz |
| 2010/0022680 | A1 | 1/2010 | Karnik |
| 2017/0042819 | A1* | 2/2017 | Goomer ............... A61K 9/107 |
| 2019/0000858 | A1 | 1/2019 | Contessa |

FOREIGN PATENT DOCUMENTS

| | | |
|---|---|---|
| WO | 2006133099 | 12/2006 |
| WO | 2009114614 | 9/2009 |
| WO | 2017/019540 | 2/2017 |
| WO | 2017019540 | 2/2017 |

OTHER PUBLICATIONS

Xiao et al. (Recent advances in PEG-PLA block copolymer nanoparticles, International Journal of Nanomedicine, 2010:2 1057-1065. (Year: 2010).*

Aebi, et al., "N-Linked protein glycosylation in the ER", Biochem. Et Bipohys. Acta. (BBA)—Molecular Cell Research, 1833(11):2430-2437 (2013).

Almiron Bonnin, et al., "Insulin mediated signaling facilitates resistance to PDGFR inhibition in Proneural hPDGFB-Drivel gliomas", Mol. Cancer. Ther., 16:705-716 (2017).

Baro, et al., "Oligosaccharyltransferase inhibition Reduces Receptor Tyrosine Kinase Activation and Enhances Glioma Radiosensitivity", Clin. Cancer Res., (2018).

Begg, et al., "Strategies to improve radiotherapy with targeted drugs", Nat. Rev. Cancer, 11:239-253 (2011).

Blakely, et al., "Evolution and clinical impact of co-occuring genetic alterations in advanced stage EGFR-mutant lung cancers", Nat. Genet., 49(12):1693-1704 (2017).

Brennan, et al., "The somatic genomic landscape of glioblastoma", Cell, 155(2):462-477 (2013).

Byers, et al., "An epithelial-mesenchymal transition (EMT) gene signature predicts resistance to EGFR and PI3K inhibitors and identifies Axl as a therapeutic target for overcoming EGFR inhibitor resistance", Clin Cancer Res., 19(1):279-290 (2013).

Cancer Genome Atlas Research N., "Comprehensive genomic characterization defines human glioblastoma genes and core pathways", Nature, 455:1061-1068 (2008).

Cazet, et al., "Mannose phosphate isomerase regulates fibroblast growth factor receptor family signaling and glioma radiosensitivity", PLoS One, 9:e110345 (2014).

Chakravarti, et al., "RTOG 0211: a phase 1/2 study of radiation therapy with concurrent gefitinib for newly diagnosed glioblastoma patients", Int. J. Radiat. Oncol. Biol. Phys., 85(5):1206-1211 (2013).

Chen, et al., "The epidermal growth factor receptor: a role in repair of radiation-induced DNA damage", Clin. Cancer Res., 13(22 pt.1):6555-6560 (2007).

Chinot, et al., "Bevacizumab plus radiotherapy-temozolomide for newly diagnosed glioblastoma", N Engl. J. Med., 370(8):709-722 (2014).

Chong, et al., "The quest to overcome resistance to EGFR-targeted therapies in cancer", Nat Med., 19(11):1389-1400 (2013).

Contessa, et al., "Molecular imaging of N-Linked glycosylation suggests glycan biosynthesis is a novel target for cancer therapy", Clin. Cancer Res., 16(12):3205-3214 (2010).

Contessa, et al., "Inhibition of N-linked glycosylation disrupts receptor tyrosine kinase signaling in tumor cells", Cancer Res., 68:3803-3809 (2008).

Croci, et al., "Glycosylation-dependent lectin-receptor interactions preserve angiogenesis in anti-VEGF refractory tumors", Cell, 156:744-758 (2014).

Dawson, et. al., "Molecular dynamics simulations of transitions for ECD epidermal growth factor receptors show key differences between human and drosophila forms of the receptors", Structure, 15:942-954 (2007).

De Bacco, et al., "Induction of MET by ionizing radiation and its role in radioresistance and invasive growth of cancer" J. Natl. Cancer Inst., 103:645-661 (2011).

De Mello, et. al., "Epidermal growth factor receptor and K-Ras in non-small cell lung cancer-molecular pathways involved and targeted therapies", World J Clin Oncol., 2(11):367-376 (2011).

Engleman, et al., "MET amplification leads to getfirinib resistance in lung cancer by activationg ERBB3 signaling", Science, 316(5827):1039-1043 (2007).

Franceschi, et al., "EORTC 26083 phase I/II trail of dasatinib in communication with CCNU in patients with recurrent glioblastoma", Neuro Oncol., 14(12):1503-1510 (2012).

Freeze, et al., "Genetic defects in the human glycome", Nat. Rev. Genet., 7:537-551 (2006).

Gemmill, et al., "The neuropilin 2 isoform NRP2b uniquely supports TGFβ-mediated progression in lung cancer", Sci Signal, 10(462) (2017).

Gordon, "Amyotrophic Lateral Sclerosis: An update for 2013 Clinical Features, Pathophysiology, Management and Therapeutic Trials", Aging and Disease, 4(5):295-310 (2013).

Gouaze-Anderson, et al., "FGFR1 Induces Glioblastoma Radioresistance through the PLCy/Hif1a Pathway", Cancer Res., 76:3036-3044 (2016).

Hafirassou, et al., "A global interactome map of the dengue virus NS1 Identifies virus restriction and dependency host factors", Cell Rep., 21(13):3900-3913 (2017).

Hata, et al., "Tumor cells can follow distinct evolutionary paths to become resistant to epidermal growth factor receptor inhibition", Nat Med, 22(3):262-269 (2016).

Huang, et al., "c-Met-mediated endothelial plasticity drives aberrant vascularization and chemoresistance in glioblastoma", J Clin Invest., 126:1801-1814 (2016).

Itkonen, et al., "N-linked glycosylation supports cross-talk between receptor tyrosine kinases and androgen receptor", PLoS One, 8:e65016 (2013).

Jia, et al., "Overcoming EGFR(T790M) and EGFR(C797S) resistance with mutant-selective allosteric inhibitors", Nature, 534(7605):129-132 (2016).

Joo, et al., "MET signaling regulates glioblastoma stem cells", Cancer Res., 72:3828-2838 (2012).

Kelleher, et al., "An evolving view if the eukaryotic oligosaccharyltrasferase", Glycobiology, 16:47R-62R (2006).

Kwak, et al., "Irreversible inhibitors of the EGF receptor may circumvent acquired resistance to gefitinib", Proc. Natl. Acad. Sci. USA, 102(21):7665-7670 (2005).

Landi , et al., "HER2 and lung cancer", Expert Rev Anticancer Ther., 13(10):1219-1228 (2013).

Lee, et al., "Primary resistance to epidermal growth factor receptor (EGFR) tyrosine kinase inhibitors (TKIs) in patients with non-small-cell lung cancer harboring TKI-sensitive EGFR mutatuions: an exploratory study", Ann Oncol., 24(8):2080-2087 (2013).

Lopez-Sambrooks, et al., "Oligosaccharyltransferase inhibition induces senescence in RTK-driven tumor cells", Nat. Chem. Biol., 12(12):1023-30 (2016).

(56) References Cited

OTHER PUBLICATIONS

Lu, et al., "Olig2-Dependent Reciprocal Shift in PDGF and EGF receptor Signaling Regulates Tumor Phenotype and Mitotic Growth in Malignant Glioma", Cancer Cell, 26:669-683 (2016).
Lynch, et al., "Activating mutations in the epidermal growth factor receptor underlying responsiveness of non-small-cell lung cancer to getfitinib", N Eng J Med., 350(21):2129-2139 (2004).
Ma, et. al., "InsR/IGF1R Pathway Mediates Resistance to EGFR Inhibitors in Glioblastoma", Clin. Cancer Res., 22:1767-1776 (2016).
Macijauskiene, et al., "Dementia with Lewy bodies: the principles of diagnostics, treatment, and management", Medicina (Kaunas), 48(1):1-8 (2012).
Mahajan, et al., "Cross talk of tyrosine kinases with the DNA damage signaling pathways", Nucleic Acid Res.,43:10588-10601 (2015).
Mok, et al., "Osimertinib or Platinum-Permetrexed in EGFR T790M-Positive Lung Cancer", N Engl. J Med., 376(6):629-640 (2017).
Nierderst, et al., "RB loss in resistant EGFR mutant lung adenocarcinomas that transform to small-cell lung cancer", Nat. Commun., 6:6377 (2015).
Nilsson, et al., "Stress hormones promote EGFR inhibitor resistance in NSCLS: Implications for combinations with β-blockers", Sci Trans Med., 9(415) (2017).
Ozawa, et. al., "Most human non-GCIMP glioblastoma subtypes evolve from a common pronueral-like precursor glioma", Cancer Cell., 26:288-300 (2014).
Pao, et al., "KRAS mutations and primary resistance of lung adenocarcinomas to getfitinib orerlotinib", PLoS Med., 2(1):e17 (2005a).
Pao, et al., "Acquired resistance of lung adenocarcinomas to getfitinib or erlotinib is associated with a second mutation in the EGFR kinase domain", PLoS Med., 2(3):e73 (2005b).
Park, et al., "CRIPTO1 expression in EGFR-mutant NSCLS elicits intrinsic EGFR-inhibitor resistance", J Clin Invest., 124(7):3003-3015 (2014).
Peereboom, et al., "Phase II trial of erlotinib with temozolomide and radiation in patients with newly diagnosd glioblastoma multiforme", J Neurooncol., 98:93-99 (2010).
Puschnik, et al., "A small molecule oligosaccharyltrasferase inhibitor with pan-flaviviral activity", Cell Rep., 21(11):3032-3039 (2017).
Sambrooks, et al., "Oligosaccharyltransferase Inhibition Overcomes Therapeutic Resistance to EGFR Tyrosine Kinase Inhibitors", Cancer Res., 78(17):5094-5106 (2018).
Schmidt-Ullrich, et al., "ERBB receptor tyrosine kinases and cellular radiation responses", Oncogene, 22:5855-5865 (2003).
Sequist, et al., "First-line gefitinib in patients with advanced non-small-cell lung cancer harboring somatic EGFR mutations", J. Clin Oncol., 26(15):2442-2449 (2008).
Sequist, et al., "Genotypic and histological evolution of lung cancers acquiring resistance to EGFR inhibitors", Sci. Transl. Med., 3(75):75ra26 (2011).
Singh, et al., "Transforming fusions of FGFR and TACC genes in human glioblastoma", Science, 337:1231-1235 (2012).
Stommel, et al., "Coactivation of receptor tyrosine kianses affects the response of tumor cells to targeted therapies", Science, 318:287-290 (2007).
Tang, et al., "Characterization of osimertinib (AZD9291)-resistant non-small cell lung cancer NCI-H1975/OSIR cell line", Oncotarget, 7(49):81598-81610 (2016).
Thress, et al., "Acquired EGFR C797S mutation mediates resistance to AZD9291 in non-small cell lung cancer harboring EGFR T790M", Nat Med., 21(6):560-562 (2015).
Tsuda, et al., "The Asn-420-Linked Sugar Chain in Human Epidermal Growth Factor Receptor Suppresses Ligand-independent Spontaneous Oligomerization", J Biol Chem, 275(29):21988-21994 (2000).
Ullrich, et al., "Human epidermal growth factor receptor cDNA sequence and aberrant expression of the amplified gene in A431 epidermoid carcinoma cells", Nature, 309(5967):418-425 (1984).
Vasquez-Martin, et al., "IGF-iR/epithelianl-to-mesenchymal transition (EMT) crosstalk suppresses the erlotinib-sensitizing effect of EGFR exon 19 deletion mutations", Sci Rep., 3:2560 (2013).
Verhaak, et al., "Integrated Genomic Analysis Identifies Clinically Relevant Subtypes of Glioblastoma Characterized by abnormalitites in PDGFRA, IDH1, EGFR, and NF1", Cancer Cell, 17:98-110 (2010).
Wilson, et al., "Widespread potential for growth-factor-driven resistance to anticancer kinase inhibitors", Nature, 487(7408):505-509 (2012).
Yao, et al., "TG-β IL-6 axis mediates selective and adaptive mechanisms of resistance to molecular targeted therapy in lung cancer", Proc Natl Acad Sci USA, 107(35):15535-15540 (2010).
Yoshida, et al., "Tyrosine phosphoproteomics Identifies Both Codrivers and Cotargeting Strategies for T790M-Related EGFR-TKI Resistance in Non-Small Cell Lung Cancer", Clin Cancer Res., 20(15):4059-4074 (2014).
Yu, et al., "Analysis of tumor specimens at the time acquired resistance to EGFR-TKI therapy in 155 patients with EGFR-mutant lung cancers", Clin. Cancer Res., 19(8):2240-2247 (2013).
Zhang, et al., "ErbB2/HER2-Specific NK Cells for Targeted Therapy of Glioblastoma", J. Natl. Cancer Inst., 108(5):1-12 (2016).
Gilmore, et al., "Delivery strategies for siRNA-mediated gene silencing", Current Drug Delivery, 3(2):147-155 (2006).
Jo, et al., "Non-viral gene transfection technologies for genetic engineering of sem cells", European Journal of Pharmaceutics and BioPharmaceutics, 68(1):90-104 (2007).
Khan, A. et al., "Sustained polymeric delivery of gene silencing antisense ODNs, siRNA, DNAzymes and ribozymes: in vitro and in vivo studies", J Drug Target, 12:393-404 (2004).
Matsumoto, et al.., "Cationized gelation delivery of a plasmid DNA expressing small interference RNA for VEGF inhibits murine squamous cell carcinoma", Cancer Science, 97(4):313-321 (2006).
Morrisey, et al., "Characterization of nuclease-resistant ribozymes directed against hepatitis B virus RNA", Journal of Viral Hepatitis, 9:411-418 (2002).
Zhao, et al., "Lipofectamine RNAiMAX: An efficient siRNA transfection reagent in human embryonic stem cells", Molecular Biotechnology, 40(1):19-26 (2008).
Jo, et al., "Non-viral gene transfection technologies for genetic engineering of stem cells", *European Journal of Pharmaceutics and BioPharmaceutics*, 68(1):90-104 (2007).
Khan, et al., "Sustained polymeric delivery of gene silencing antisense ODNs, siRNA, DNAzymes and ribozymes: in vitro and in vivo studies", *J Drug Target*, 12:393-404 (2004).

* cited by examiner

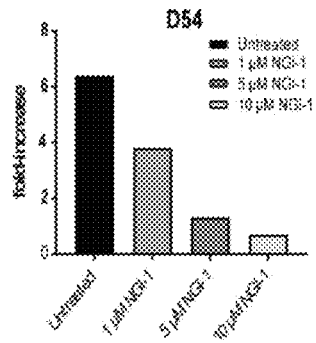 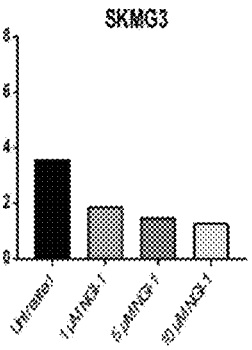 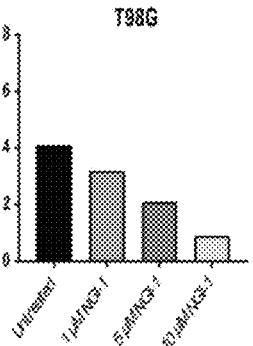 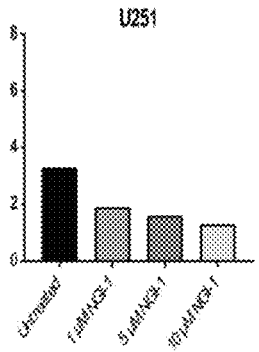
FIG. 2A  FIG. 2B  FIG. 2C  FIG. 2D
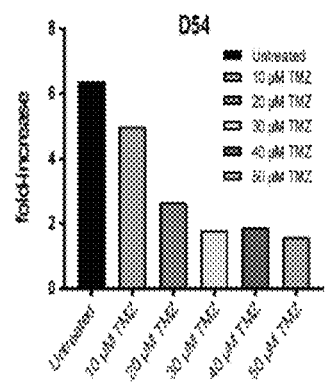 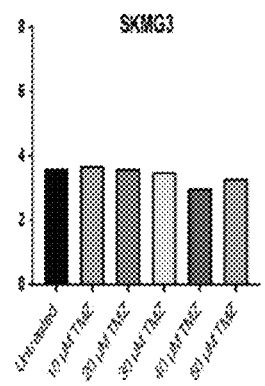 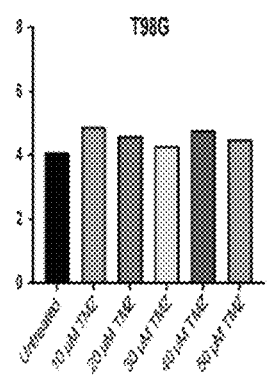 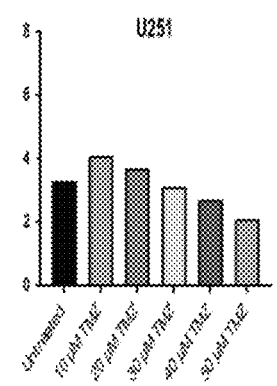
FIG. 2E  FIG. 2F  FIG. 2G  FIG. 2H
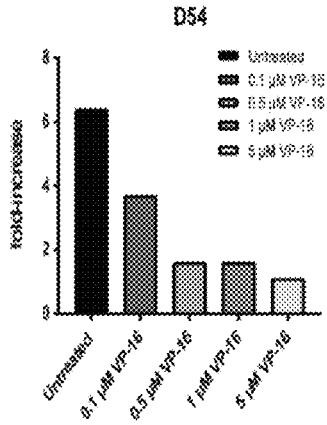 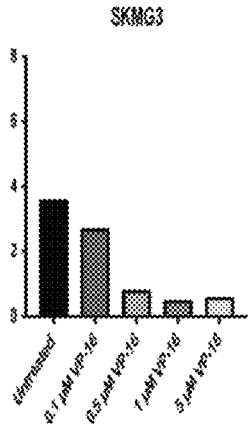 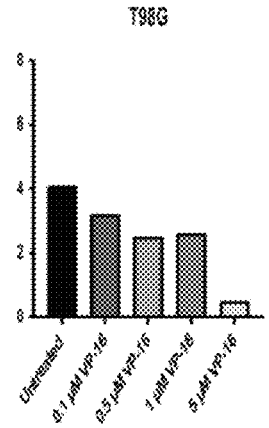 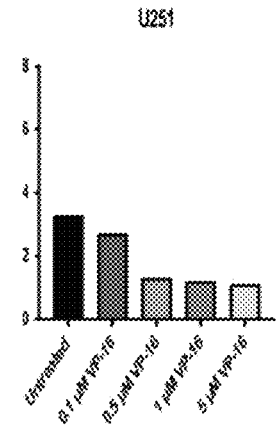
FIG. 2I  FIG. 2J  FIG. 2K  FIG. 2L

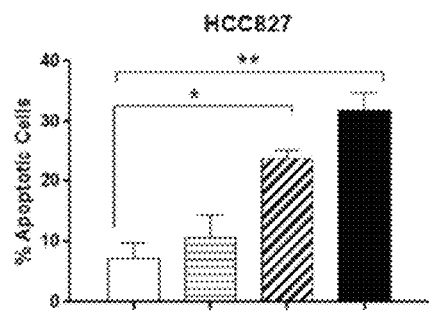
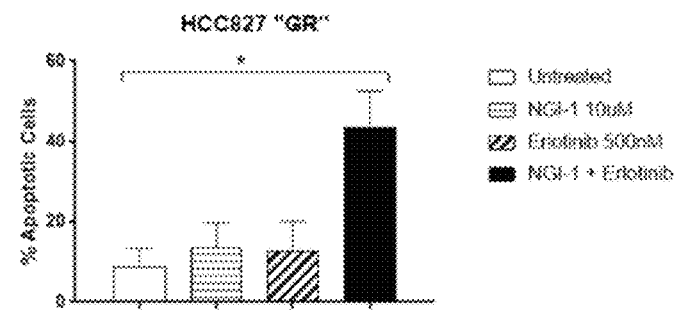
FIG. 11D  FIG. 11E
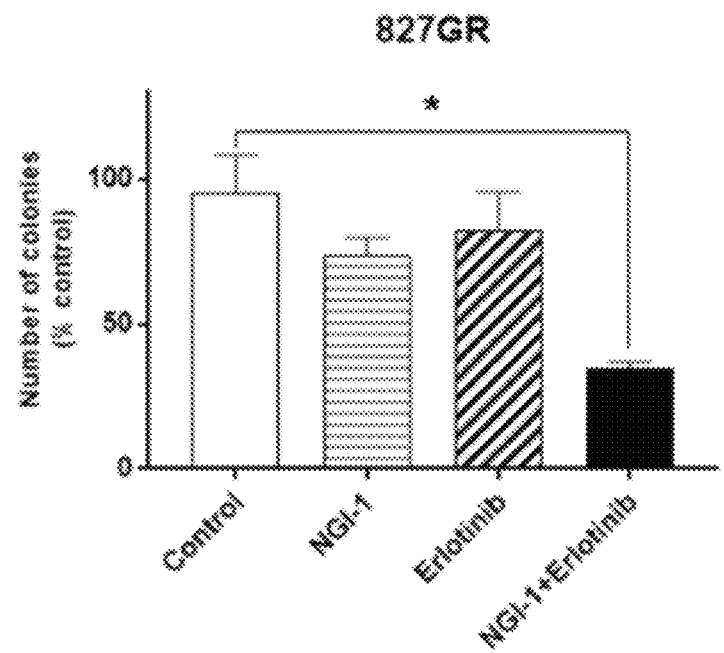
FIG. 11F

PARTICLE FORMULATION WITH POLYCATION COMPLEX

CROSS-REFERENCE TO RELATED APPLICATIONS

This application claims the benefit of and priority to U.S. Ser. No. 62/581,311 filed Nov. 3, 2017, and which is incorporated by reference in its entirety.

STATEMENT REGARDING FEDERALLY SPONSORED RESEARCH

This invention was made with government support under Grant No's. CA206386, CA172391 and CA149128 awarded by the National Institute of Health. The government has certain rights in the invention.

REFERENCE TO SEQUENCE LISTING

The Sequence Listing submitted as a text file named "YU_7117_ST25.txt," created on Nov. 2, 2018, and having a size of 2,646 bytes is hereby incorporated by reference pursuant to 37 C.F.R. § 1.52(e)(5).

FIELD OF THE INVENTION

The invention is directed to formulations for enhanced in vivo administration of small molecules such as oligosaccharyltransferase inhibitors like nerve growth inhibitor-1 (NGI-1) and methods of use thereof.

BACKGROUND OF THE INVENTION

NGI-1 is a small molecule inhibitor of the oligosaccharyltransferase ("OST"), a hetero-oligomeric enzyme that exists in multiple isoforms and transfers oligosaccharides to recipient proteins. In non-small-cell lung cancer cells, NGI-1 blocks cell-surface localization and signaling of the epidermal growth factor receptor (EGFR) glycoprotein, but selectively arrests proliferation in only those cell lines that are dependent on EGFR (or fibroblast growth factor, FGFR) for survival. NGI-1 has been shown to induce cell-cycle arrest accompanied by induction of p21, auto-fluorescence, and cell morphology changes, all hallmarks of senescence (Lopez-Sambrooks, et al., *Nat Chem Biol.* 12(12):1023-1030 (2016)). Thus, OST inhibition is a potential therapeutic approach for treating receptor-tyrosine-kinase-dependent tumors and a chemical probe for reversibly regulating N-linked glycosylation in mammalian cells.

However, the use of NGI-1 in vivo has been significantly hampered by its physico-chemical properties. NGI-1 cannot be delivered in vivo by standard methods.

Therefore, it is an object of the invention to provide effective ways of delivering therapeutic, diagnostic, and/or prophylactic agents in vivo, particularly agents targeting oligosaccharyltransferases.

It is also an object of the invention to provide polymeric formulation which are suitable for in vivo delivery of therapeutic, diagnostic, and/or prophylactic agents including chemotherapeutic agents, and methods of making thereof.

It is a further object of the invention to provide methods of using polymeric formulation for systemic delivery of therapeutic agents including NGI-1 in vivo.

SUMMARY OF THE INVENTION

Particle formulations of therapeutic agents for efficient in vivo delivery to target tissues are described. Typically, the compositions are in the form of polymeric particles formed from one or more polycationic polymers, one or more amphiphilic polymers, and one or more therapeutic agents. In some embodiments, particles include therapeutic agent complexed with a cationic polymer which is further encapsulated in one or more amphiphilic polymers, preferably diblock copolymer of a polyalkylene oxide and a polyester. Preferably, the cationic polymer is a polycationic polymer. In a particularly preferred embodiment exemplified in the experiments below, the diblock copolymer is a diblock poly(D,L-lactide)-poly(ethylene glycol) (PLA-PEG). PLA-PEG coats, or "encapsulates", the complexed structure between NGI-1 and PEI to mask the charge of PEI. Therefore, parameters such as surface charge, ratio between PLA-PEG and PEI/NGI-1, ratio between PEI and NGI-1, the bioactivity of NGI-1 after the complexation and encapsulation, are important.

In some embodiments, the therapeutic agent directly or indirectly inhibits the enzymatic activities of oligosaccharyltransferase (OST). In some embodiments, the therapeutic agent reduces or inhibits N-glycosylation of one or more receptor tyrosine kinases of the cancer cells. In some embodiments the therapeutic agent reduces other OST functions or interactions. In further embodiments, the therapeutic agent directly or indirectly reduces or inhibits downstream functions and/or cell-surface transport of one or more receptor tyrosine kinases of the cancer cells, including EGFR and FGFR family members. In some embodiments, the therapeutic agent is NGI-1 (5-(dimethylsulfamoyl)-N-(5-methyl-1,3-thiazol-2-yl)-2-(pyrrolidin-1-yl)benzamide), or functional derivatives or analogs thereof (jointly referred to as "NGI-1"). In some embodiments where the active agent is NGI-1, the polycationic polymer is polyethylenimine (PEI), and the amphiphilic polymer is diblock poly(lactic acid)-poly(ethylene glycol) (PLA-PEG).

Pharmaceutical compositions including the therapeutic agents formulated in the particles and a pharmaceutically acceptable carrier, and methods of use thereof for treatment or prevention of one or more symptoms of a disease or disorder such as cancer, are also provided. The pharmaceutical compositions can be administered to a subject in need thereof in an effective amount to reduce, alleviate, or prevent one or more symptoms. In some embodiments, in subjects with tumors, the pharmaceutical compositions are effective to reduce tumor burden, reduce tumor progression, or a combination thereof. In some embodiments, the methods are effective in reducing, or inhibiting enzymatic activity or interactions of the oligosaccharyltransferase (OST) enzyme complex. In further embodiments, the methods are effective in treating cancers associated with one or more mutations in one or more receptor tyrosine kinases of the tumor cells.

In some embodiments, the methods include administering, prior to, at the same time as, or after administration of the NG-1 type formulations, to the subject one or more additional active agents or procedure such as radiation, chemotherapy, immunotherapy, targeted therapy, or surgical removal against cancer. The pharmaceutical compositions can be administered prior to or in conjunction with an additional cancer therapy and/or procedure.

Data are represented as the mean±standard error. An * indicates a significant difference (p≤0.05) compared to radiation alone.

FIGS. 2A-2L are bar graphs showing the dose-response of NGI-1, temozolomide and etoposide in glioma cell lines. The graphs show fold increases in proliferation for NGI-1 (2A-2D), temozolomide (TMZ) (2E-2H) and etoposide (vp-16) (2I-2L) in D54, SKMG3, U251 and T98G after 5 days of drug exposure. Cultures were treated as described in Material and Methods.

FIGS. 3A-3H are bar graphs showing the combined effects of NGI-1 and cytotoxic chemotherapy on glioma cell proliferation. The graphs show fold increases in proliferation for D54 (3A-3B) and SKMG3 (3C-3D) and T98G (3E-3F) and U251 (3G-3H) after 5 days of drug exposure. Cultures were treated as described in Materials and Methods. The results are mean values±standard error for three independent experiments for each cell line. An * indicates a significant difference (p≤0.05).

FIGS. 4A-4H are bar graphs showing the effects of NGI-1 on cell cycle and γH2AX foci formation. Flow cytometry and cell cycle distribution of D54, SKMG3, T98G and U251 cells after vehicle or 10 μM NGI-1 treatment (4A-4D). Cells were also treated with 4 Gy under similar conditions and harvested for cell cycle analysis after 6 hours (4E-4H). The percent of cells in G1, S and G2/M are shown. Data were obtained from three independent experiments and are represented as mean±standard error. An * indicates a significant difference between NGI-1 treated and control samples (p≤0.05). FIGS. 4I-4L are bar graphs showing quantification of γH2AX foci in D54, SKMG3, T98G and U251 cells 2 hours after irradiation with 4 Gy in the presence or absence of 10 μM of NGI-1. Bar graphs represent the fold-increase of total number of foci counted per total number of cells in the picture. Foci of a cell were counted when a nucleus contained >10 foci. Data were obtained from three independent experiments and are represented as mean±standard error. An * indicates a significant difference between NGI-1 treated and control samples (p≤0.05).

Figure 5:
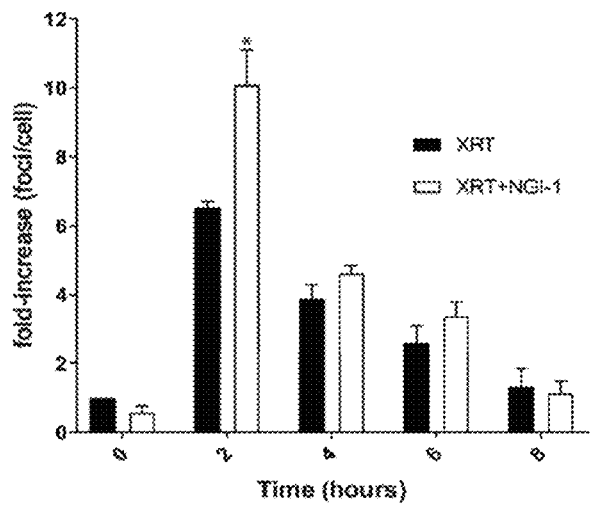

FIG. 5 is a bar graph quantification of γH2AX foci formation after 4 Gy in the presence or absence of 10 μM of NGI-1 in D54 cells at 0 (pre-radiation), 2, 4, 6 and 8 hours after radiation treatment. The graphs represent the fold-increase of total number of foci counted per total number of cells. Foci of a cell were counted when a nucleus contained >10 foci. Data were obtained from three independent experiments and are represented as mean±standard error. An * indicates a significant difference between NGI-1 treated and control samples (p≤0.05).

Figure 6A:
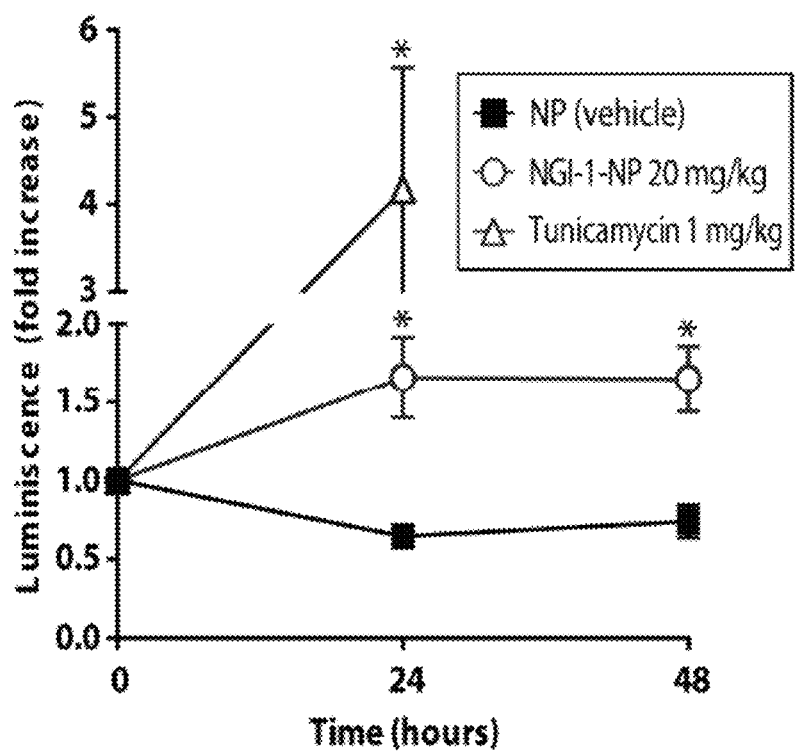
Figure 6B:
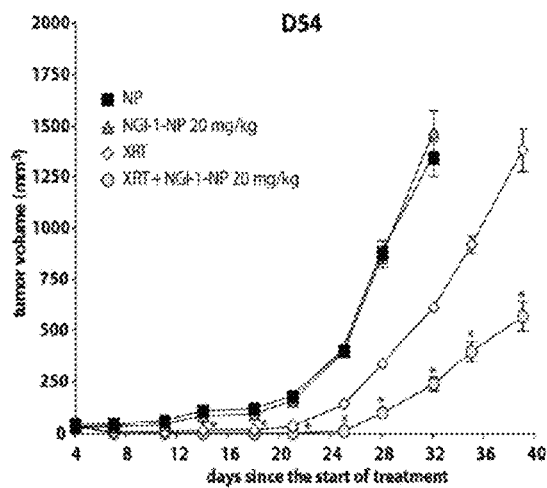

FIG. 6A is a line graph showing tumor average changes in luminescence with standard error for control NP (n=4), NGI-1-NP (n=8) or Tn (n=4) for D54 ER-LucT xenografts treated with i.v. control NPs, NGI-1 NP (20 mg/kg), or tunicmaycin (1 mg/kg) over 48 hours. FIGS. 6B (D54) and 6C (SKMG3) are bar graphs showing average xenograft tumor growth following treatment with control NP, NGI-1 NP, RT, or RT+NGI-1 NP. NPs were delivered 24 hours before the first fraction of radiotherapy (day 3) and on days 5 and 7 before radiation. An * indicates a significant difference between radiation+NGI-1 treated and radiation tumors (p≤0.05).

Figure 7A:
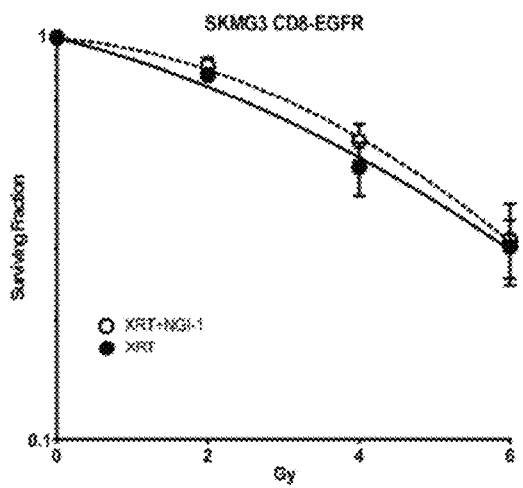
Figure 7B:
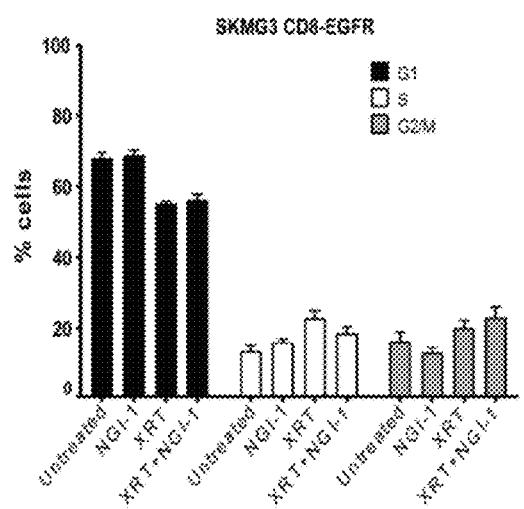
Figure 7C:
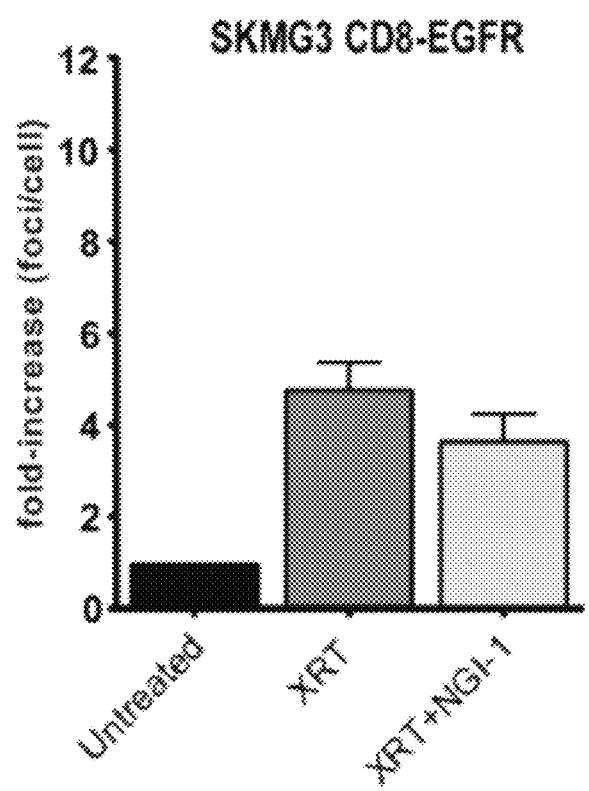

FIG. 7A is a line graph showing radiation dose response clonogenic survival in SKMG3-CD8-EGFR. Data represented the mean±S.E. for two independent experiments. FIG. 7B is a bar graphs showing quantification of γH2AX foci formation. FIG. 7C is a bar graph showing cell cycle distribution in control and irradiated cells (4 Gy) in the presence or absence of 10 μM of NGI-1.

Figure 8:
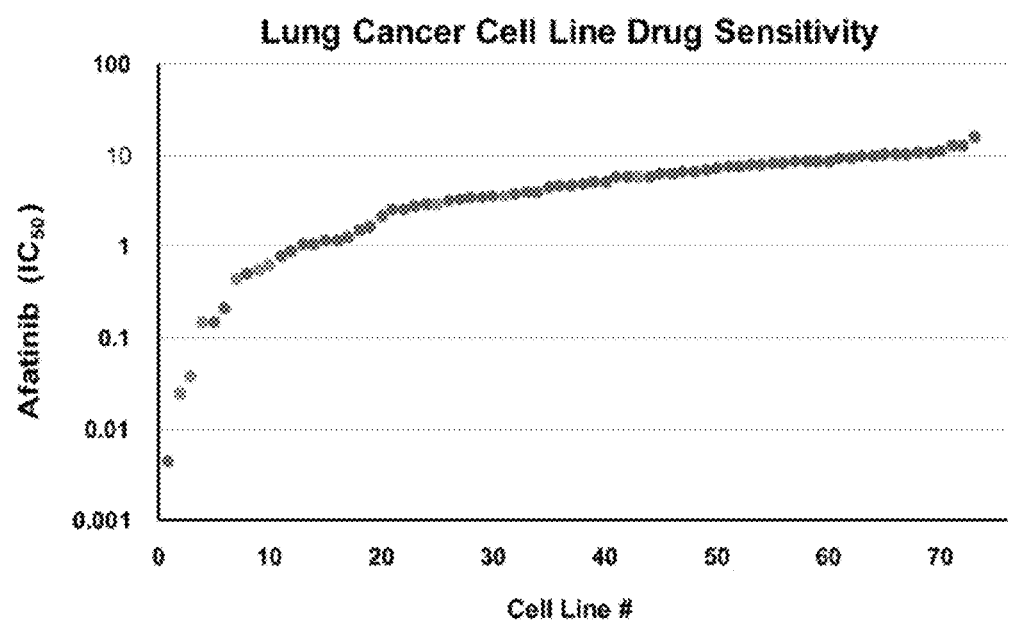

FIG. 8 is a dot plot showing comparisons of cell viability in 73 lung cancer cell lines after dose response treatment with afatinib or NGI-1. Afatinib $IC_{50}$ is plotted and NGI-1 sensitive or insensitive cell lines are marked to show a correlation of sensitivity between the two inhibitors (upper panel).

Figures 9A, 9B, 9C:
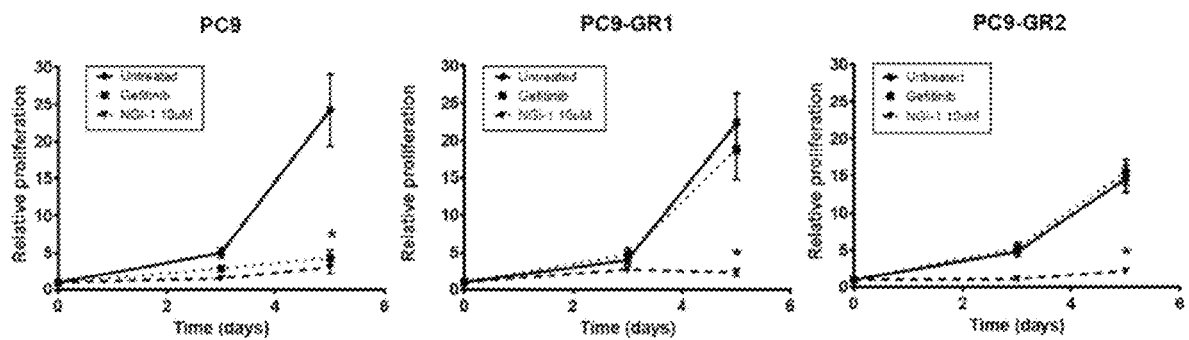
Figure 9D:
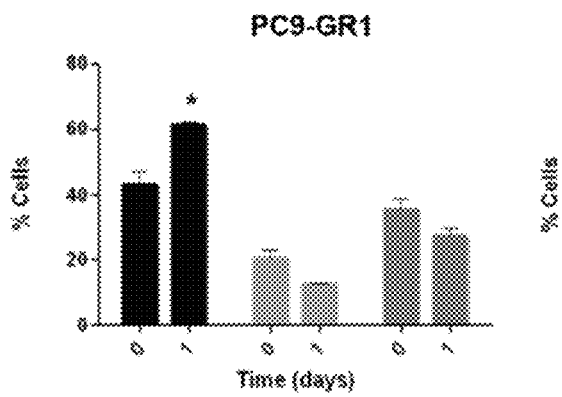
Figure 9E:
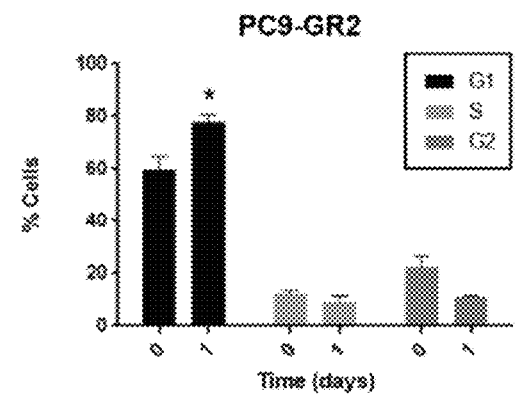

FIGS. 9A-9C are line graphs showing fold proliferation measured by MTT over 5 days with 10 μM NGI-1 or 100 nM Gefitinib treatment in PC9 and PC9-GR cells. FIGS. 9D-9E are bar graphs showing flow cytometry and cell cycle distribution of PC9-GR cells after NGI-1 treatment for 24 h. Data are represented as mean±s.d., n=3. P values were determined using two-tailed t-tests. *P<0.01.

Figure 10A:
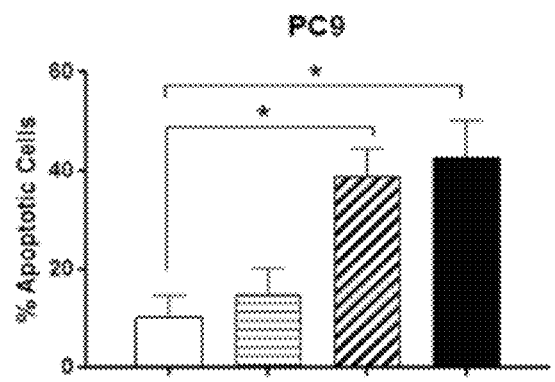
Figure 10B:
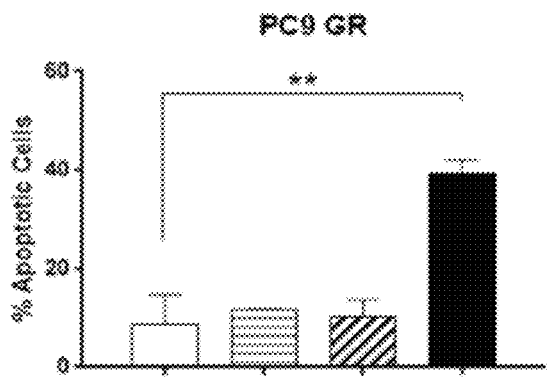
Figure 10C:
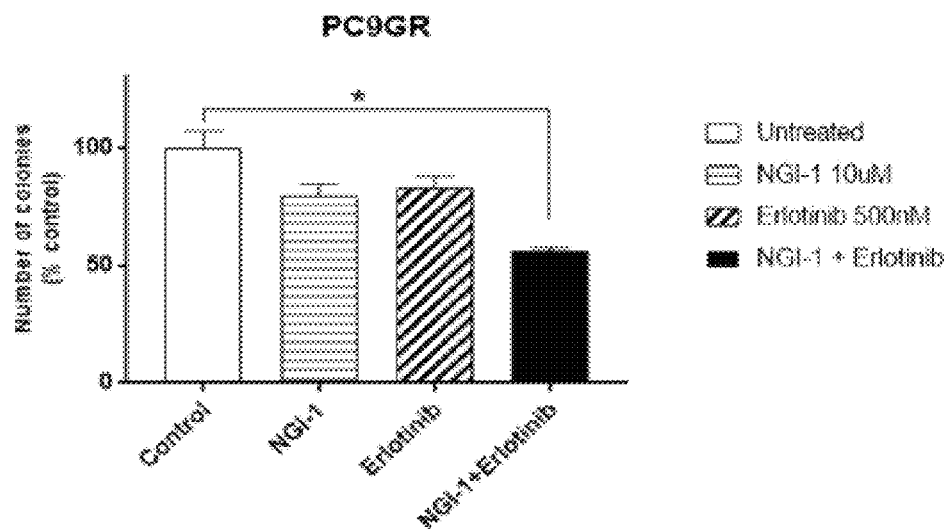

FIG. 10A-10B are bar graphs showing apoptosis susceptibility of PC9 and PC9-GR NSCLC cell lines following 48 h treatment with NGI-1 (10 μM), Erlotinib (0.5 μM) or a combination of both measured with Annexin-V and 7-AAD flow cytometry. Representative fluorescence data for each condition are displayed as bar graphs using the Flojo software. 100% values correspond to 50,000 cells and the data is represented as mean±s.d., n=3. P values were determined using two-tailed t-tests. *P<0.01. FIG. 10C is a bar graph showing clonogenic survival from three independent experiments for PC9-GR cells shown as the mean±s.d., n=3. *P<0.01.

Figure 11A:
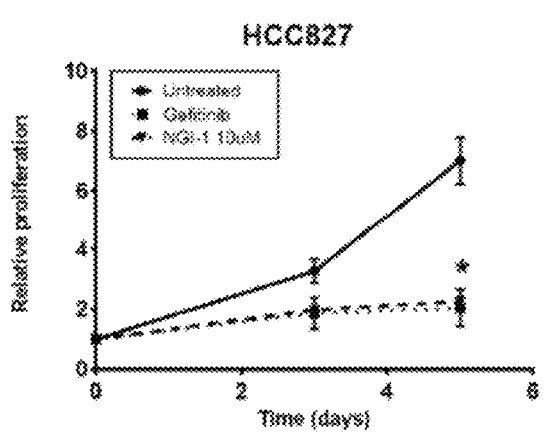
Figure 11B:
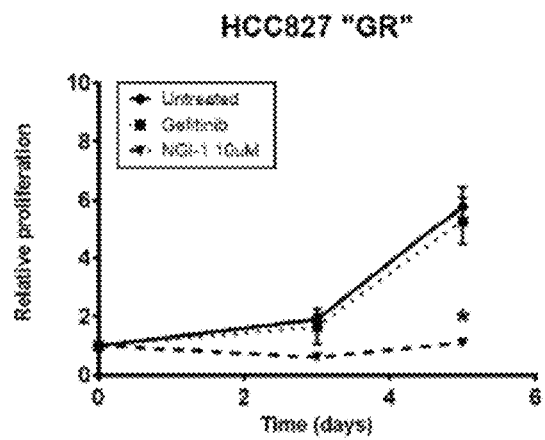
Figure 11C:
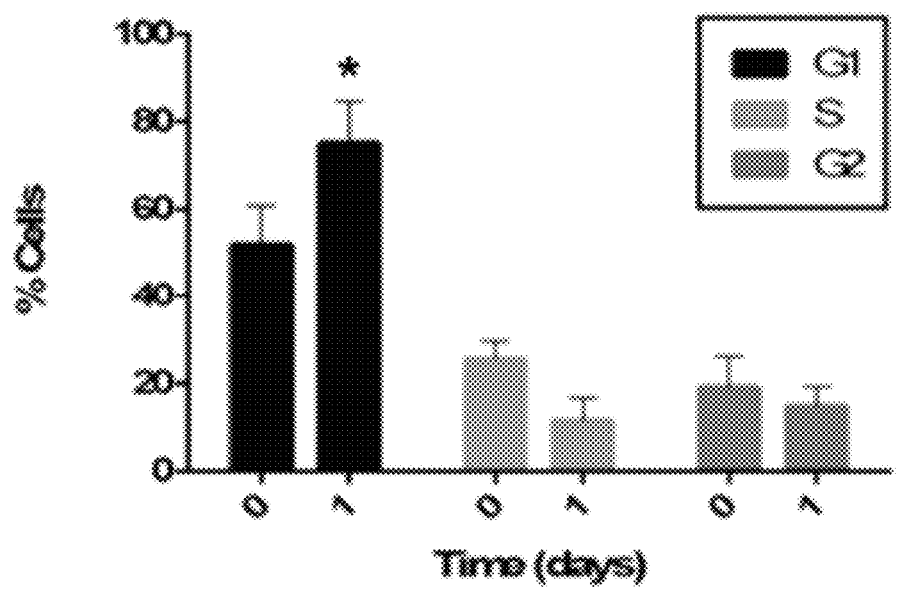

FIGS. 11A-11B are line graphs showing fold proliferation measured by MTT over 5 days with NGI-1 (10 μM) or Gefitinib (0.1 nM) treatment in HCC827 and HCC827-GR cells. FIG. 11C is a bar graph showing low cytometry and cell cycle distribution of HCC827-GR cells after NGI-1 treatment for 24 h. Data are represented as mean±s.d., n=3. *P<0.01. FIGS. 11D-11E are bar graphs showing apoptosis susceptibility of HCC827 and HCC827-GR NSCLC cell lines following 48 h treatment with NGI-1 (10 μM), Erlotinib (0.5 μM) or a combination of both measured with Annexin-V and 7-AAD flow cytometry as in FIG. 8. P<0.01. FIG. 11F** is a bar graph showing clonogenic survival of HCC827 and HCC827-GR NSCLC cell lines treated with vehicle, NGI-1 (10 μM), Erlotinib (0.5 μM) or a combination of both. The results represent data from three independent experiments for each cell line. Data for three independent experiments are shown as the mean±s.d. *P<0.01.

Figure 12A:
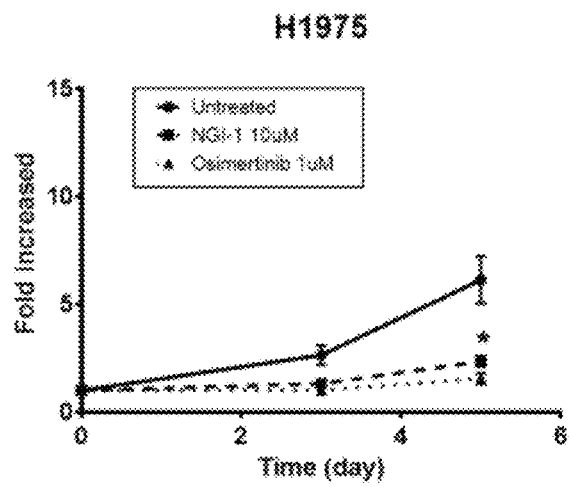
Figure 12B:
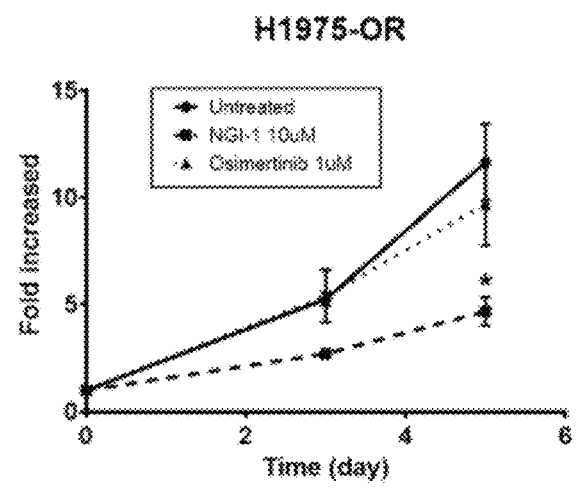
Figure 12C:
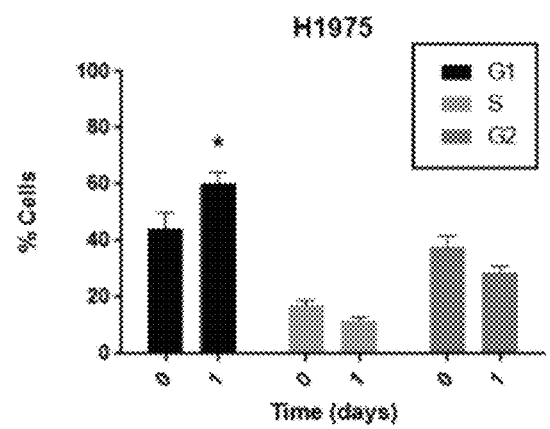
Figure 12D:
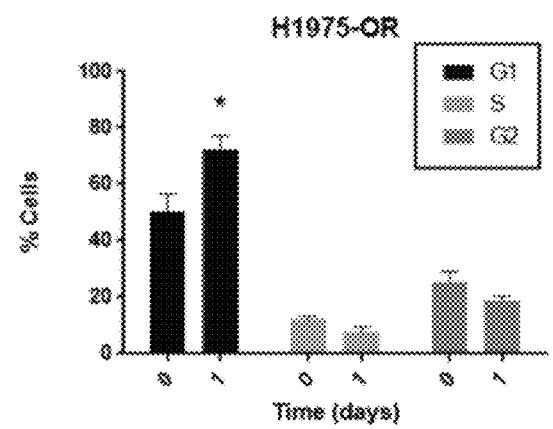
Figure 12E:
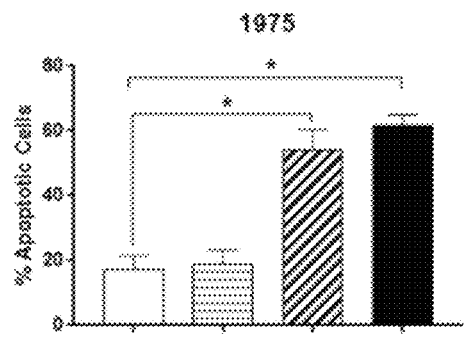
Figure 12F:
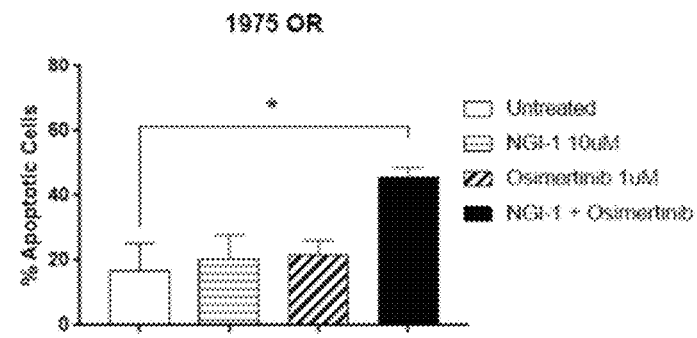
Figure 12G:
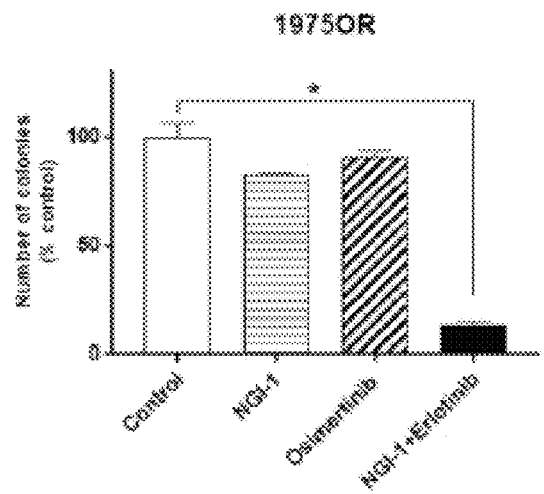

FIGS. 12A-12B are line graphs showing fold proliferation measured by MTT over 5 days with NGI-1 (10 μM), or Osimertinib (1 μM) treatment in H1975 and H1975-OR cells. FIGS. 12C-12D are bar graphs showing flow cytometry and cell cycle distribution of H1975 and H1975-OR cells after NGI-1 treatment for 24 h. Data are represented as mean±s.d., n=3. P values were determined using two-tailed t-tests. *P<0.01. FIG. 12E-12F are bar graphs showing apoptosis susceptibility of H1975 and H1975-OR NSCLC cell lines following treatment with NGI-1 (10 μM), Osimertinib (1 μM) or a combination of both for 48 h measured with Annexin-V and 7-AAD flow cytometry as in FIG. 8. The data represents the mean±s.d., n=3. *P<0.01. FIG. 12G is a bar graph showing clonogenic survival of H1975 and H1975-OR NSCLC cell lines treated with vehicle, NGI-1 (10 μM), Osimertinib (1 μM) or a combination of both. The bar graph shows data from three independent experiments and data represented as the mean±s.d., n=3. *P<0.01.

Figure 13A:
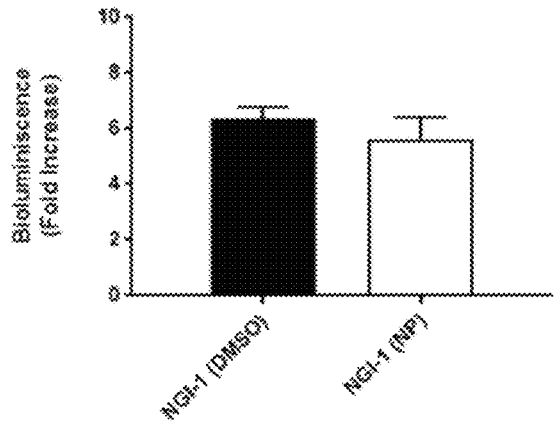
Figure 13B:
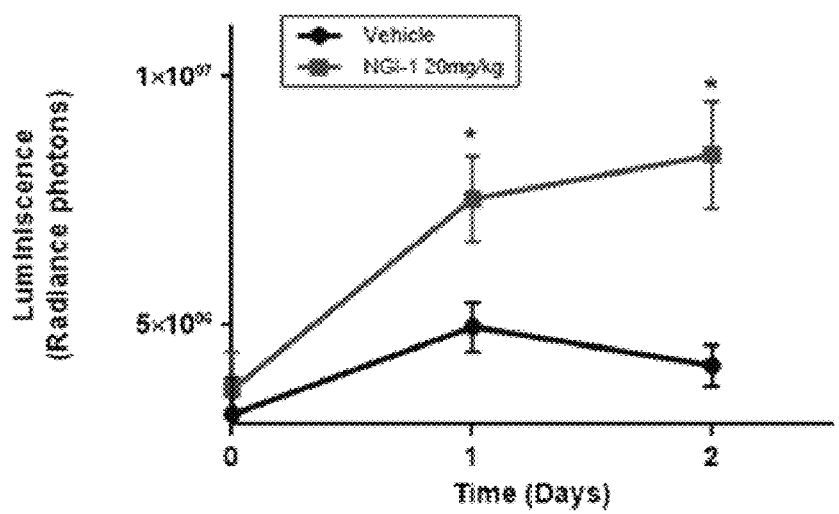
Figure 13C:
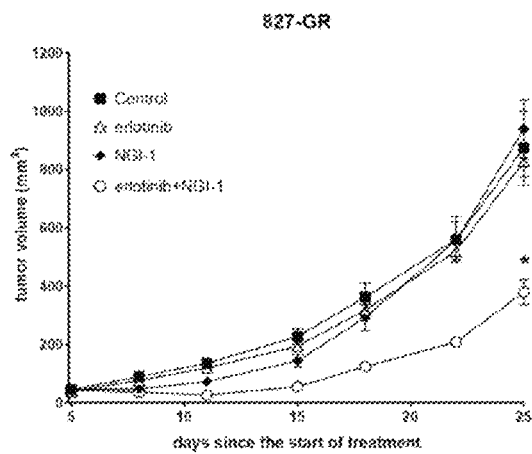
Figure 13D:
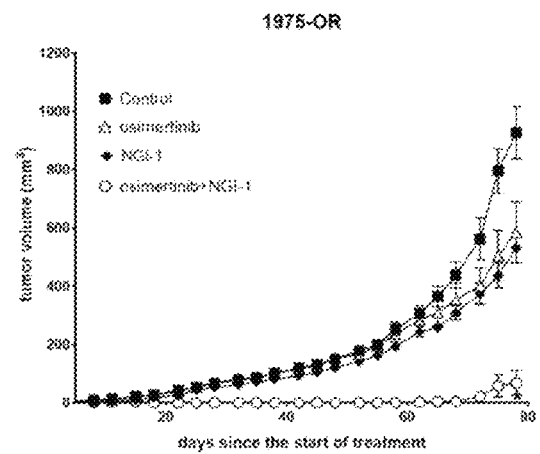

FIG. 13A is a bar graph showing fold increase of luciferase activity by NGI-1 dissolved in DMSO compared to the NGI-1 nanoparticle (NP) formulation. FIG. 13B is a line graph showing in vivo imaging over 48 h to detect inhibition of N-linked glycosylation in PC9 ER-LucT xenograft tumors following i.v. administration of blank (control) or NGI-1 NPs at a dose of 20 mg/Kg. FIGS. 13C-13D are line graphs showing tumor growth experiments in mice bearing HCC827-GR and H1975-OR xenografts, respectively. Tumors were randomized to four treatment groups: control; TKI, NGI-1, 20 mg/kg, and TKI+NGI-1. Mice were treated with a daily dose of TKI and every other day (3 times per week) with NGI-1 NPs. The data shows mean tumor volume for eight tumors in each group and error bars represent the SE. *P<0.01.

DETAILED DESCRIPTION OF THE INVENTION

I. Definitions

The term "carrier" or "excipient" refers to an organic or inorganic, natural or synthetic inactive ingredient in a formulation, with which one or more active ingredients are combined. In some embodiments, a carrier or an excipient is an inert substance added to a pharmaceutical composition to further facilitate administration of a compound, does not cause significant irritation to an organism and does not abrogate the biological activity and properties of the administered compound.

The terms "bioactive agent" and "active agent", used interchangeably, include physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of a condition or disease, or a symptom thereof, a substance which affects the structure or function of the body, or pro-drugs, which become biologically active or more active after they have been placed in a predetermined physiological environment. Examples include, but are not limited to, nucleic acids, both natural and synthetic analogs, small molecule (molecular weight less than 2000 D, more preferably less than 1000 D), peptidomimetics, proteins, and peptides, carbohydrates or sugars, lipids, or a combination thereof.

The term "derivative" refers to a modification including, but not limited to, hydrolysis, reduction, or oxidation products, of the compounds. Hydrolysis, reduction, and oxidation reactions are known in the art. The term "functional derivative" refers to a derivative of the compounds that retains the function of the compound, at least in part. In the case of NGI-1, a functional derivative of NGI-1 which has the effect of inhibiting oligosaccharyltransferase in cells.

The terms "sufficient" and "effective", used interchangeably, refer to an amount (e.g. mass, volume, dosage, concentration, and/or time period) needed to achieve one or more desired result(s).

The terms "effective amount" or "therapeutically effective amount" means a dosage sufficient to reduce or inhibit one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the severity of the disease or disorder being treated, as well as the route of administration and the pharmacokinetics of the agent being administered. The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "biocompatible", refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable", generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol.

The term "polymer," is given its ordinary meaning as used in the art, i.e., a molecular structure including one or more repeat units (monomers), connected by covalent bonds. The polymer may be a copolymer. The term "copolymer" generally refers to a single polymeric material that is comprised of two or more different monomers. The copolymer can be of any form, such as random, block, graft, etc. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks. The copolymers can have any end-group, including capped or acid end groups. The polymer can be modified with additional chemical moieties that are not polymeric, for example, conjugated to a lipid such as phospholipid. In some embodiments, the polymer is amphiphilic by further modification, for example by conjugating a hydrophilic polymer, or a cationic/anionic lipid, to a hydrophobic polymer. A blend is a mixture of two or more polymers.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. The amphiphilic compound can be, but is not limited to, one or a plurality of the following: naturally derived lipids, surfactants, polymers, or synthesized compounds with both hydrophilic and hydrophobic moieties. In the case where the amphiphilic molecule is an amphiphilic polymer, the hydrophilic moiety can be a hydrophilic polymer, and the hydrophobic moiety can be a hydrophobic polymer.

"Hydrophilic," refers to the property of having affinity for water. For example, hydrophilic polymers (or hydrophilic polymer segments) are polymers (or polymer segments) that are primarily soluble in aqueous solutions and/or have a tendency to absorb water. In general, the more hydrophilic a polymer is, the more that polymer tends to dissolve in, mix with, or be wetted by water. Hydrophilicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in water than in the organic solvent, then the compound is considered hydrophilic. For example, if the organic solvent is octanol, then a negative log P value indicates that the compound is hydrophilic. "Hydrophilic" may also refer to a material that when applied to a surface, such as glass, forms a contact angle with water, which is less than the contact angle of water on a surface of glass without the material.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water. Hydrophobicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in the organic solvent than in water, the compound is considered hydrophobic. For example, if the organic solvent is octanol, then a positive log P value indicates that the compound is hydrophobic. "Hydrophobic" may also refer to a material that when applied to a surface, such as glass, forms a contact angle with water, which is greater than the contact angle of water on a surface of glass without the material.

Hydrophilicity and hydrophobicity can be spoken of in relative terms, such as, but not limited to, a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Nanoparticle" generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres". Microspheres are typically more than one micron in average diameter, up to about 1000 microns.

"Mean particle size" generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

The phrases "parenteral administration" and "administered parenterally" are art-recognized terms, and include modes of administration other than enteral and topical administration, such as intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrasternal injection and infusion.

The terms "incorporated" and "encapsulated" refer to incorporating, formulating, or otherwise including an agent into and/or onto a composition that allows for release, such as sustained release, of such agent in the desired application.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound.

The terms "inhibit" and "reduce" means to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

II. Compositions

Compositions for efficient in vivo delivery of therapeutic agents to target cells or tissues are provided. The compositions are delivered in the form of microparticles or nanoparticles. The formulations are particularly suited for delivering therapeutic agents that are poorly water-soluble.

A. Particles

The particles can be micro or nano particles formed from one or more polycationic polymers, one or more amphiphilic polymers, and one or more therapeutic, prophylactic and/or diagnostic agents. One or more additional active agents can optionally be incorporated into the particles. The constituent polycationic polymers, amphiphilic polymers, and therapeutic agents can be incorporated in different ratios to provide particles with the desired physiochemical properties to facilitate in vivo delivery such as via intravenous injection, including particle size and surface charge. In some embodiments, the formulation has reduced systemic toxicity and/or side effects associated with the active agent compared to the free form. In some embodiments, the particle formulation increases the effective concentration at the target site by 5%, 10%, 20%, 30%, 40%, 50%, 60%, 70%, 80%, 90%, or more than 90% when the same total amount of active agent is administered.

One or more polycationic polymers are present in the particle carrier in an amount effective to complex with one or more therapeutic agents to form a particle having the desired particle size. The one or more polycationic polymers and one or more therapeutic agents can be incorporated into the particles at different ratios by weight. In certain embodiments, the polycationic polymer possesses one or more amine residues which are positively charged at physiological conditions.

The polycationic polymers and amphiphilic polymers can be incorporated into the particle carriers at different molar ratios or molecular weight ratios. In certain embodiments, the one or more polycationic polymers and one or more amphiphilic polymers are present in a ratio of between 1:20 and 10:1 by weight. In preferred embodiments, the one or more polycationic polymers and one or more amphiphilic polymers are present in a ratio of between 1:20 and 1:1 by weight.

In some embodiments, particles can have a core formed of an active agent complexed with one or more polycationic polymers, typically via non-covalent interactions. Exemplary non-covalent interactions include electrostatic interactions such as ionic interactions, hydrogen bonding, and halogen bonding; Van der Waals forces, effects, and hydrophobic effects, and combinations thereof. In preferred embodiments, the core complex is formed by ionic interactions between the active agent and one or more polycationic polymers.

Typically, the core complex including an active agent complexed with one or more polycationic polymers is encapsulated in a shell formed of one or more amphiphilic polymers, and optionally, including one or more hydrophobic polymers. The core-shell particles can be formed by a co-block polymer. The particles are particularly suited for delivering active agent in vivo where active agent alone may not be optimal for in vivo delivery. Generally, particles can be used to deliver the active agent to a site of interest, e.g., tumor site, with or without a targeting moiety.

Nanoparticles are preferred for intertissue application, penetration of cells, and certain routes of administration. The nanoparticles are provided as a population having an average or mean diameter size based on the intended use. The nanoparticles may have any diameter from about 10 nm to about 1,000 nm, inclusive. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 60 nm to 400 nm, from 50 nm to 350 nm, from 50 nm to 300 nm, or from 50 nm to 200 nm. In preferred embodiments the nanoparticles have a diameter less than 400 nm, less than 300 nm, or less than 200 nm, and greater than 30, 40, 50, 60, 80 or 100 nm. The preferred range is between 50 nm and 300 nm, or 25 nm and 250 nm, or 80 nm and 150 nm.

1. Polymers

The particle can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydolyzable crosslinking groups to render the crosslinked polymer insoluble or sparingly soluble in water.

Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof.

Amphiphilic Polymers

The particles are coated with one or more amphiphilic polymers. Amphiphilic block copolymers solubilize drugs, especially hydrophobic drugs in an aqueous environment. Amphiphilic copolymers can spontaneously self-assemble in aqueous solution to form NPs with a hydrophobic inner core and hydrophilic outer shells. Amphiphilic polymers can include block copolymers of any of the hydrophobic and hydrophilic polymers. In preferred embodiments, the hydrophobic polymers are biodegradable polyesters such as poly(lactic-co-glycolic) acid (PLGA), poly(lactic acid) (PLA), or poly(glycolic acid) (PGA), and the hydrophilic polymers are polyalkylene oxides such as polyethylene glycol (PEG) or a PEG derivative or a block copolymer such as a PLURONIC® or POLOXAMER, most being polyalkylene oxide-polyalkylene glycol copolymers. Exemplary biodegradable polyesters are synthesized from monomers such as D, L-lactide, D-lactide, L-lactide, D, L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydroxybutyric acids, and malic acid. Preferably, the biodegradable polyester is synthesized from D, L-lactide, D-lactide, L-lactide, D, L-lactic acid, D-lactic acid, L-lactic acid, glycolide, glycolic acid, and combinations thereof. Optionally, the polymers that form the particles contain linkers between the blocks of hydrophilic and hydrophobic polymers.

Hydrophobic Polymers

The particle can contain one or more hydrophobic polymers. Examples of suitable hydrophobic polymers include polyhydroxy acids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In preferred embodiments, the hydrophobic polymer is an aliphatic polyester. In the most preferred embodiments, the hydrophobic polymer is poly(lactic acid), poly(glycolic acid), or poly(lactic acid-co-glycolic acid).

In preferred embodiments, the hydrophobic polymer is poly(lactic acid), poly(glycolic acid), or poly(lactic acid-co-glycolic acid). Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

Hydrophilic Polymers

The particle can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

The molecular weight of the polymers can be varied to tailor the properties of polymeric particle. For example, the molecular weight of the hydrophobic polymer segment can be varied to engineer particles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

Cationic Polymers

The particles have a core formed of a therapeutic, prophylactic or diagnostic agent complexed with one or more biocompatible, polycationic polymers. The polycationic polymer can be any synthetic or natural polymer bearing at least two positive charges per molecule and having sufficient charge density and molecular size to bind to the active agent under physiological conditions (i.e., pH and salt conditions encountered within the body or within cells). In certain embodiments, the polycationic polymer contains one or more amine residues.

Polycationic polymers can be either linear or branched and can be either homopolymers or copolymers. Amino acid components can have either L or D configuration, and can have any mixture of these features. Branched cationic polymers can enhance the capacity of the polymer to conjugate to a coating agent such as PLA-PEG. Preferably, the cationic polymer molecule is sufficiently flexible to allow it to form a compact complex with one or more therapeutic molecules. In some embodiments, the biocompatible polymer(s) is biodegradable.

In some embodiments, the polycationic polymer has a molecular weight of between about 5,000 Daltons and about 100,000 Daltons, more preferably between about 5,000 and about 50,000 Daltons, most preferably between about 10,000 and about 35,000 Daltons.

Suitable polycationic polymers include polyethylene imine (PEI), polyallylamine, polyvinylamine, polyvinylpyridine, aminoacetalized poly(vinyl alcohol), acrylic or methacrylic polymers (for example, poly(N,N-dimethylaminoethylmethacrylate)) bearing one or more amine residues, polyamine acids such as polyornithine, polyarginine, and polylysine, protamine, cationic polysaccharides such as chitosan, DEAE-cellulose, and DEAE-dextran, and polyamidoamine dendrimers, as well as copolymers and blends thereof. In preferred embodiments, the polycationic polymer is PEI. Preferred polymers are a cationic polymer with multiple free amines such as polyethylenimine (PEI) and poly-L-lysine (PLL).

Further exemplary cationic polymers include, but are not limited to, cyclodextrin-containing polymers such as those described in U.S. Pat. No. 6,509,323, poly(L-lysine) (PLL), chitosan, poly(glycoamidoamine), schizophyllan, DEAE-dextran, dextran-spermine, poly(amido-amine) (PAA), poly(4-hydroxy-L-proline ester), poly[R-(4-aminobutyl)-L-glycolic acid] (PAGA), poly(amino-ester), poly(phosphazenes) (PPZ), poly(phosphoesters) (PPE), poly(phosphoramidates) (PPA), TAT-based peptides, Antennapedia homeodomain peptide, MPG peptide, poly(propylenimine), carbosilane, and amine-terminated polyaminophosphine.

Copolymers of two or more polymers described above, including block and/or random copolymers, may also be employed to make the polymeric particles.

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb2>/<sl2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

In some embodiments, the core polymer is a branched polymer that is capable of enhancing conjugation of the coating agent and core polymer. Exemplary branched polymers include 25 kDa branched polyethyleneimine (PEI) and 5 kDa branched methoxy-PEG.

2. Therapeutic, Prophylactic and Diagnostic Agents

The polymers can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

Particles are used to deliver a therapeutic agent, prophylactic agent, diagnostic agent, or a combination thereof. Most properties of the therapeutic agents can be enhanced by complexing them prior to encapsulation (if necessary) to help charge-neutralize, and/or using a double emulsion technique to accommodate hydrophilic compounds. However, the larger the agent (molecular weight), the more difficult it will be to encapsulate it in a true "nano" particle (i.e. the diameter of the particles will become closer to microns not nanometers). The combination of all therapeutic properties will contribute to the size of the resulting particles. While NG-1 does not have any formal charge, it does have 7H-bond acceptors and only 1H-bond donor, loading NG-1 into particles by itself made the particles much more negative compared to unloaded particles. It was found empirically that the addition of a positively charged complexing agent, PEI, to the NG-1 prior to encapsulation of the drug both decreased the charge of the particles and increase the loading efficiency of the drug as well as increased the absolute loading amount of drug. This result may, theoretically, be due to the net electropositive potential of the NG-1 molecule compared to that of the tertiary amines of the PEI.

Encapsulation efficiency is measured can depend on the property of the agent encapsulated. Generally it can be done by dissolving the particles in a solvent that does not negatively affect the integrity of the encapsulated agent, separating the agent out (using either phase, gravitational, or size-filtration), and analyzing the agent via mass spectroscopy or liquid chromatography. The quantity of the encapsulated agent can also be determined by comparing the absorbance of the solvent containing the encapsulated agent released from dissolved particles, to a standard curve of known concentrations of the encapsulated agent in the same solvent used to dissolve the particles.

In terms of release, the release profile of an encapsulated agent can depend on a number of factors, such as the medium into which the particles are releasing the encapsulated agent, the properties of the therapeutic agents, the polymers forming the particles, or a combination thereof. There are some trends in terms of how the properties affect the release profile, but these relationships are generally not well-defined and empirical release must be characterized for each new therapeutic agent-polymer particle combination.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, antisense, aptamers, small interfering RNAs, ribozymes, external guide sequences for ribonuclease P, and triplex forming agents.

Compounds with a wide range of molecular weight can be encapsulated, for example, between 100 and 500,000 grams or more per mole. The agent to be delivered can be a small molecule agent (i.e., non-polymeric agent having a molecular weight less than 2,000, 1500, 1,000, 750, or 500 Dalton) or a macromolecule (e.g., an oligomer or polymer) such as proteins, enzymes, peptides, nucleic acids, etc. Suitable small molecule active agents include organic, inorganic, and/or organometallic compounds.

Representative agents include proteins such as cytokines, hormones, growth factors, antibodies and fragments thereof, vaccines, anti-infectives including antibacterial agents, antiviral agents and anti-fungal agents, and chemotherapeutic agents. Other agents include anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells). The agents may also be nutraceuticals.

Representative anti-cancer chemotherapeutic agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMIDE®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In some embodiments, the particles include nucleic acid cargo, including, but not limited to, functional nucleic acids, expression constructs or mRNA, or a combination thereof. For example, in some embodiments, a functional nucleic acid is designed to reduce expression of an oncogene, for example a growth factor (e.g., c-Sis), mitogen, receptor tyrosine kinase (e.g., EGFR, FGFR, PDGFR, VEGFR, HER2/neu, MET (HGFR)), cytoplasmic tyrosine kinase (e.g., Src, Syk-ZAP-70, BTK families) cytoplasmic serine/threonine kinases (or a regulator subunit thereof) (e.g., Raf, cyclin-dependent kinases), regulatory GTPases (e.g., Ras), transcription factors (e.g., myc), angiogenesis (e.g., VEGF), or a combination thereof. Representative pro-apoptotic agents include, but are not limited to, fludarabinetaurosporine, cycloheximide, actinomycin D, lactosylceramide, 15d-PGJ(2) and combinations thereof.

Examples of immunodulators such as immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components: DNA carriers (or delivery vehicles) and DNAs encoding antigens. DNA carriers protect DNA from degradation, and can facilitate DNA entry to specific tissues or cells and expression at an efficient level.

In some embodiments, the therapeutic agent is one or more therapeutic drugs that interfere with N-glycosylation or cell-surface transport. In some embodiments, the therapeutic agent targets the function of the OST. Preferably, the therapeutic agents decrease activation of receptor tyrosine kinase (RTK) proteins such as epidermal growth factor receptor (EGFR) and fibroblast growth factor receptor (FGFR) family members. EGFR family consists of four members including EGFR (ErbB1, HER1), ErbB2 (HER2, neu in rodents), ErbB3 (HER3) and ErbB4 (HER4). FGFR family consists of FGFR1, FGFR2, FGFR3, FGFR4.

In some embodiments, the therapeutic agents are inhibitors that reduce, or inhibit N-glycosylation of glycoproteins, specifically ones involved in the oncogenesis such as RTKs. Exemplary glycosylation inhibitors are nucleoside antibiotics such as tunicamycin, plant alkaloids such as castanospermine, australine, deoxynojirimycin, swainsonine, and mannostatin A, or any derivatives thereof. In some embodiments, the therapeutic inhibitors are substrate analogs of specific transferases of the glycosylation pathway. In some embodiments, the therapeutic agents are compounds that interfere with N-glycosylation, and/or cell-surface transport of RTK proteins. In further embodiments, the therapeutic agents are compounds that reduce or inhibit proliferation and/or induce senescence in tumor cells. Exemplary compounds are described in Lopez-Sambrooks, et al., *Nat Chem Biol.* 12(12):1023-1030 (2016) and WO 2017/019540 and are specifically incorporated by reference herein.

The therapeutic agents can be compounds that have the formula:

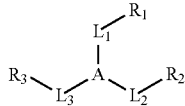

Formula I wherein,

A is unsubstituted aryl, substituted aryl, unsubstituted polyaryl, substituted polyaryl, substituted heteroaryl, unsubstituted heteroaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl. Preferably, A is unsubstituted aryl;

$L_1$, $L_2$, and $L_3$ are independently absent, —$SO_2$—, —NHC(O)—, —NR$^{a'}$C(O)—, —C(O)NH—, —C(O)NR$^{a'}$—, —C(O)O—, —OC(O)—, —C(O)—, —C(O)OCH$_2$—, —$SO_2$NR$^{a'}$—, —CH$_2$R$^{a'}$—, —O—, —NR$^{a'}$H—, —NR$^{a'}$—, —OCONH—, —NHCOO—, —OCONR$^{a'}$—, —NR$^{a'}$COO—, —NHCONH—, —NR$^{a'}$CONH—, —NHCONR$^{a''}$—, —NR$^{a'}$CONR$^{a''}$—, —CHOH—, —CR$^{a'}$OH—, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted $C_1$-$C_{20}$ carbonyl); R$^{a'}$ and R$^{a''}$ is hydrogen, halogen (F, Cl, Br, I), hydroxyl, unsubstituted alkyl (such as unsubstituted $C_1$-$C_{20}$ alkyl), substituted alkyl (such as substituted $C_1$-$C_{20}$ alkyl), substituted alkylene (such as substituted $C_1$-$C_{20}$ alkylene), unsubstituted alkylene (such as unsubstituted $C_1$-$C_{20}$ alkylene), substituted alkenyl (such as substituted $C_1$-$C_{20}$ alkenyl), unsubstituted alkenyl (such as unsubstituted $C_1$-$C_{20}$ alkenyl), substituted alkylamino (such as substituted $C_1$-$C_{20}$ alkylamino), unsubstituted alkylamino (such as unsubstituted $C_1$-$C_{20}$ alkylamino), substituted carbonyl (such as substituted $C_1$-$C_{20}$ carbonyl), or unsubstituted carbonyl (such as unsubstituted $C_1$-$C_{20}$ carbonyl), an aryl group, or a heterocyclic group. Preferably $L_1$ is —$SO_2$—, $L_2$ is absent $L_3$ is —NHC(O)—;

$R_1$, $R_2$, and $R_3$ are independently absent, hydrogen, substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, unsubstituted $C_3$-$C_{20}$ cycloalkynyl, substituted alkylamine, unsubstituted alkylamine, substituted dialkylamine, unsubstituted dialkylamine, substituted aralkylamine, unsubstituted aralkylamine, substituted diaralkylamine, unsubstituted diaralkylamine, substituted N-aryl-N-alkylamine, unsubstituted N-aryl-N-alkylamine, substituted alkyl, unsubstituted alkyl, substituted alkenyl, unsubstituted alkenyl, substituted alkynyl, or unsubstituted alkynyl. Preferably, $R_1$ is unsubstituted dialkylamine, substituted dialkylamine, substituted $C_3$-$C_{20}$ heterocyclyl, unsubstituted $C_3$-$C_{20}$ heterocyclyl, substituted N-aryl-N-alkylamine, unsubstituted N-aryl-N-alkylamine, substituted aralkylamine, or unsubstituted aralkylamine. Preferably, $R_2$ is hydrogen, substituted $C_3$-$C_{20}$ heterocyclyl, unsubstituted $C_3$-$C_{20}$ heterocyclyl, substituted $C_3$-$C_{20}$ cycloalkyl, unsubstituted $C_3$-$C_{20}$ cycloalkyl, substituted dialkylamine, or unsubstituted dialkylamine. Preferably, $R_3$ is substituted heteroaryl, unsubstituted heteroaryl, substituted aryl, unsubstituted aryl, substituted polyaryl, unsubstituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, or unsubstituted $C_3$-$C_{20}$ heterocyclyl.

In some forms of Formula I, at least one of $L_1$, $L_2$, and $L_3$ is present.

In some forms of Formula I, at least one of $R_1$, $R_2$, and $R_3$ is a group other than hydrogen.

In some forms of Formula I, at least one of $L_2$ is absent, and at least one of $R_1$, $R_2$, and $R_3$ is a group other than hydrogen.

In some forms of Formula I, at least one of $L_2$ is absent, $R_2$ is hydrogen, and $R_1$ and $R_3$ are groups other than hydrogen.

In some forms, the compounds of Formula I have the formula:

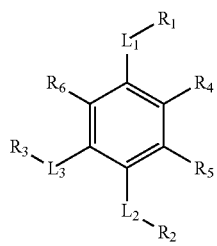

Formula II wherein, $R_4$, $R_5$, and $R_6$ are independently hydrogen, substituted alkyl, unsubstituted alkyl, unsubstituted aryl, substituted alkenyl, unsubstituted alkenyl, substituted alkynyl, unsubstituted alkynyl, substituted polyheteroaryl, unsubstituted polyheteroaryl, substituted aryl, unsubstituted aryl, substituted heteroaryl, unsubstituted heteroaryl, substituted polyaryl, unsubstituted polyaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl, substituted alkoxy, unsubstituted alkoxy, substituted aroxy, unsubstituted aroxy, substituted alkylthio, unsubstituted alkylthio, substituted arylthio, unsubstituted arylthio, substituted carbonyl, unsubstituted carbonyl, substituted carboxyl, unsubstituted carboxyl, substituted amino, unsubstituted amino, substituted amido, unsubstituted amido, substituted sulfonyl, unsubstituted sulfonyl, substituted sulfonic acid, unsubstituted sulfonic acid, substituted phosphoryl, unsubstituted phosphoryl, substituted phosphonyl, or unsubstituted phosphonyl. Preferably, $R_4$, $R_5$, and $R_6$ are hydrogen.

In some forms, the compounds of Formula I have the formula:

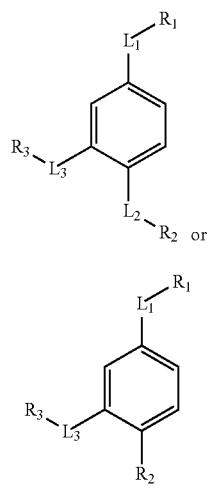

Formula III or

Formula IV wherein, $L_1$ and $L_3$ are independently —SO$_2$—, —NHC(O)—, —C(O)NH—, —C(O)O—, —OC(O)—, —C(O)—, —C(O)OCH$_2$—, —SO$_2$NH—, —O—, —OCONH—, —NHCOO—, —OCONH—, —NHCOO—, or —NHCONH—;

$R_1$ is unsubstituted dialkylamine, substituted dialkylamine, substituted $C_3$-$C_{20}$ heterocyclyl, unsubstituted $C_3$-$C_{20}$ heterocyclyl, substituted N-aryl-N-alkylamine, unsubstituted N-aryl-N-alkylamine, substituted aralkylamine, or unsubstituted aralkylamine;

$R_2$ is hydrogen, substituted $C_3$-$C_{20}$ heterocyclyl, unsubstituted $C_3$-$C_{20}$ heterocyclyl, substituted $C_3$-$C_{20}$ cycloalkyl, unsubstituted $C_3$-$C_{20}$ cycloalkyl, substituted dialkylamine, or unsubstituted dialkylamine; and $R_3$ is substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, or unsubstituted $C_3$-$C_{20}$ heterocyclyl.

In some forms, the compounds of Formula I have the formula:

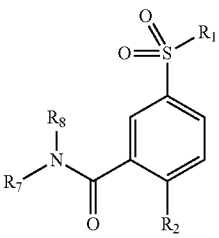

Formula V wherein, $R_7$ and $R_8$ are independently hydrogen, substituted alkyl, unsubstituted alkyl, substituted alkenyl, unsubstituted alkenyl, substituted alkynyl, unsubstituted alkynyl, substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, or $R_7$ and $R_8$ combine to form a substituted $C_3$-$C_{20}$ heterocyclyl, or unsubstituted $C_3$-$C_{20}$ heterocyclyl.

In some forms of Formula V, at least one of $R_7$ and $R_8$ is not hydrogen.

In some forms, the compounds of Formula I have the formula:

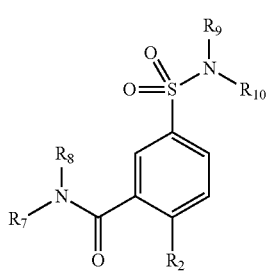

Formula VI wherein, $R_9$ and $R_{10}$ are independently hydrogen, substituted alkyl, unsubstituted alkyl, substituted alkenyl, unsubstituted alkenyl, substituted alkynyl, unsubstituted alkynyl, substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted aralkyl, unsubstituted aralkyl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, or $R_9$ and $R_{10}$ combine to form a substituted $C_3$-$C_{20}$ heterocyclyl, or unsubstituted $C_3$-$C_{20}$ heterocyclyl.

In some forms of Formula VI, at least one of $R_7$ and $R_8$ is not hydrogen.

In some forms of Formula VI, at least one of $R_9$ and $R_{10}$ is not hydrogen.

In some forms of Formula VI $R_7$ and $R_8$ are independently hydrogen, 5-methylthiazol-2-yl, thiazol-2yl, 5-methyl-1,3,4-thiadiazol-2yl, 5-methyl-1H-1,2,4-triazol-3-yl, benzo[d]thiazol-2yl, 4-methoxy-1,3-benzothiazol-2-yl, 5-methoxy-1,3-benzothiazol-2-yl, 6-methoxy-1,3-benzothiazol-2-yl, pyridin-3-yl, pyridine-4-yl, phenyl, 2-methylphenyl, 4-methylphenyl, 2-fluorophenyl, 3-fluorophenyl, 2-chlorophneyl, 4-bromophenyl, cyclohexyl, methyl, or $R_7$ and $R_8$ combine to form morpholin-1-yl.

In some forms of Formula VI $R_9$ and $R_{10}$ are independently hydrogen, methyl, ethyl, phenyl, benzyl, or $R_9$ and $R_{10}$ combine to form pyrrolidin-1-yl, piperidin-1-yl, morpholin-1-yl, or piperazin-1-yl.

In some forms of Formula VI, $R_2$ is hydrogen, pyrrolidine-1-yl, piperidin-1-yl, azetidin-1-yl, piperazin-1-yl, N,N-dimethylamine, N,N-diethylamine, or cyclopentyl.

In some forms, the compounds of Formula VI have the formula:

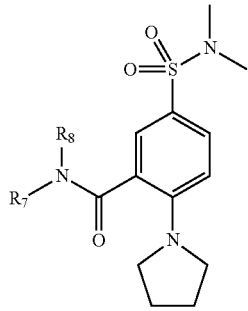

Formula VII

In some forms of Formula VII $R_7$ and $R_8$ are independently hydrogen, 5-methylthiazol-2-yl, thiazol-2yl, 5-methyl-1,3,4-thiadiazol-2yl, 5-methyl-1H-1,2,4-triazol-3-yl, benzo[d]thiazol-2yl, 4-methoxy-1,3-benzothiazol-2-yl, 5-methoxy-1,3-benzothiazol-2-yl, 6-methoxy-1,3-benzothiazol-2-yl, pyridin-3-yl, pyridine-4-yl, phenyl, 2-methylphenyl, 4-methylphenyl, 2-fluorophenyl, 3-fluorophenyl, 2-chlorophneyl, 4-bromophenyl, cyclohexyl, methyl, or $R_7$ and $R_8$ combine to form morpholin-1-yl.

In some forms, the compounds of formula VI have the formula:

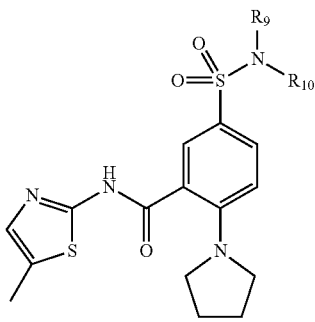

Formula VIII

In some forms of Formula VIII $R_9$ and $R_{10}$ are independently hydrogen, methyl, ethyl, phenyl, benzyl, or $R_9$ and $R_{10}$ combine to form pyrrolidin-1-yl, piperidin-1-yl, morpholin-1-yl, or piperazin-1-yl.

In some forms of Formula VI, the compounds have the formula:

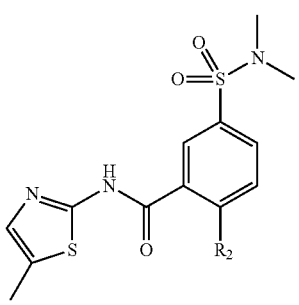

Formula IX

In some forms of Formula IX, $R_2$ is hydrogen, pyrrolidin-1-yl, piperidin-1-yl, azetidin-1-yl, piperazin-1-yl, N,N-dimethylamine, N,N-diethylamine, or cyclopentyl.

In some embodiments, the therapeutic agent is NGI-1, or 5-(dimethylsulfamoyl)-N-(5-methyl-1,3-thiazol-2-yl)-2-(pyrrolidin-1-yl)benzamide.

NGI-1, chemical name ML414, or 5-(dimethylsulfamoyl)-N-(5-methyl-1,3-thiazol-2-yl)-2-(pyrrolidin-1-yl)benzamide is shown in Formula X. NGI-1 targets oligosaccharyltransferase (OST), a hetero-oligomeric enzyme that exists in multiple isoforms and transfers oligosaccharides to recipient proteins. In non-small-cell lung cancer cells, NGI-1 blocks cell-surface localization and signaling of the epidermal growth factor receptor (EGFR) glycoprotein, but selectively arrests proliferation in only those cell lines that are dependent on EGFR (or fibroblast growth factor, FGFR) for survival (Lopez-Sambrooks, et al., *Nat Chem Biol.* 12(12):1023-1030 (2016)).

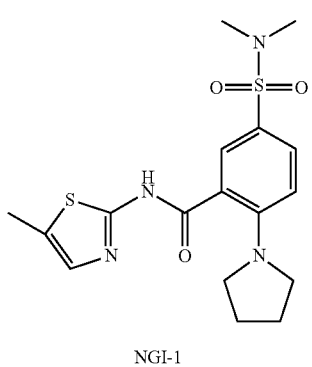

Formula X

NGI-1

In some embodiments, the active agent such as NGI-1 is complexed with polyethylenimine (PEI), followed by encapsulation with poly(D,L-lactide)-poly(ethylene glycol) via nanoprecipitation. In some embodiments, the nanoparticle formulation is injected into animals for delivering the inhibitor to target tissues, preferably inhibiting oligosaccharyltransferase.

In some embodiments, NGI-1 blocks a substantial amount of N-linked glycans to target molecules such as EGFR. For example, NGI-1 can block 10%, 20%, 30%, 40%, 50%, 60%, 70%, 80%, 90%, or more than 90% of N-linked glycans are absence from any protein of interest. In some embodiments, NGI-1 blocks a substantial amount of target molecules such as RTKs to cell surface, for example, 10%, 20%, 30%, 40%, 50%, 60%, 70%, 80%, 90%, or more than 90% of the RTKs are prevented from reaching cell surface of tumor cells.

In some embodiments, the therapeutic agents are functional derivatives of NGI-1 that exhibit one or more biological effects of NGI-1 against tumor cells. Exemplary derivatives include modifications to the amine component of the sulfonamide functionality, the pyrrolidine moiety, and/or the methylaminothiazole group. For example, morpholine can an acceptable surrogate for the dimethylamine component of the sulfonamide; and the pyrrolidine group (blue) can be replaced with various alkyl, cycloalkyl, and amine groups.

Diagnostic Agents

Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

Exemplary diagnostic agents include paramagnetic molecules, fluorescent compounds, magnetic molecules, and radionuclides, x-ray imaging agents, and contrast agents.

These agents can be dispersed in the particle or be covalently attached to one or more of the polymeric components of the particle.

B. Formulations

Pharmaceutical compositions can be for administration by parenteral (intramuscular, intraperitoneal, intravenous (IV) or subcutaneous injection), orally, or topically to the skin or a mucosal surface. The formulations are designed according to the route of administration and can be formulated in dosage forms appropriate for each route of administration. The compositions are typically administered systemically.

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include sterile water, buffered saline of various buffer content (e.g., Tris HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives. Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, deionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. Examples of non-aqueous solvents or vehicles are propylene glycol, polyethylene glycol, vegetable oils, such as olive oil and corn oil, gelatin, and injectable organic esters such as ethyl oleate The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Buffers are used to control pH of a composition. Preferably, the buffers buffer the composition from a pH of about 4 to a pH of about 7.5.

Rapid escape and protection from the endosomal degradation can been achieved by the inclusion of fusogenic lipids such as 1,2-dioleoyl-sn-glycero-3-phosphoethanolamine (DOPE) in pH-sensitive and cationic liposome delivery systems. DOPE is a helper lipid capable of disrupting the endosomal membrane upon endosomal acidification by the formation of lipid hexagonal phases. Endosomal membrane disruption can release the DNA-based therapeutic and its delivery system into the cytoplasm. Lysosomatropic agents such as monensin and chloroquine, which raise the endosomal pH, block acidification, and thus inhibit lysozyme activity, have also been used to facilitate endosomal release of DNA. Endosomal degradation of DNA-based therapeutics can also be circumvented by the incorporation of viral peptides such as hemagglutinin HA2 and those derived from adenoviruses in their delivery systems. Hemagglutinin $HA_2$ undergoes conformational transition and leads to the destruction of the endosome, thereby facilitating the release of the DNA-based therapeutic. Enhanced rapid endosomal escape and enhanced transfection have also been achieved using fusogenic peptides such as poly(L-lysine) (PLL) and cationic polymers such as polyethylenimine (PEI) and dendrimers.

Active agent(s) and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

III. Methods of Manufacture

The particles are typically formed using an emulsion process, single or double, using an aqueous and a non-aqueous solvent. Typically, the particles contain a minimal amount of the non-aqueous solvent after solvent removal. Preferred methods of preparing these particles are described in the example.

In some embodiments, particles are prepared using emulsion solvent evaporation method. A polymeric material is dissolved in a water immiscible organic solvent and mixed with a drug solution or a combination of drug solutions. The water immiscible organic solvent is preferably a GRAS solvent such as chloroform, dichloromethane, and acyl acetate. The drug can be dissolved in, but is not limited to, one or a plurality of the following: acetone, ethanol, methanol, isopropyl alcohol, acetonitrile and Dimethyl sulfoxide (DMSO). An aqueous solution is then added into the resulting mixture solution to yield emulsion solution by emulsification. The emulsification technique can be, but not limited to, probe sonication or homogenization through a homogenizer.

In another embodiment, particles are prepared using nanoprecipitation methods or microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield particle solution. The agents may be associated with the surface of, encapsulated within, surrounded by, and/or distributed throughout the polymeric matrix of the particles.

In another embodiment, particles are prepared by the self-assembly of the amphiphilic polymers, optionally including hydrophilic and/or hydrophobic polymers, using emulsion solvent evaporation, a single-step nanoprecipitation method, or microfluidic devices.

Optionally, targeting moieties can be incorporated into the particles via: i) conjugation of targeting ligands to the hydrophilic region (e.g. PEG) of polymers prior to particle preparation; and/or ii) incorporation of targeting molecules into particles where the PEG layer on the particle surface can be cleaved in the presence of a chemical or enzyme at tissues of interest to expose the targeting molecules.

The diameters of the nanoparticles are between about 50 nm and about 500 nm, preferably between about 50 nm and about 350 nm. In some embodiments, the diameters of the nanoparticles are about 100 nm. The zeta potential of the nanoparticles ranges between about −50 mV and about +50 mV, preferably between about −25 mV and +25 mV, most preferably between about −10 mV and about +10 my.

Methods for making the compositions including one or more therapeutic agents for enhanced in vivo delivery are provided. The methods generally include polymer synthesis, particle preparation including complexation of one or more polymers and one or more active agents, and encapsulation of the compositions.

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization. In most case they can be purchased from commercial sources.

In some embodiments an amphiphilic polymer is synthesized starting from a hydrophobic polymer terminated with a first reactive coupling group and a hydrophilic polymer terminated with a second reactive coupling group capable of reacting with the first reactive coupling group to form a covalent bond. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In preferred embodiments a hydrophobic polymer terminated with an amine or an amine-reactive linking group is coupled to a hydrophilic polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer terminated with a primary amine, such as a PEG-$NH_2$ to form an amphiphilic PLGA-b-PEG block copolymer.

In some embodiments, a conjugate of an amphiphilic polymer with a targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a targeting moiety having a reactive group that is complimentary to the first reactive group to form a covalent bond between the hydrophilic polymer and the targeting moiety. The protective group can then be removed to provide a second reactive coupling group, for example to allow coupling of a hydrophobic polymer block to the conjugate of the hydrophilic polymer with the targeting moiety. A hydrophobic polymer terminated with a reactive coupling group complimentary to the second reactive coupling group can then be covalently coupled to form the conjugate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments, a conjugate is formed having a moiety conjugated to both ends of the amphiphilic polymer. For example, an amphiphilic polymer having a hydrophobic polymer block and a hydrophilic polymer block may have targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a targeting moiety having a reactive coupling group complimentary to the second reactive coupling group, thereby forming a conjugate of the hydrophilic polymer to the targeting moiety. The first protective group and the second protective group can be removed to yield a pair of complimentary reactive coupling groups that can be reacted to covalently link the hydrophobic polymer block to the hydrophilic polymer block.

A. Emulsion

In some embodiments, particles are prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution.

In some embodiments the polymer solution contains one or more polymer conjugates as described above. The polymer solution can contain a first amphiphilic polymer conjugate having a hydrophobic polymer block, a hydrophilic polymer block, and a targeting moiety conjugated to the hydrophilic end. In preferred embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the targeting moieties can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer. The plaque-targeted peptides or fluorophores or drugs may be associated with the surface of, encapsulated within, surrounded by, and/or distributed throughout the polymeric matrix of this inventive particle.

In another embodiment, particles are prepared using nanoprecipitation methods or microfluidic devices. A polymeric material is mixed with a drug or drug combinations in a water miscible organic solvent.

B. Microfluidics

Methods of making particles using microfluidics are known in the art. Suitable methods include those described in U.S. Patent Application Publication No. 2010/0022680 A1 by Karnik et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the particles having the desired size and density of moieties on the surface. By varying the pressure and flow rate in the inlet channels and the nature and composition of the fluid sources particles can be produced having reproducible size and structure.

C. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

D. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

IV. Methods of Use

Methods of using the compositions are provided, particularly for treating cancer. The methods typically include administering a subject in a need thereof an effective amount of a composition including a therapeutic agent in complexation with a cationic polymer that is further encapsulated in one or more amphiphilic polymers, preferably diblock copolymer of a polyalkylene oxide and a polyester, e.g., poly(D, L-lactide)-poly(ethylene glycol) (PLA-PEG).

In some embodiments, the composition reduces, or inhibits enzymatic activity of the oligosaccharyltransferase (OST) enzyme complex in tumor cells. In the most preferred embodiments, methods of using the compositions lead to direct or indirect inhibition, preferably partial inhibition, of N-glycosylation, and/or cell-surface transportation of one or more receptor tyrosine kinases (RTKs) on tumor cells. Thus, methods include administering a subject in a need thereof an effective amount of the composition to reduce, or inhibit enzymatic activity of the oligosaccharyltransferase (OST) enzyme complex in tumor cells.

In some embodiments, the composition reduces, inhibits, or disrupts glycosylation of target molecules such as EGFR by 5%, 10%, 20%, 30%, 40%, 50%, 60%, 70%, 80%, 90%, or more than 90%. In some embodiments, the composition reduces, or inhibits the transport of target molecules such as RTKs to cell surface, for example, 10%, 20%, 30%, 40%, 50%, 60%, 70%, 80%, 90%, or more than 90% of the RTKs are prevented from reaching cell surface of tumor cells. Thus, methods include administering a subject in a need thereof an effective amount of the composition to reduce, or inhibit glycosylation of one or more receptor tyrosine kinases (RTKs) on tumor cells, preferably one or more EGFR family members, FGFR family members, or combinations thereof.

The compositions can be used to reduce or inhibit cell signaling or downstream effector function(s) of one or more receptor tyrosine kinases (RTKs) on tumor cells. Exemplary downstream effector functions include phosphorylation, for example, reductions in one or more phosphorylation sites of EGFR (Y1068), Akt (T308), p70 S6K (T421/424), Src (Y419), and CREB (S133). Thus, methods include administering to a subject in a need thereof an effective amount of the composition to reduce or inhibit phosphorylation of one or more receptor tyrosine kinases (RTKs) on tumor cells, preferably one or more EGFR family members, FGFR family members, or combinations thereof.

The compositions can reduce or inhibit proliferation of tumor cells, cell-cycle arrest, and/or induce senescence in tumor cells, particularly of RTK-dependent lung cancer and brain cancer. In some embodiments, the compositions lead to direct, and/or indirect reduction of tumor cell proliferation by 5%, 10%, 20%, 30%, 40%, 50%, 60%, 70%, 80%, 90%, or more than 90%. In some embodiments, the compositions lead to direct, and/or indirect increase in G1 arrest by 5%, 10%, 20%, 30%, 40%, 50%, 60%, 70%, 80%, 90%, or more than 90%. In further embodiments, the compositions lead to direct, and/or indirect reduction in cyclin D1, and/or increase in protein levels of p21. In some embodiments, the compositions lead to direct, and/or indirect induction of senescence in 5%, 10%, 20%, 30%, 40%, 50%, 60%, 70%, 80%, 90%, or more than 90% of total tumor cells. Thus, methods include administering a subject in a need thereof an effective amount of the composition to reduce or inhibit proliferation, cell-cycle arrest, and/or induce senescence in tumor cells.

A. Methods of Administration

The compositions can be administered by a number of routes including, but not limited to, intravenous, intraperitoneal, intramuscular, transdermal, subcutaneous, topical, sublingual, rectal, intranasal, pulmonary, and other suitable means. In some cases it may be possible to administer orally. Such administration routes and appropriate formulations are generally known to those of skill in the art.

The administration may be localized (i.e., to a particular region, physiological system, tissue, organ, or cell type) or systemic, depending on the condition being treated. Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intraretinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

The formulation can be administered in a single dose or in multiple doses. Certain factors may influence the dosage required to effectively treat a subject, including but not limited to the severity of the disease or disorder, previous treatments, the general health and/or age of the subject, and other diseases present. It will also be appreciated that the effective dosage of the composition used for treatment may increase or decrease over the course of a particular treatment. Changes in dosage may result and become apparent from the results of diagnostic assays.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual polynucleotides, and can generally be estimated based on EC50s found to be effective in vitro and in vivo animal models.

Dosage levels on the order of about 1 mg/kg to 100 mg/kg of body weight per administration are useful in the treatment of a disease. In preferred embodiments, the dosage levels are about 10 mg/kg-50 mg/kg of body weight per administration. One skilled in the art can also readily determine an appropriate dosage regimen for administering the polynucleotides to a given subject. For example, the formulation can be administered to the subject once, e.g., as a single injection, infusion or bolus. Alternatively, the formulation can be administered once or twice daily to a subject for a period of from about three to about twenty-eight days, or from about seven to about ten days.

B. Diseases or Disorders to be Treated

The compositions can also be used for complexing, and/or encapsulating any active agent(s) for treating any diseases, disorders and injuries. In general, the compositions and methods of treatment thereof are useful in the context of cancer, including tumor therapy. The compositions can also be used for treatment of other diseases, disorders and injury including neurodegenerative diseases such as Parkinson's Alzheimer's, Huntington's, etc.; inflammatory diseases, including, but not limited to ulcerative colitis, Crohn's disease, and rheumatoid arthritis; autoimmune diseases systemic lupus erythematosus, insulin dependent diabetes (Type I), juvenile arthritis, etc.

The particles can be designed, for example, for release in the tumor microenvironment or within a tumor cells, or in an immune response microenvironment or within an immune cell. Suitable methods can include administering a subject an effective amount of particles containing a therapeutic agent to reduce or alleviate one or more symptoms of the cancer. The effect of the particles on the cancer can be direct or indirect. The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

In some embodiments, the subject to be treated is a human. All the methods described can include the step of identifying and selecting a subject in need of treatment, or a subject who would benefit from administration with the compositions.

1. Cancers to be Treated

The compositions and methods of treatment thereof are generally suited for treatment of abnormal cellular proliferation such as cancer, for example, lung adenocarcinomas. Mutation of the EGFR kinase domain (KD) is present in approximately 10% of lung adenocarcinomas in western populations. Thus, in some embodiments, the compositions and methods are for treating cancers directly, or indirectly associated with genetic mutations, and/or cellular state that increase receptor tyrosine kinase activation. In further embodiments, the compositions and methods are for treating cancers directly, or indirectly associated with aberrations in one or more receptor tyrosine kinases including mutations of the EGFR kinase domain.

The compositions and methods described herein are useful for treating, or alleviating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The compositions are particularly effective in treating carcinomas. Sarcomas, which arise less frequently, are derived from mesodermal connective tissues such as bone, fat, and cartilage. The leukemias and lymphomas are malignant tumors of hematopoietic ceils of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colorectal, esophageal, kidney, liver, lung, nasopharangeal, pancreatic, prostate, skin, stomach, and uterine. In some embodiments, the compositions are used to treat multiple cancer types concurrently. The compositions can also be used to treat metastases or tumors at multiple locations.

Exemplary tumor cells include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. Cancers that can be prevented, treated or otherwise diminished by the compositions include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In some embodiments, the cancers are characterized as being triple negative breast cancer, or having one or more KRAS-mutations, EGFR mutations, ALK mutations, RB1 mutations, HIF mutations, KEAP mutations, NRF mutations, or other metabolic-related mutations, or combinations thereof.

The experiments below show that NGI-1 partially reduces glycosylation of most RTKs, in some instances also affects RTK stability, and enhances radiosensitivity of glioma cells that have upregulated ErbB family RTK signaling. NGI-1 also enhances the anti-proliferative effects of cytotoxic chemotherapy indicating that a global reduction in RTK signaling combines favorably with standard anti-tumor therapeutic approaches. Thus, in some embodiments, the cancer cells to be treated are characterized by increase receptor tyrosine kinase (RTK) activation, e.g., ErbB family RTK signaling. The composition can be administered to a subject in an effective amount to disrupt the function of one, or preferably multiple RTKs, and in some embodiments enhance the accumulation of DNA damage, reduce clongenic survival of cancer cells, or a combination thereof. The cancer can be a glioma. As discussed in more detail below, in some embodiments, the treatment is combined with cytotoxic chemotherapy, radiotherapy, or a combination thereof. In some embodiments, the cancer cells are not characterized by one or more of PTEN mutation, NF1 mutation, or FGFR3-TACC3 fusion.

The experiments below also show that NGI-1 re-sensitizes EGFR mutant non-small cell lung carcinoma (NSCLC) to tyrosine kinase inhibitors (TKIs). In some embodiments, the cancer cells to be treated are characterized by mutation(s) in a receptor tyrosine kinase, particularly mutation(s) that lead the cancer being resistant to TKI therapy. The receptor tyrosine kinase can be, for example, a epidermal growth factor receptor (EGFR), platelet-derived growth factor receptor (PDGFR), vascular endothelial growth factor receptor (VEGFR), MET (HGFR), or an insulin receptor (InsR) family, Src family, or Abl family protein. In particularly preferred embodiments, the cancer cells to be treated are characterized by mutation(s) in an EFGR. In some embodiments, the cancer to be treated is resistant to TKI therapy. The cancer can be NSCLC. The composition can be administered in an effective amount to increase the sensitivity of the cancer cells to TKI therapy. Thus, in some embodiments, the treatment includes administration or one or more tyrosine kinase inhibitors.

The methods and compounds as described herein are useful for both prophylactic and therapeutic treatment. Therapeutic treatment involves administering to a subject a therapeutically effective amount of the compositions or pharmaceutically acceptable salts thereof as described after cancer is diagnosed.

In further embodiments, the compositions are used for prophylactic use i.e. prevention, delay in onset, diminution, eradication, or delay in exacerbation of signs or symptoms after onset, and prevention of relapse. For prophylactic use, a therapeutically effective amount of the compounds and compositions or pharmaceutically acceptable salts thereof as described are administered to a subject prior to onset (e.g., before clear signs of cancer), during early onset (e.g., upon initial signs and symptoms of cancer), or after an established development of cancer. Prophylactic administration can occur for several days to years prior to the manifestation of symptoms. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers.

2. Neurodegenerative Diseases

The compositions and methods can also be used to delivery active agents for the treatment of a neurological or neurodegenerative disease or disorder or central nervous system disorder. The methods typically include administering the subject an effective amount of the composition to increase cognition or reduce a decline in cognition, increase a cognitive function or reduce a decline in a cognitive function, increase memory or reduce a decline in memory, increase the ability or capacity to learn or reduce a decline in the ability or capacity to learn, or a combination thereof.

Neurodegeneration refers to the progressive loss of structure or function of neurons, including death of neurons. For example, the compositions and methods can be used to treat subjects with a disease or disorder, such as Parkinson's Disease (PD) and PD-related disorders, Huntington's Disease (HD), Amyotrophic Lateral Sclerosis (ALS), Alzheimer's Disease (AD) and other dementias, Prion Diseases such as Creutzfeldt-Jakob Disease, Corticobasal Degeneration, Frontotemporal Dementia, HIV-Related Cognitive Impairment, Mild Cognitive Impairment, Motor Neuron Diseases (MND), Spinocerebellar Ataxia (SCA), Spinal Muscular Atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, Monomelic Amyotrophy, Multiple System Atrophy, Multiple System Atrophy With Orthostatic Hypotension (Shy-Drager Syndrome), Multiple Sclerosis (MS), Neurodegeneration with Brain Iron Accumulation, Opsoclonus Myoclonus, Posterior Cortical Atrophy, Primary Progressive Aphasia, Progressive Supranuclear Palsy, Vascular Dementia, Progressive Multifocal Leukoencephalopathy, Dementia with Lewy Bodies (DLB), Lacunar syndromes, Hydrocephalus, Wernicke-Korsakoff's syndrome, post-encephalitic dementia, cancer and chemotherapy-associated cognitive impairment and dementia, and depression-induced dementia and pseudodementia.

In some embodiments, the subject has a central nervous system disorder or is in need of neuroprotection. Exemplary conditions and/or subjects include, but are not limited to, subjects having had, subjects with, or subjects likely to develop or suffer from a stroke, a traumatic brain injury, a spinal cord injury, Post-Traumatic Stress syndrome, or a combination thereof.

In some embodiments, the compositions and methods are administered to a subject in need thereof in an effective amount to reduce, or prevent one or more molecular or clinical symptoms of a neurodegenerative disease, or one or more mechanisms that cause neurodegeneration. Neurodegeneration, and diseases and disorders thereof, can be caused by a genetic mutation or mutations; protein misfolding; intracellular mechanisms such as dysregulated protein degradation pathways, membrane damage, mitochondrial dysfunction, or defects in axonal transport; defects in programmed cell death mechanisms including apoptosis, autophagy, cytoplasmic cell death; and combinations thereof. More specific mechanisms common to neurodegenerative disorders include, for example, oxidative stress, mitochondrial dysfunction, excitotoxicity, inflammatory changes, iron accumulation, and/or protein aggregation.

In some embodiments, the subject has been medically diagnosed as having a neurodegenerative disease or a condition in need of neuroprotection by exhibiting clinical (e.g., physical) symptoms of the disease. Therefore, in some embodiments, the compounds or compositions herein are administered prior to a clinical diagnosis of a disease or condition. In some embodiments, a genetic test indicates that the subject has one or more genetic mutations associated with a neurodegenerative disease or central nervous system disorder.

Neurodegenerative diseases are typically more common in aged individuals.

Active agents for the treatment of neurodegenerative diseases are well known in the art and can vary based on the symptoms and disease to be treated. For example, conventional treatment for Parkinson's disease can include levodopa (usually combined with a dopa decarboxylase inhibitor or COMT inhibitor), a dopamine agonist, or an MAO-B inhibitor.

Treatment for Huntington's disease can include a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

Riluzole (RILUTEK®) (2-amino-6-(trifluoromethoxy) benzothiazole), an antiexcitotoxin, has yielded improved survival time in subjects with ALS. Other medications, most used off-label, and interventions can reduce symptoms due to ALS. Some treatments improve quality of life and a few appear to extend life. Common ALS-related therapies are reviewed in Gordon, *Aging and Disease*, 4(5):295-310 (2013), see, e.g., Table 1 therein. A number of other agents have been tested in one or more clinical trials with efficacies ranging from non-efficacious to promising. Exemplary agents are reviewed in Carlesi, et al., *Archives Italiennes de Biologie*, 149:151-167 (2011). For example, therapies may include an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f)oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

Treatment for Alzheimer's Disease can include, for example, an acetylcholinesterase inhibitor such as tacrine, rivastigmine, galantamine or donepezil; an NMDA receptor antagonist such as memantine; or an antipsychotic drug.

Treatment for Dementia with Lewy Bodies can include, for example, acetylcholinesterase inhibitors such as tacrine, rivastigmine, galantamine or donepezil; the N-methyl d-aspartate receptor antagonist memantine; dopaminergic therapy, for example, levodopa or selegiline; antipsychotics such as olanzapine or clozapine; REM disorder therapies such as clonazepam, melatonin, or quetiapine; anti-depression and antianxiety therapies such as selective serotonin reuptake inhibitors (citalopram, escitalopram, sertraline, paroxetine, etc.) or serotonin and noradrenaline reuptake inhibitors (venlafaxine, mirtazapine, and bupropion) (see, e.g., Macijauskiene, et al., *Medicina (Kaunas)*, 48(1):1-8 (2012)).

Exemplary neuroprotective agents are also known in the art in include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin.

Other common active agents for treating neurological dysfunction include amantadine and anticholinergics for treating motor symptoms, clozapine for treating psychosis, cholinesterase inhibitors for treating dementia, and modafinil for treating daytime sleepiness.

3. Autoimmune or Inflammatory Disease

In some embodiments, the compositions can also be used for treatment of autoimmune or inflammatory disease or disorder. Exemplary autoimmune or inflammatory disease or disorder include rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Anti-inflammatory agents include steroidal and non-steroidal drugs. Suitable steroidal active agents include glucocorticoids, progestins, mineralocorticoids, and corticosteroids. Other exemplary anti-inflammatory agents include triamcinolone acetonide, fluocinolone acetonide, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drug include ketorolac, nepafenac, and diclofenac.

4. Infections

In some embodiments, the compositions and methods can also be used to deliver antimicrobial agents for the treatment of microbial infections such as bacterial, viral, fungal, and parasitic infections C. Combination Therapies In some embodiments, the disclosed particle formulations are administered to a subject in need thereof with a second or more active agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft.

The additional therapeutic agents can be selected based on the disease or disorder to be treated and include, but are not limited to, radiotherapy, chemotherapeutic agents, antibodies, antibiotics, antivirals, steroidal and non-steroidal anti-inflammatories, conventional immunotherapeutic agents, immunosuppressants, cytokines, chemokines and/or growth factors.

1. Radiotherapy

In some embodiments, the compositions are used in combination with radiation therapy. Radiation therapy (a.k.a. radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification.

In some embodiments, NGI-1 or a compound structurally related thereto including, but not limited to the formulae disclosed herein, can be used to increase radiosensitivity for a malignant or non-malignant condition.

Radiation therapy works by damaging the DNA of dividing cells, e.g., cancer cells. This DNA damage is caused by one of two types of energy, photon or charged particle. This damage is either direct or indirect. Indirect ionization happens as a result of the ionization of water, forming free radicals, notably hydroxyl radicals, which then damage the DNA. For example, most of the radiation effect caused by photon therapy is through free radicals. One of the major limitations of photon radiotherapy is that the cells of solid tumors become deficient in oxygen, and tumor cells in a hypoxic environment may be as much as 2 to 3 times more resistant to radiation damage than those in a normal oxygen environment.

Direct damage to cancer cell DNA occurs through high-LET (linear energy transfer) charged particles such as proton, boron, carbon or neon ions. This damage is independent of tumor oxygen supply because these particles act mostly via direct energy transfer usually causing double-stranded DNA breaks. Due to their relatively large mass, protons and other charged particles have little lateral side scatter in the tissue; the beam does not broaden much, stays focused on the tumor shape and delivers small dose side-effects to surrounding tissue. The amount of radiation used in photon radiation therapy is measured in Gray (Gy), and varies depending on the type and stage of cancer being treated. For curative cases, the typical dose for a solid epithelial tumor ranges from 60 to 80 Gy, while lymphomas are treated with 20 to 40 Gy. Post-operative (adjuvant) doses are typically around 45-60 Gy in 1.8-2 Gy fractions (for breast, head, and neck cancers). Many other factors are considered by radiation oncologists when selecting a dose, including whether the patient is receiving chemotherapy, patient co-morbidities, whether radiation therapy is being administered before or after surgery, and the degree of success of surgery.

The response of a cancer to radiation is described by its radiosensitivity. Highly radiosensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radioresistant, that is, much higher doses are required to produce a radical cure than may be safe in clinical practice. Renal cell cancer and melanoma are generally considered to be radioresistant.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radiotherapy. A third technique is to enhance the radiosensitivity of the cancer by giving certain drugs during a course of radiotherapy. It is believed that NGI-1 and compounds structurally related thereto including, but not limited to the formulae disclosed herein can serve this third function. In these embodiments, the NGI-1 or a compound structurally related thereto including, but not limited to, the formulae disclosed herein may increase the cell's sensitivity to the radiotherapy, for example, by at least 10%, 15%, 20%, 25%, 30%, 35%, 40%, 45%, 50%. Moreover, the NGI-1 compound can be combined with one or more additional radiosensitizers. Examples of known radiosensitizers include cisplatin, gemcitabine, 5-fluorouracil, pentoxifylline, vinorelbine, PARP inhibitors, histone deacetylase inhibitors, and proteasome inhibitors.

D. Chemotherapeutics

Numerous chemotherapeutics, especially antineoplastic drugs, are available for combination with the disclosed compositions. The majority of chemotherapeutic drugs can be divided into alkylating agents, antimetabolites, anthracyclines, plant alkaloids, topoisomerase inhibitors, monoclonal antibodies, and other antitumor agents.

In some embodiments, the antineoplastic drug damages DNA or interferes with DNA repair. In some embodiments, NGI-1 or a compound structurally related thereto including, but not limited to, the formulae disclosed herein increases the cell's sensitivity to the chemotherapy, for example, by at least 10%, 15%, 20%, 25%, 30%, 35%, 40%, 45%, 50%.

Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas. In some embodiments, the antineoplastic drug is a PARP inhibitor, which inhibits a step in base excision repair of DNA damage. In some embodiments, the antineoplastic drug is a histone deacetylase inhibitor, which suppresses DNA repair at the transcriptional level and disrupt chromatin structure. In some embodiments, the antineoplastic drug is a proteasome inhibitor, which suppresses DNA repair by disruption of ubiquitin metabolism in the cell. Ubiquitin is a signaling molecule that regulates DNA repair. In some embodiments, the antineoplastic drug is a kinase inhibitor, which suppresses DNA repair by altering DNA damage response signaling pathways.

In other embodiments, the antineoplastic drug complements compound by targeting a different activity in the cancer cell. In these embodiments, the antineoplastic drug does not inhibit DNA repair or damage DNA.

Examples of antineoplastic drugs that can be combined with the disclosed compounds include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), some antimitotics, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide).

In some embodiments, the chemotherapeutic agent is a TKI. Exemplary tyrosine kinase inhibitors include those that have been FDA approved for the treatment of cancer, such as imatinib, gefitinib, nilotinib, sorafenib, sunitinib, dasatinib, lapatinib, pazopanib, crizotinib, ruxolitinib, vandetanib, axitinib, bosutinib, afatinib, erlotinib, ceritinib, osimertinib, lenvatinib, alectinib, regorafenib, neratinib, brigatinib. See, e.g., Jiao, et al., *Molecular Cancer*, 201817: 36 (2018) (12 pages), and Jeong, et al., *Curr Probl Cancer*, 37(3): 110-144 (2013) doi: [10.1016/j.currproblcancer.2013.06.001].

E. Controls

The effect of the composition can be compared to a control. Suitable controls are known in the art and include, for example, an untreated subject, or a placebo-treated subject. In some embodiments, an untreated control subject suffers from, the same disease or condition as the treated subject e.g. non-small-cell lung cancer.

V. Kits

Medical kits are also disclosed. The medical kits can include, for example, a dosage supply of the composition. The active agents can be supplied alone (e.g., lyophilized), or in a pharmaceutical composition. The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

The present invention will be further understood from the following non-limiting examples.

EXAMPLES

Example 1: Method of Formulating NGI-1 for Improved In Vivo Delivery

NGI-1 particles were fabricated by complexation of NGI-1 with polyethylenimine (PEI), and then encapsulation into diblock poly(lactic acid)-poly(ethylene glycol) (PLA-PEG) nanoparticles (NPs) using a nanoprecipitation technique.

NGI-1 was dissolved in DMSO at 50 mg/ml.

PEI was dissolved in DMSO at 50 mg/ml.

The NGI-1 and PEI solutions were then mixed at a 6:1 ratio of PEI:drug by weight.

The solution was vortexed for ~10 s and then incubated at room temperature for 15 min.

PLA-PEG (10-5 kDa) was then dissolved in DMSO at 20 mg/ml using water bath sonication.

After the 15 min incubation period, the PEI/NGI-1 solution was then added to the PLA-PEG solution at a 10% ratio of NGI-1:PLA-PEG by weight.

This combined solution was briefly vortexed and then water-bath sonicated to ensure uniform mixing.

The solution was then added dropwise to distilled H2O under vortex at a final ratio of 1:5 organic:aqueous phase.

The resulting suspension was immediately filtered using a 100 k centrifugation filter and subsequently underwent 3× washes using resuspension in deionized water and centrifugation filtration.

After the final wash, the particles were resuspended in deionized water and immediately frozen until use.

Example 2: NGI-1 Disrupts RTK Signaling in Glioblastoma Cells

Baro, et al., "Oligosaccharyltransferase inhibition Reduces Receptor Tyrosine Kinase Activation and Enhances Glioma Radiosensitivity," *Clin Cancer Res.* 2018 Jul. 2. pii: clincanres.0792.2018. doi: 10.1158/1078-0432.CCR-18-0792, and all of the Supplementary Data associated therewith, are specifically incorporated by references herein in their entireties.

Receptor tyrosine kinases (RTK) are transmembrane glycoproteins that regulate downstream signaling involved in cell proliferation and survival. Receptor overexpression or activation caused by mutation is important for the development and progression of many tumors including glioblastoma (GBM), an incurable malignant brain tumor (Xu and Huang, *Cancer Res.*, 70:3857-60 (2010), Casaletto and McClatchey, *Nat Rev Cancer*, 12:387-400 (2012)). RTKs such as ErbB2 and EGFR, as well as the RTK ligand, VEGF, have been successfully targeted in multiple tumor types both as monotherapies or combined with cytotoxic chemotherapy. In head and neck squamous cell carcinoma (HNSCC), EGFR inhibition has also been identified as an effective method for tumor cell radiosensitization (Begg, et al., *Nat Rev Cancer*, 11:239-53 (2011), Mahajan and Mahajan, *Nucleic Acids Res.*, 43:10588-601 (2015), *Cancer*

Res., 5:405-11 (1999)). However, targeting RTKs in glioblastoma has produced limited clinical responses (Rich et al., *J Clin Oncol.*, 22:133-42 (2004), Reardon et al., *J Clin Oncol.*, 24:1253-65 (2006), Wen et al., *Clin Cancer Res.*, 12:4899-907 (2006)) questioning whether specific receptors are effective targets in this tumor type.

Parallel or bypass kinase signaling has been identified as a mechanism for resistance to therapeutics that target specific RTKs. For example, de-repression of PDGFRβ transcription has been implicated as an alternative signaling pathway that promotes acquired resistance to EGFR tyrosine kinase inhibitors in glioblastoma (Akhavan et al., *Cancer Discov.*, 3:534-47 (2013)). The co-expression of EGFR and c-Met has also been shown to rescue survival signaling and counteract EGFR signaling blockade (Qi et al., *Cancer Res.*, 71:1081-91 (2011), Jun et al., *Oncogene*, 31:3039-50 (2012)). In addition, the dependence of downstream signaling on multiple co-expressed RTKs (Stommel et al., *Science*, 318:287-90 (2007), Chinot et al., *N Engl J Med.*, 370:709-22 (2014)), provides a further understanding of the limitations for targeting individual RTKs in GBM and emphasizes the need for therapeutic strategies that disrupt signaling through multiple RTK proteins.

N-linked glycosylation (NLG) is an endoplasmic reticulum (ER) co- and post-translational protein modification that has an important role in the assembly and maturation of cell surface glycoprotein receptors (reviewed in Aebi, *Biochim Biophys Acta.*, 1833:2430-7 (2013)). NLG is a conserved two-phase process in eukaryotic cells. It involves the assembly of an oligosaccharide on a lipid carrier followed by the transfer of the oligosaccharide to asparagine residues within a specific amino acid consensus sequence (NXS/T; where X can be any amino acid other than proline). The sequential assembly of the mature oligosaccharide is initiated on the ER cytoplasmic leaflet, completed in the ER lumen, and requires the activity of multiple enzymes and glycosyltransferases (Freeze, *Nat Rev Genet.*, 7:537-51 (2006)). The glycosylation reaction itself is catalyzed in the ER lumen by the oligosaccharyltransferase (OST), a multisubunit enzyme complex that exists in several isoforms (Kelleher and Gilmore, *Glycobiology*, 16:47R-62R (2006)). The glycosylation pathway therefore represents a potential upstream biosynthetic node for regulating the function of multiple cell surface receptors, including RTKs, and is therefore an attractive target for cancer biology investigations.

NLG is known to be important for the function for several transmembrane receptors that are targets for cancer therapy, including the ErbB family members, VEGFR, and IGF-1R (Contessa at al., *Clin Cancer Res.*, 16:3205-14 (2010), Croci et al., *Cell.*, 156:744-58 (2014), Itkonen and Mills, *PLoS One*, 8:e65016 (2013)). Furthermore, inhibition of NLG with tunicamycin, an inhibitor of dolichyl-phosphate N-acetylglucosamine-phospho-transferase (DPAGT1), or siRNA/shRNA knockdown of MPI, an enzyme required for glycan precursor biosynthesis, blocks RTK function and enhances glioma cell radiosensitivity (Contessa at al., *Cancer Res.*, 68:3803-9 (2008), Cazet at al., *PLoS One*, 9:e110345 (2014)).

A high throughput screening campaign for small molecule inhibitors of NLG identified an aminobenzamidesulfonamide chemical series that disrupts the function of the OST. The lead compound from this group, NGI-1, targets the OST catalytic subunits through a direct and reversible interaction (Lopez-Sambrooks et al., *Nat Chem Biol.*, 12:1023-30 (2016)). Importantly, NGI-1 does not completely abolish all OST activity, producing incomplete inhibition of glycosylation that is associated with low toxicity. Because NGI-1 is believed to alter the glycosylation and function of multiple RTKs the effects of NGI-1 treatment in malignant glioma cells was investigated. The experiments below test combinatorial effects of NGI-1 with both radiation or cytotoxic chemotherapy with a goal of understanding the underlying cellular mechanisms that are affected. Together this work evaluates the potential of OST inhibition as therapeutic strategy for the treatment of malignant glioma.

Materials and Methods

Cell Lines and Pharmacological Inhibitors

In this study, the D54, SKMG3, U251, T98G and 42-MG glioma cell lines were used. The source of D54, SKMG3 and U251 cells has been described previously (Contessa at al., *Clin Cancer Res.*, 16:3205-14 (2010), Lopez et al., *Int J Radiat Oncol Biol Phys.*, 69:214-20 (2007)). The 42-MG and T98G cells were provided by Todd Waldman (Georgetown University) and Dr. Ranjit Bindra (Yale University), respectively. The cells were cultured in DMEM/F12 (D54 and T98G), DMEM (42-MG and U251) or RPMI 1640 (SKMG3)+10% FBS supplemented with penicillin and streptomycin (Gibco, Life Technologies, Grand Island, N.Y., US) in a humidified incubator with 5% $CO_2$, and they were kept in culture no more than 6 months after resuscitation from the original stocks. All cell lines used in the study were authenticated by the American Type Culture Collection (ATCC) STR profiling, other than SKMG3 which does not have a published STR profile but was confirmed to be of human origin and matched no other cell lines in the ATCC or DMSZ databases. *Mycoplasma* cell culture contamination was routinely checked and ruled out using a biochemical test (MycoAlert *Mycoplasma* Detection Kit from Lonza, Rockland, Me. USA). Tunicamycin was purchased from Calbiochem/EMD-millipore (Burlington, Mass., USA). Cetuximab and Erlotinib were purchased at Selleck Chemicals LLC (Houston, Tex., USA). Luciferin was supplied by Promega (Madison, Wis. USA). For in vitro experiments, radiation (XRT) was administered at room temperature using a Precision X-ray 320-kV orthovoltage unit at a dose rate of 2 Gy/45 seconds (PXI X-Ray Systems) with 2 mm aluminum filter. For in vivo studies, radiation was administered at room temperature using a Precision X-ray 250-kV orthovoltage unit at a dose rate of 6.42 Gy/min (PXI X-Ray Systems) with 2 mm aluminum filter. Quality Assurance for both irradiators was performed monthly using a P.T.W. 0.3 $cm^3$ Ionization Chamber calibrated to NIST standards and quarterly dosimetry using thermoluminescent dosimeter (TLD)-based or ferrous sulfate-based dosimeters.

Western Blot Analysis

Western blot analyses were performed as previously described (Baro at al., *Br J Cancer*, 111:1310-8 (2014). The nitrocellulose-bound primary antibodies, were detected with anti-rabbit IgG horseradish peroxidase-linked antibody or anti-mouse IgG horseradish peroxidase-linked antibody (EMD Millipore; Temecula, Calif. USA), and were detected by the enhanced chemoluminescence staining ECL (GE Healthcare-Amersham Pharmacia, Buckinghamshire, U.K.).

Statistical Analysis

Results are expressed as mean±standard error (S.E.) unless otherwise indicated. The Statistical Package for Social Sciences (SPSS, version 20.0) was used for data analysis. Statistically significant differences in between-group comparisons were defined at a significance level of P-value≤0.05 in the Mann-Whitney test.

Results

Molecular studies of glioblastoma tumors have identified increased RTK expression (Cancer Genome Atlas Research N. *Nature.* 455:1061-8 (2008), Dunn et al., *Genes Dev.*, 26:756-84 (2012)). These receptors are highly glycosylated. The effects of a small molecule inhibitor of glycosylation (NGI-1) were tested on RTK glycosylation and activation. SKMG3 and D54 cell lines had high expression and activation levels of ErbB family members including EGFR, ErbB2, and ErbB3. NGI-1 reduced glycosylation, determined by increased protein gel mobility on western blot, as well as phosphorylation of EGFR, ErbB2, and ErbB3. The reduced EGFR phosphorylation was not caused by decreases in EGFR protein levels, contrary to observations with tunicamycin (Contessa at al., Cancer Res., 68:3803-9 (2008)). However, a reduction in ErbB2 protein levels in SKMG3, as well as a reduction of ErbB3 protein levels in both D54 and SKMG3 cell lines were observed.

To further characterize the effect of NGI-1 on these glioma cell lines, the phosphorylation levels of MET, PDGFR and FGFR RTKs were investigated. 42-MG, D54, SKMG3, U251 and T98G cell lines each had a distinct profile of receptor expression and activation. Unlike the ErbB family of RTKs, expression levels did not directly correlate with the phosphorylation of these receptors. Regardless, NGI-1 uniformly reduced phosphorylation of MET in D54, SKMG3, U251, and T98G cells, and phosphorylation of PDGFR in 42-MG, SKMG3, and T98G cells. This reduction of phosphorylation was observed to be independent of the effects of NGI-1 on RTK protein levels. Surprisingly FGFR1 levels were increased by NGI-1, although this was not accompanied by an increase in receptor phosphorylation.

Example 3: NGI-1 Radiosensitizes Gliobastoma Cell Lines with Activated ErbB Receptors Materials and Methods
Radiation Survival and Proliferation Assays Clonogenic survival assays were performed with cells treated in the presence or absence of 10 μM NGI-1 48 hours before radiation and maintained until cells were re-plated. Radiation (XRT) doses of either 0, 2, 4, or 6 Gy were delivered with a Precision X-ray 320-kV orthovoltage unit at a dose rate of 2 Gy/45 seconds (PXI X-Ray Systems). Twenty-four hours following XRT cells were washed, trypsinized, and re-plated in triplicate wells to determine clonogenic survival. Cultures were grown for 14 days, washed once with 1×PBS, and stained with 0.25% crystal violet in 80% methanol. Colonies with >50 cells were counted and clonogenic cell survival differences for each treatment were compared using survival curves generated from the linear quadratic equation using GraphPad Prism7 (GraphPad Software Inc.). Growth rates were determined by CellTiter 96 Non-Radioactive Cell Proliferation Assay (Promega; Madison, Wis., USA) according to the manufacturer's directions. For each experiment one thousand cells were seeded in triplicate wells in 96-wells plates. The following day, cell cultures were treated with NGI-1 (1 μM), Temozolomide (TMZ, 10 μM), Etoposide (VP-16, 0.1 μM) or combinations for 5 days. Absorbance at 540 nm was measured using the spectrophotometric reading (BioTek Synergy 2; Winooski, Vt. USA).

Results

Figures 1A, 1B:
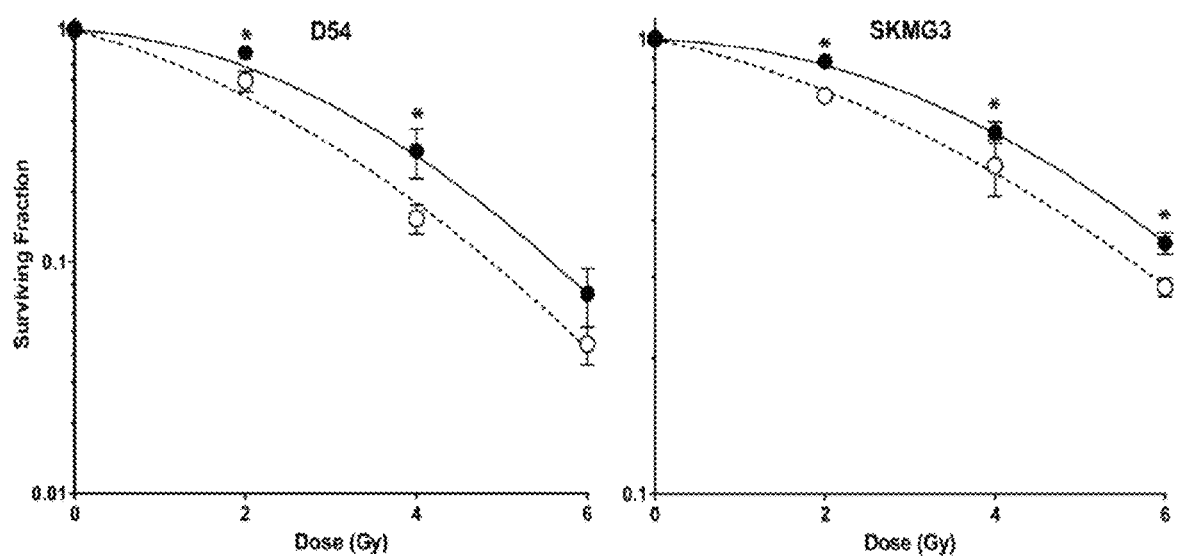
FIGS. 1A-1D line graphs showing the clonogenic survival of D54 (1A), SKMG3 (1B), T98G (1C), and U251 (1D) cells treated with vehicle or 10 μM NGI-1. The results represent data from three independent experiments for each cell line.
Figures 1C, 1D:
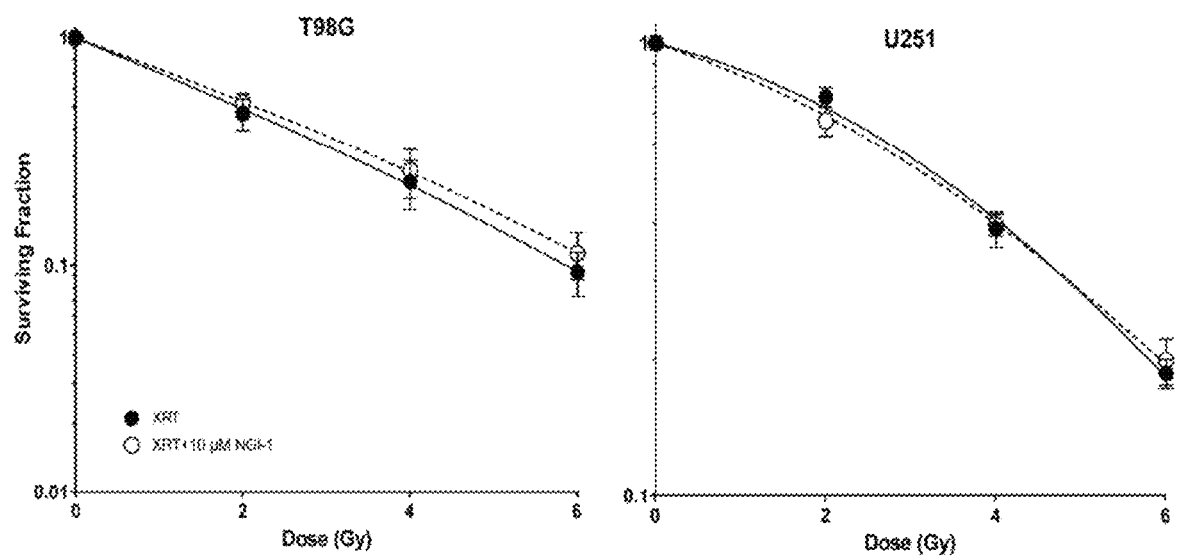
Figure 3A:
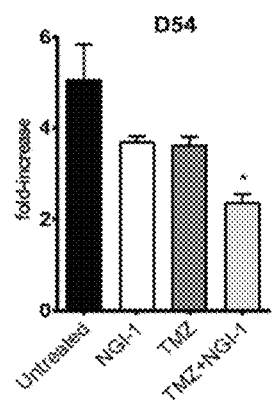
Figure 3C:
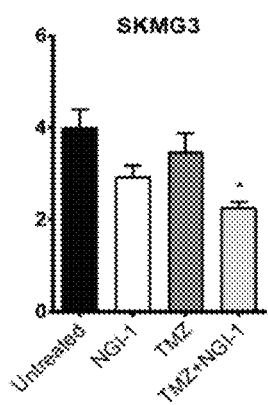
Figure 3E:
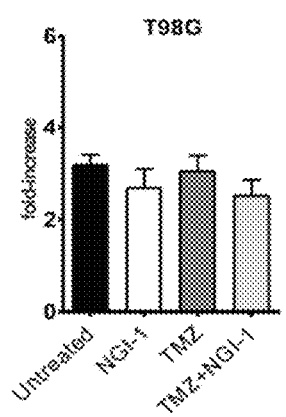
Figure 3G:
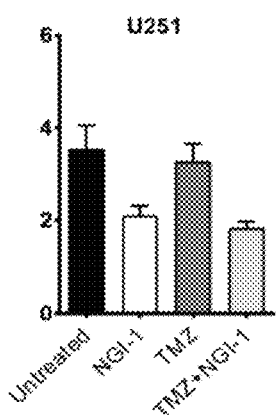
Figure 3B:
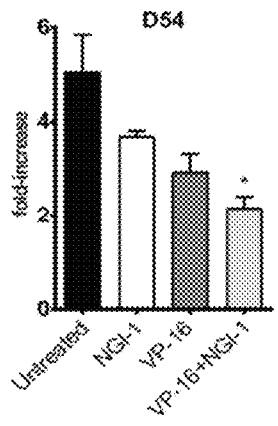
Figure 3D:
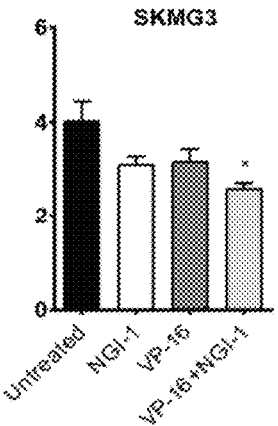
Figure 3F:
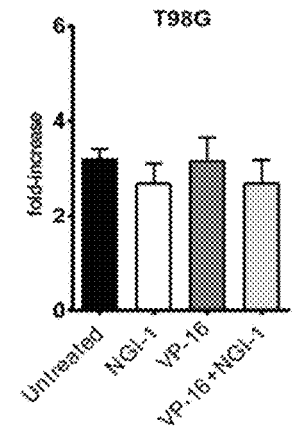
Figure 3H:
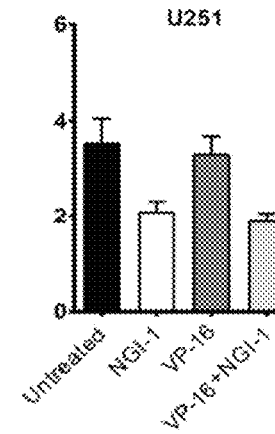
Figure 4A:
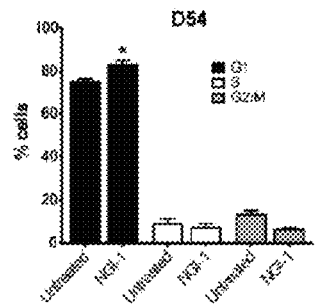
Figure 4B:
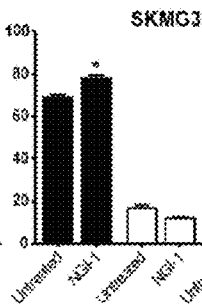
Figure 4C:
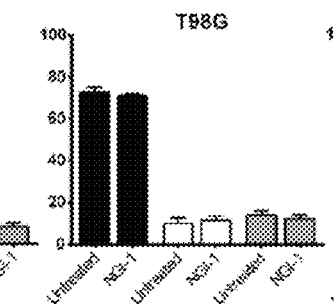
Figure 4D:
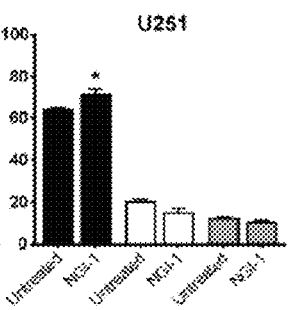
Figure 4E:
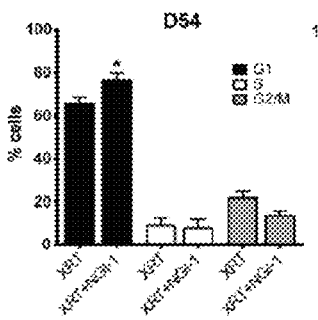
Figure 4F:
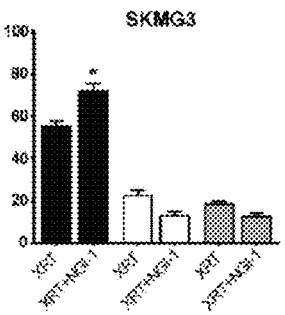
Figure 4G:
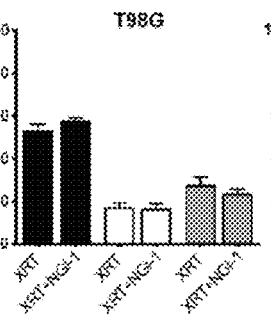
Figure 4H:
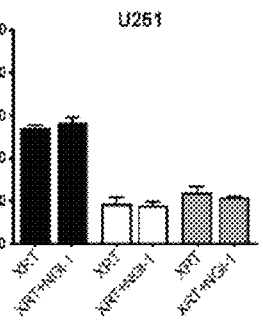
Figure 4I:
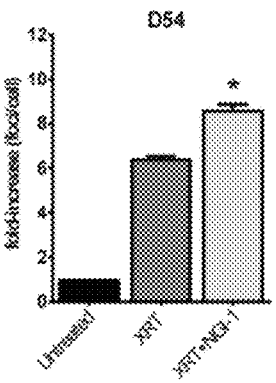
Figure 4J:
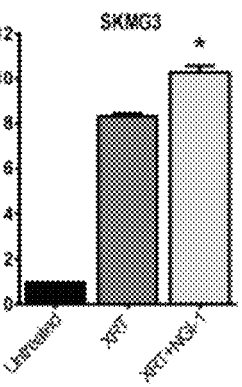
Figure 4K:
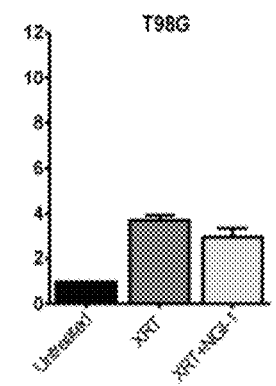
Figure 4L:
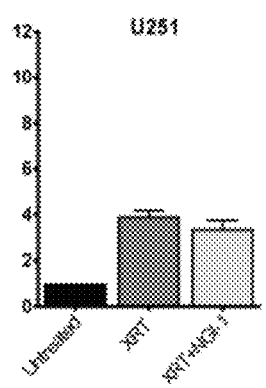

RTK activation protects tumor cells from radiation-induced cell death (Chen and Nirodi, Clin Cancer Res., 13:6555-60 (2007), Schmidt-Ullrich et al., Oncogene, 22:5855-65 (2003)). The effects of NGI-1 on glioma cell radiosensitivity was tested using clonogenic survival analysis (FIG. 1A-1D). D54 and SKMG3 cell lines, both with significant ErbB family RTK activation, were significantly radiosensitized by NGI-1 at each dose tested (FIGS. 1A and 1B; p<0.05). The survival fraction at 2 Gy ($SF_{2Gy}$) was reduced from 69% to 51% for D54 cells and from 87% to 77% for SKMG3 cells. The dose enhancement factors (DEF) at a surviving fraction of 0.4 for D54 and SKMG3 were 1.3 and 1.2, respectively. In contrast, for both T98G and U251 cells the $SF_{2Gy}$ was unaffected by NGI-1 (FIGS. 1C and 1D). The correlation of ErbB family RTK signaling with the radiation response indicates that NGI-1 radiosensitizes glioma cells by disrupting ErbB RTK signaling.

Example 4: NGI-1 Enhances Cytotoxic Chemotherapy in Glioma

Materials and Methods
Immunofluorescence and Cell Cycle Analysis

To determine histone H2AX phosphorylation (γH2AX), cells were cultured on glass cover slips and pre-treated with either vehicle or NGI-1 for 48 hours followed by radiation treatment. Samples were fixed with 4% neutral-buffered formaldehyde, washed (0.1% triton in PBS for 30 minutes) and incubated for 1 hour with protein-blocking solution (PBS containing 10% normal goat-horse serum; Sigma-Aldrich, Saint Louis, Mich., US). Next, the slides were incubated with primary anti-phospho-histone γH2AX S139 (1:500, Millipore-Upstate, Billerica, Mass., US) followed by incubation with secondary antibody Alexa Fluor 555-conjugated goat anti-mouse IgG (1:750, Molecular probes/Invitrogen, Carlsbad, Calif., US), for 1 hour at room temperature. Nuclei were stained using DAPI containing vectashield mounting solution (Vector Labs). Confocal cellular images were captured with an inverted Zeiss LSM 510 Pascal laser confocal microscope (C. Zeiss, Jenna, Germany), using a 63/1.4 plan-apochromat objective. Five randomly selected fields s per slide were analyzed. Cells were counted using the ImageJ program, public domain Java image processing software.

Cell cycle distribution was determined following treatment with vehicle, radiation and/or 10 uM NGI-1. Cells were trypsinized and centrifuged, washed once with ice-cold PBS, fixed with ice-cold 70% ethanol and stored overnight at −20° C. After washing twice with PBS, they were incubated for 30 minutes at room temperature in 200 μL of Guava Cell Cycle Reagent (Guava Technologies). Cytofluorometric acquisitions were performed on a LSRII cytometer (BD Biosciences). First-line analysis was performed with FlowJo software, upon gating of the events characterized by normal forward and side scatter parameters and discrimination of doublets in a FSC-A vs. FSC-H bivariate plot. Approximately 50,000 cells were analyzed per experiment.

Results

To investigate the effects of NGI-1 in combination with cytotoxic chemotherapy, dose response experiments were performed with NGI-1 (FIG. 2A-2D), temozolomide (TMZ) (FIG. 2E-2H, or etoposide (VP-16) (FIG. 2I-2L) to determine the effects on proliferation and to select the appropriate concentrations for this line of experimentation. Glioma cell line proliferation was sensitive to NGI-1. A dose of 1 μM was used for combination treatment experiments. D54, SKMG3, T98G or U251 cells were then treated for 5 days with NGI-1, with or without TMZ or VP-16. For D54 and SKMG3, the combinations of NGI-1 with TMZ or VP-16 further reduced glioma cell proliferation, although these effects were not synergistic (FIG. 3A-3D; p≤0.05, light gray bars). In contrast, NGI-1 treatment did not enhance the anti-proliferative effects of TMZ or VP-16 in T98G or U251 cells (FIG. 3E-3H). This data parallels the observations with radiation clonogenic survival and indicates that blockade of RTK signaling may also enhance the effects of cytotoxic chemotherapy in malignant glioma.

Example 5: NGI-1 Enhances Cell Cycle Arrest and DNA Damage in Glioma

An accumulation of cells in the G1 phase of the cell cycle after NGI-1 treatment in NSCLC is described in (Lopez-Sambrooks et al., Nat Chem Biol., 12:1023-30 (2016)). The effects of NGI-1 on cell cycle distributions were examined after 48 hours of NGI-1 treatment. The results demonstrate that NGI-1 caused a significant G1 arrest in D54 (83% vs. 75%), SKMG3 (78% vs. 69%) and U251 (64% vs. 72%) cells (FIG. 4A-4H, p≤0.05), but no arrest in the T98G cell line. Six hours after 4 Gy, a significant G1 arrest was again observed with NGI-1 treatment for D54 (77% vs. 66%) and SKMG-3 (72% vs. 56%), but not for either the T98G or U251 cells. This data indicates that NGI-1 reduces progression through the cell cycle after radiation therapy and indicates that inhibition of upstream growth factor receptor glycoproteins alters these downstream cell cycle distributions.

To evaluate the effects of NGI-1 on the DNA damage response, time course experiments were performed to determine the kinetics of phospho-γH2AX foci formation in the presence or absence of NGI-1. D54 cells were irradiated with 4 Gy and foci were detected with a S139 phospho-specific antibody at 0 (pre-radiation), 2, 4, 6 and 8 hours. Radiation alone induced a 6.4-fold increase of phospho-γH2AX foci formation followed by a rapid decrease at 4 hours and full resolution of foci by 8 hours. NGI-1 treatment increased phospho-γH2AX foci formation significantly up to 8.6-fold (P=0.03), followed by a similar time frame for foci resolution as radiation alone (FIG. 5).

The induction of phospho-γH2AX foci was quantified at 2 hours in D54, SKMG3, U251 and T98G cell lines irradiated with 4 Gy. NGI-1 increased phospho-γH2AX foci formation (FIG. 4I-4L; p≤0.05) by a factor of 1.3 and 1.2 in D54 and SKMG3 cell lines, respectively, compared to radiation alone (p≤0.05; dark gray bars) consistent with an increase in DNA damage. However, no enhancement of phospho-γH2AX foci formation was observed in either T98G or U251 cells. Together these results indicate that in cells with high levels of cytoprotective RTK signaling, NGI-1 enhances DNA damage which contributes to cell cycle arrest and tumor cell death.

Example 6: NGI-1 Reduces Tumor Growth of Glioblastoma with Activated ErbB Receptors In Vivo Materials and Methods NGI-1 Nanoparticle (NP) Preparation and Evaluation Polyethylene glycol (PEG)-b-Polylactic acid (PLA) nanoparticles were synthesized using diblock polymer (Mw PEG=5 kDa, Mw PLA=10 kDa; Polysciences, Inc. Warrington, Pa., USA) and Polyethyeleneimine (PEI; branched—average Mw~800, average Mn~600; Sigma-Aldrich, USA) using a nanoprecipitation technique, similar to one previously reported (King et al., Mol Cancer Ther., 16:1456-69 (2017)). For control NPs 100 mg of polymer was dissolved in 5 ml DMSO at RT for 2 hours and a 200 ul aliquot was added drop-wise to 1 mL deionized (DI) water under strong vortex to create a NP suspension. These suspensions were immediately diluted 5× with DI water and transferred to an Amicon Ultracell 100 k centrifugal filter unit, and centrifuged at 4000 g, 4° C. for 30 minutes. NPs were washed three times with DI water to achieve a final concentration of 100 mg NP/mL DI water and snap-frozen at −80° C. until use. For drug-loaded NPs, NGI-1 was dissolved in DMSO at a concentration of 50 mg/ml, and PEI was dissolved in DMSO at 50 mg/ml. The NGI-1 and PEI solutions were then mixed at a 6:1 ratio (by weight) of PEI:drug. The solution was vortexed for ~10 seconds and then incubated at room temperature for 15 minutes. After the incubation period, the PEI/NGI-1 solution was then added to the PLA-PEG solution at a 10% ratio of NGI-1:PLA-25 PEG by weight. This combined solution was briefly vortexed and then water-bath sonicated to ensure uniform mixing. The solution was then added dropwise to DI water under vortex at a final ratio of 1:5 organic:aqueous phase. All NP preparations were tested for particle size distribution by dynamic light scattering (DLS) using a Malvern Nano-ZS (Malvern Instruments).

All experimental procedures were approved in accordance with IACUC and Yale University institutional guidelines for animal care and ethics and guidelines for the welfare and use of animals in cancer research (Workman et al., Br J Cancer, 102:1555-77 (2010)). NGI-1 delivery to glioma xenografts was evaluated using a bioluminescent imaging platform that detects inhibition of NLG (Contessa et al., Clin Cancer Res., 16:3205-14 (2010)). Ten days after subcutaneous injection of $1 \times 10^7$ gliomas cells, mice bearing palpable tumors were treated with control or NGI-1 NPs (20 mg/kg), or tunicamycin 1 mg/kg and imaged 5-30 minutes after delivery of i.p. luciferin (150 mg/kg). Signal intensity was quantified for a region of interest (ROI) encompassing each tumor and induction of bioluminscence was calculated by comparing peak bioluminescent activity from pre- and post-treatment imaging at 24 and 48 hours.

NGI-1 Therapeutic Studies in Glioma Xenografts

D54 and SKMG3 bilateral xenografts were established in nude mice by subcutaneous injection of $1 \times 10^6$ cells into hind limb. Four days after injection, mice were randomized to one of four treatment groups. They received either control or NGI-1 NPs i.v. (20 mg/kg) every other day for a total of 3 doses and either sham irradiation or a total of 10 Gy administered in daily 2 Gy fractions using a Precision X-ray 250-kV orthovoltage unit. Tumor size was measured two times per week and calculated according to the formula $\pi/6 \times (\text{large diameter}) \times (\text{small diameter})^2$.

Results

To assess the effect of NGI-1 on xenograft tumor growth, an NGI-1 nanoparticle formulation that overcomes the low solubility of this compound was used. First the effect of NGI-NPs were tested using D54-ERLucT xenografts, which increase bioluminescence after inhibition of glycoyslatio (Contessa at al., Clin Cancer Res., 16:3205-14 (2010)). A significant induction of bioluminescence in mice that received NGI-1 at both 24 (1.7 fold, p=0.03; FIG. 6A) and 48 hour (1.7 fold, p=0.03; FIG. 6A) time points was observed. Tunicmaycin, another inhibidor of N-linked glycosylation was used as a positive control and induced bioluminescence (4.2 fold at 24 hours (p=0.007)). These results confirmed the ability of NGI-1 NPs to inhibit glycosylation in D54 tumors in vivo.

Figure 6C:
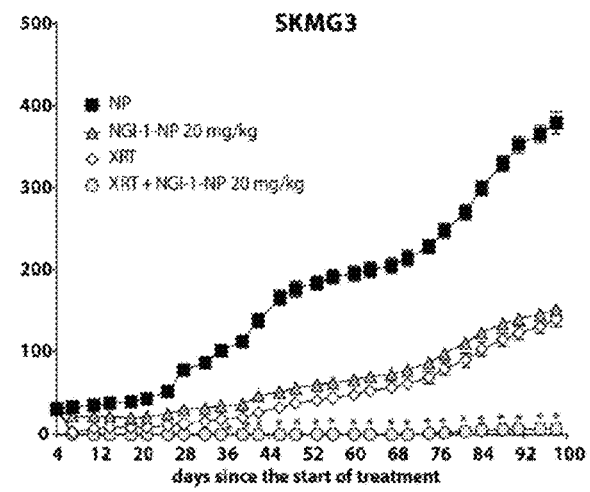

To evaluate the therapeutic potential of NGI-1 in vivo, the effect of NGI-1 NPs was tested on glioma tumor growth both alone and in combination with radiation for both D54 and SKMG3 cell lines. In these experiments mice were randomly assigned to receive treatment in one of four groups: control NPs, control NPs+RT, NGI-1NPs, and NGI-1 NPs+RT. NGI-1 NPs (20 mg/kg) were delivered every other day for a total of 3 doses and RT was delivered in 5 daily doses of 2Gy. In D54 xenografts tumor growth was significantly delayed by radiation alone or radiation+NGI-NP treatment. The addition of NGI-NPs to RT significantly reduced tumor growth compared to those treated with radiation alone. At 39 days median tumor volumes for the NGI-1 NP+RT group were 566±200 mm3 compared to 1383±305 mm3 for the RT alone group (p=0.001; FIG. 6B). Similar results favoring combined treatment with NGI-1 NPs and RT were observed in the SKMG3 xenografts. In this cell line, both radiation and NGI-NPs reduced tumor growth when administered as a single therapy. The combination of NGI-1 NPs+RT produced significantly larger reductions in tumor growth. The mean tumor volume at day 98 for the radiation+NGI-1-NP group was nearly undetectable. In comparison tumor volumes for blank NPs (379±38 mm3; p=0.001), radiation (139±27 mm3; p=0.001) and NGI-1-NP (151±7 mm3; p=0.001) were all significantly greater (FIG. 6C). For both in vivo xenograft experiments there was no evidence for significant weight loss or other toxicity in animals treated with the NGI-NP. Taken together, these results indicate that the combination of NGI-1+RT could be a therapeutic approach for the treatment of glioblastoma.

Example 7: CD8-EGFR Rescues Glioma Cells from Radiosensitization

Materials and Methods
 Generation of CD8-EGFR Cell Lines
 The CD8 cDNA was a gift from Paula Kavathas (Yale University). The CD8-EGFR was constructed according to a strategy that generated a constitutively active IGF-1R (24). The extracellular domain of CD8 was PCR amplified with a 5' XbaI and 3' SalI restriction site and cloned in-frame with the intracellular kinase domain of EGFR using the pDCB5-EGFR plasmid. SKMG3-CD8-EGFR cells were generated by Lipofectamine (Life Technologies) transfection of the plasmid followed by selection with 500 µg/ml G418. Expression of CD8-EGFR was validated by western blot analysis of the wild type and CD8-EGFR.
Results
 NGI-1 disrupts glycosylation of multiple cell surface glycoproteins, but the data indicate that the mechanism of radiosensitization is the blockade of ErbB RTK family signaling. To test this, a glycosylation-independent EGFR transgene that is resistant to the effects of NGI-1 was developed. This EGFR construct combines the extracellular domain of the CD8 protein, which contains no N-linked glycosylation sites, with the intracellular domain of the EGFR. Because CD8 spontaneously dimerizes, the CD8-EGFR produces constitutive EGFR kinase activation. To validate the construct, phospho-Y1068, phospho-Y845 and total EGFR levels were analyzed in SKMG3 parental cells and SKMG3 cells with stable expression of the CD8-EGFR. CD8-EGFR phosphorylation is insensitive to cetuximab, an antibody that recognizes the EGFR extracellular domain, but sensitive to erlotinib, a tyrosine kinase inhibitor. CD8-EGFR phosphorylation is also resistant to NGI-1, while phosphorylation of the wild type receptor continues to be significantly reduced by this inhibitor. The effects of NGI-1 on radiation clonogenic survival were examined and CD8-EGFR prevented radiosensitization of SKMG3 by NGI-1 (FIG. 7A). CD8-EGFR also eliminated the G1 cell cycle arrest caused by NGI-1 both alone and after exposure to radiation (FIG. 7B). This result coincided with no effect of NGI-1 on phospho-γH2AX foci formation in SKMG3-CD8-EGFR cells (FIG. 7C). Radiation stimulates RTK-dependent downstream signaling. AKT activation was compared in the parental SKMG3 and SKMG3-CD8-EGFR cells. The results show that NGI-1 blocks radiation-induced activation of AKT in parental but not in the CD8-EGFR expressing SKMG3 cells. This result is similar to the effect of NGI-1 on T98G cells, where NGI-1 does not block AKT activation. In summary, the CD8-EGFR model system provides additional evidence that NGI-1 radiosensitizes SKMG3 through inhibition of ErbB family RTK signaling.

RTK glycoproteins have been established as important cellular targets for modifying radiosensitivity (Begg, et al., Nat Rev Cancer, 11:239-53 (2011), Mahajan and Mahajan, Nucleic Acids Res., 43:10588-601 (2015)). However, the co-expression of multiple pro-survival cell surface receptors by a single cell or heterogeneous tumor populations complicates therapeutic strategies for blocking these signals and enhancing the effects of radiation therapy (Stommel et al., Science, 318:287-90 (2007), De Bacco et al., J Natl Cancer Inst., 103:645-61 (2011), Gouaze-Andersson et al., Cancer Res., 76:3036-44 (2016)). In Examples 2-7, the effects of a small molecule inhibitor of N-linked glycosylation (NGI-1) were tested on RTK expression and function in malignant glioma; one of the most radioresistant tumor types. NGI-1 partially reduces glycosylation of most RTKs, in some instances also affecting RTK stability, and enhances radiosensitivity of glioma cells that have upregulated ErbB family RTK signaling. NGI-1 also enhances the anti-proliferative effects of cytotoxic chemotherapy indicating that a global reduction in RTK signaling combines favorably with standard anti-tumor therapeutic approaches. Because NGI-1 is a first in class small molecule inhibitor of the OST, the data also identifies the OST as an enzyme that can be targeted to enhance standard cancer therapies. The OST is a multisubunit complex that exists in several isoforms and contains one of two individually encoded catalytic subunits; STT3A and STT3B. NGI-1 impairs the activity of the OST through a direct and reversible interaction with both catalytic subunits, but unlike tunicamycin does not cause complete inhibition of glycosylation (Lopez-Sambrooks et al., Nat Chem Biol., 12:1023-30 (2016)). Because NGI-1 does not block all glycosylation, it was believed that highly glycosylated proteins with complex secondary structure and protein folding requirements, such as the cysteine rich domains found in ErbB family RTKs Dawson at al., Structure, 15:942-54 (2007)), would be preferentially affected by this inhibitor. However, the disclosed data indicate that the effects of OST inhibition on RTK function are likely multifactorial and depend upon both the target protein that is observed, as well as the cellular context. NGI-1 disrupts EGFR localization and reduces membrane expression (Lopez-Sambrooks et al., Nat Chem Biol., 12:1023-30 (2016)). As demonstrated herein, RTK protein levels can also be affected in a cell-type specific manner. For example, NGI-1 reduces total EGFR protein levels in D54 vs SKMG3, total ErbB2 in SKMG3 vs D54, and total MET in SKMG3 and T98G vs D54 and U251. In contrast, the reduction of PDGFR and ErbB3 receptor levels appear consistent across cell lines, and surprisingly FGFR1 levels were increased (although not activated) in several cell lines. Together the data therefore indicates that both protein-intrinsic and broader cell-intrinsic factors may govern cell surface expression levels of RTKs in the setting of aberrant N-linked glycosylation. These cellular factors are likely to include both downstream transcriptional and post-translational regulation of RTK protein levels, the effect of ER stress responses, and the contributions of other cytoplasmic chaperone interactions; all of which will require further investigation. Despite differences in receptor fate, however, the consequences of aberrant N-linked glycosylation are similar for RTKs with consistent reduction of phosphorylation for individual receptors across the glioma cell lines.

Molecular studies of glioblastoma tumors have identified frequent dysregulation of growth factor receptor signaling via amplification or mutational activation of RTK genes like EGFR, ErbB2, PDGFR or MET (Cancer Genome Atlas Research N. *Nature.* 455:1061-8 (2008), Verhaak et al., *Cancer Cell,* 17:98-110 (2010)). In large scale sequencing investigations~70% of GBMs showed RTK genetic abnormalities that could potentially lead to receptor activation, with the majority involving EGFR*Brennan et al., *Cell,* 155:462-77 (2013)). In GBM patient samples and in most GBM cancer cell lines, ErbB2 protein expression has been shown to be elevated (Zhang et al., *J Natl Cancer Inst.,* 108 (2016)). Similarly, PDGFRα overexpression is associated with glioma transformation and proliferation and contributes to tumor progression and therapeutic resistance (Ozawa et al., *Cancer Cell,* 26:288-300 (2014), Lu et al., *Cancer Cell,* 29:669-83 (2016)). MET receptor overexpression and amplification has also been found in GBM and can mediate cellular reprogramming, aberrant vascularization, and chemoresistance (Joo et al., *Cancer Res.,* 72:3828-38 (2012), Huang et al., *J Clin Invest.,* 126:1801-14 (2016)). Other receptors such as FGFR, INSR, or IGF-1R have also been found to be overexpressed or activated and contribute to tumor progression in glioblastoma (Gouaze-Andersson et al., *Cancer Res.,* 76:3036-44 (2016), Almiron Bonnin et al., *Mol Cancer Ther.,* 16:705-16 (2017), Ma et al., *Clin Cancer Res.,* 22:1767-76 (2016), Singh et al., *Science,* 337:1231-5 (2012)). Therefore, the impaired function of ErbB family members, MET, and PDGFR produced by OST inhibition provides a potentially important targeted approach for disrupting multiple co-expressed and functionally redundant oncogenic RTKs in malignant glioma.

Although NGI-1 has similar effects on reducing RTK glycosylation and activation across glioma cells, radiosensitization was not observed in each cell line. An attractive explanation for this observation is the presence of mutations that are downstream from EGFR signaling. Examples include PIK3CA and PTEN, which are mutated or deleted, respectively, in ~40% of GBMs and are known to enhance survival signaling and tumor progression (Cancer Genome Atlas Research N. *Nature.* 455:1061-8 (2008), Brennan et al., *Cell,* 155:462-77 (2013)). In agreement with this, the cell lines in this study that were not radiosensitized by NGI-1 and also showed no combined effect of NGI-1 with chemotherapy (U251 and T98G) have PTEN loss. These cell lines also did not display elevated levels of ErbB family RTK activation, indicating independence from RTK signaling at multiple levels. Another route for eliminating the effect of NGI-1 on radiosensitivity is the reconstitution of glycosylation-independent RTK signaling. Because all RTKs are glycosylated, this maneuver was accomplished through the generation of a CD8-EGFR transgene, which due to the lack of N-linked glycosylation sites and spontaneous dimerization of CD8, leads to constitutive activation of the EGFR kinase domain. Expression of the CD8-EGFR in SKMG3 cells prevented radiosensitization by NGI-1, and was accompanied by a loss of NGI-1's effect on AKT signaling following radiation treatment. These results demonstrate that sustained RTK signaling is sufficient for eliminating the effect of NGI-1 on glioma radiosensitization and thus provide strong evidence that RTK inhibition is a primary mechanism for this synergistic effect. Taken together these results also imply that a subset of malignant gliomas would be sensitive to OST inhibition but that tumors with PTEN deletion, PI3K mutations, NF1 mutations, and other rare genetic alterations such as FGFR3-TACC3 fusions, may not be ideal candidates for radiosensitization with this strategy.

DNA damage induced by radiation or targeted small molecules can effectively lead to cell cycle arrest and activation of cell death programs (Sinn et al., *Mol Cancer Ther.,* 9:480-8 (2010), Cheng et al., *Clin Cancer Res.,* 19:1748-59 (2013), See et al., *Cancer Res.,* 72:3350-9 (2012)). OST inhibition by NGI-1 caused a significant increase in G1 cell cycle arrest both alone and following treatment with radiation. Although G2/M is considered the most radiosensitive phase of the cell cycle, G1 is relatively radiosensitive as well, and an arrest could contribute to the effects of NGI-1 on radiosensitivity. Notably, however, the G1 cell cycle arrest after NGI-1 treatment plus radiation was only present in cells with high levels of RTK signaling suggesting that OST inhibition causes a more potent G1 arrest, a known indicator of increased clonogenic cell death (Gupta et al., *Radiat Res.,* 145:289-98 (1996)). Follow up experiments measuring DNA damage responses using γ-H2AX foci formation demonstrated that NGI-1 treatment caused significantly more DNA damage accumulation over the first 2 hours after radiation exposure in glioma cells with high levels of RTK activation compared to those that had low levels of RTK activation. This observation is consistent with inhibition of an early RTK-dependent DNA damage response that could be mediated by a downstream pathway such as PI3K signaling. In addition, the expression of the CD8-EGFR reversed both the G1 arrest and the increase in γ-H2AX foci formation. Together these experiments indicate that disrupting the function of multiple RTKs enhances the accumulation of DNA damage and reduces clonogenic survival of glioma cells. Glioblastoma multiforme has a poor prognosis with a median survival of 12-15 months. Although several clinical trials have investigated targeted inhibition of the EGFR (Chakravarti et al., *Int J Radiat Oncol Biol Phys.,* 85:1206-11 (2013), Peereboom et al., *J Neurooncol,* 98:93-9 (2010)) or other RTKs (Chinot et al., *N Engl J Med.,* 370:709-22 (2014), Franceschi et al., *Neuro Oncol.,* 14:1503-10 (2012)) in malignant glioma, this work has not yet translated into significant advances in patient outcomes. Because N-linked glycosylation is a common biosynthetic step for RTKs identified as potential therapeutic targets in malignant glioma (eg EGFR, Met, PDGFR, and VEGFR), whether inhibition of this post-translational modification with NGI-1 is a new approach for more broadly reducing RTK dependent survival signaling was investigated. The results demonstrate that partial reduction of NLG through OST targeting with small molecules can indeed reduce parallel RTK signaling and increase tumor cell radiosensitivity for a subset of malignant gliomas.

Example 8: Lung Cancer Cell Line Screen for OST Inhibitor Sensitivity

Sambrooks, et al., "Oligosaccharyltransferase Inhibition Overcomes Therapeutic Resistance to EGFR Tyrosine Kinase Inhibitors," *Cancer Res.* 78(17):5094-5106 (2018), doi: 10.1158/0008-5472.CAN-18-0505, and all of the Supplementary Data associated therewith, is specifically incorporated by reference herein in its entirety.

The epidermal growth factor receptor (EGFR) is a transmembrane glycoprotein and receptor tyrosine kinase (RTK) that is over-expressed in diverse cancer subtypes. In NSCLC, a subset of adenocarcinomas harbor EGFR activating kinase domain mutations that drive both the initiation and maintenance of oncogenic signaling (Sordella et al., *Science*, 305(5687):1163-7 (2004), Pao et al., *Proc Natl Acad Sci USA*, 101(36):13306-11 (2004)). These tumors are sensitive to EGFR specific tyrosine kinase inhibitors (TKIs), which block EGFR signaling, induce cell death, and lead to dramatic clinical responses (Lynch et al., *N Engl J Med.*, 350(21):2129-39 (2004)).

Although TKIs have revolutionized treatment for EGFR mutant NSCLC, resistance to therapy inevitably develops and progression typically occurs within a year of treatment (Sequist et al., *J Clin Oncol.*, 26(15):2442-9 (2008), Mok et al., *N Engl J Med.*, 376(7):629-40 (2017)). Mechanisms of therapeutic resistance include secondary (T790M) and tertiary kinase domain mutations (C797S) that prevent TKI access to the kinase active site (Kwak et al., *Proc Natl Acad Sci USA*, 102(21):7665-70 (2005), Pao et al., *PLoS Med.*, 2(3):e73 (2005), Thress et al., *Nat Med.*, 21(6):560-2 (2015)). The discovery of these mutations has led to the design and synthesis of next generation EGFR TKIs that target these mechanisms of resistance and block EGFR kinase activity. However, despite significant initial clinical responses, therapeutic resistance to these EGR TKIs also occurs and leads to progressive disease.

EGFR TKI therapeutic resistance also develops through parallel, or bypass, mechanisms. These include amplification and enhanced signaling through co-expressed MET and ERBB2 RTKs, as well as in association with less well understood phenotypic changes such as acquisition of epithelial to mesenchymal transition (EMT) or small cell differentiation (Sequist et al., *Sci Transl Med.*, 3(75):75ra26 (2011), Yu et al., *Clin Cancer Res.*, 19(8):2240-7 (2013), Niederst et al., *Nat Commun.*, 6:6377 (2015)). At the genetic level co-occurring mutations to pathways that regulate membrane signaling, transcription, or control of cell cycle progression have been implicated (Blakely et al., *Nat Genet.*, 49(12):1693-704 (2017)). Because EGFR bypass resistance mechanisms can occur after initial TKI treatment, emerge later in the disease course after treatment with second or third generation inhibitors, and are difficult to treat with standard therapeutic options, they now represent a category with the greatest need for development of improved treatment strategies.

RTKs and other highly complex cell surface signaling molecules require post-translational modification by N-linked glycans to achieve appropriate cell compartment distribution, conformations, and function. N-linked glycan assembly and transfer to nascent proteins is completed in the endoplasmic reticulum by a multi-subunit protein complex called the oligosaccharyltransferase (OST). Although N-linked glycosylation is an important process, partial inhibition with NGI-1 of the OST catalytic subunit indicates a selective effect on tumor cells with RTK dependent signaling (Lopez-Sambrooks et al., *Nat Chem Biol.*, 12(12):1023-30 (2016)). Examples 8-15 examine the effects of NGI-1 on proliferation and apoptosis in EGFR mutant NSCLC with therapeutic resistance. Results indicate that targeting the OST is a viable approach for treating diverse mechanisms of resistance to EGFR TKI therapy.

Materials and Methods

Cell Line Screening

NGI-1 activity was screened in 94 lung cancer cell lines at the Center for Molecular Therapeutics at the Massachusetts General Hospital Center for Cancer Research with previously described methods (Garnett et al., *Nature*, 483 (7391):570-5 (2012)). Briefly, cells were treated in 384-well microplates using 9 serial NGI-1 dilutions, returned to an incubator for 96 hours, then stained with 55 µg/ml resazurin (Sigma) prepared in Glutathione-free media for 4 hours. Fluorescent signal intensity was quantified with a plate reader at excitation and emission wavelengths of 535/595 nm to determine viability. Viability ratio across the 9 doses were fitted to determine the half maximal inhibitory concentration (IC50). Cell lines with an IC50 less than 10 uM NGI-1 were considered sensitive to the drug. For data base comparisons, cell lines with EGFR inhibitor IC50s less than 750 nM were considered EGFR TKI sensitive.

Results

To determine cellular characteristics of OST inhibitor sensitivity, a panel of 94 lung cancer cell lines were screened and viability measured following four days of NGI-1 treatment. Fifty percent inhibitory concentration (IC50) values were determined from a nine point drug dilution series that used a maximum concentration of 10 µM, which is 10 fold higher than the $IC_{50}$ of NGI-1 in cell culture. The screening results showed that only 11/94 cell lines demonstrated an $IC_{50}$ less than 10 µM for NGI-1. These responses were compared to those from EGFR inhibitor treatments (afatinib, erlotinib, and gefitinib) performed in the same cell line screening platform (at the cancerrxgene.org website), and these results indicated a strong correlation between sensitivity to EGFR inhibition, defined as an $IC_{50}$<0.75 µM, and NGI-1 sensitivity and insensitivity (FIG. 8, Table 1). These results support the conclusion that NGI-1 preferentially affects tumor cells that are dependent on glycoprotein driven proliferation.

TABLE 1

NGI-1 sensitive lung cancer cell line identities, and drug $IC_{50}$ with notable genetic abnormalities of EGFR family receptors.

| Cell Line | Histology | NGI-1 ($IC_{50}$) | Afatinib ($IC_{50}$) | ErbB Gene Status |
|---|---|---|---|---|
| IST-SL2 | SCLC | 2.63* | 2.94# | |
| EMC-BAC-1 | NSCLC | 4.10* | .04* | ErBB3 Y523C |
| NCI-H1838 | NSCLC | 4.29* | .63* | EGFR amplified |
| PC-3 [JPC-3] | NSCLC | 4.90* | .02* | EGFR 747-749 del |
| A-427 | NSCLC | 4.92* | 5.86# | |
| RERF-LC-Sq1 | NSCLC | 7.39* | 0.15* | |
| LC-1F | NSCLC | 7.94* | 0.39*& | |
| RERF-LC-MS | NSCLC | 8.07* | 3.58# | |
| Calu-3 | NSCLC | 8.71* | 0.55* | ErbB2 amplified |
| NCI-H2110 | SCLC | 9.01* | 0.45* | |
| BEN | NSCLC | 9.72* | nt | |

Afatinib $IC_{50}$ is plotted and NGI-1 sensitive (*) or insensitive (#) cell lines are marked to show a correlation of sensitivity between the two inhibitors. "&" $IC_{50}$ for erlotinib; nt = not tested.

Using Fisher's exact test, a correlation between NGI-1 and afatinib sensitivity (73 cell lines; p<0.0001) or NGI-1 and gefitinib sensitivity (75 cell lines; p=0.0015) were significant. Only four EGFR TKI sensitive cell lines were not NGI-1 sensitive, including EGFR kinase domain mutant H3255 and LOU-NH91. NGI-1 significantly inhibits H3255 proliferation (Lopez-Sambrooks et al., *Nat Chem Biol.*, 12(12):1023-30 (2016)). Thus, these screening results are most consistent with false negative values that could be due to the growth characteristics or reduced proliferation time of the screening assay. The two other cell lines, LU-139 and EPLC-272H, were afatinib sensitive but not as responsive to other EGFR TKIs or NGI-1, which may reflect borderline TKI sensitivity. Of the seven lung cancer cell lines with sensitivity to both NGI-1 and EGFR TKIs, four harbor known genetic aberrations in the ErbB RTK family; EGFR 747-749 deletion, EGFR amplification, ErbB2 amplification, and ErbB3 Y523C mutation. In summary, the data from this screen shows that OST inhibition has a largely selective effect on lung cancer cell lines with genetic or phenotypic characteristics of EGFR and ErbB RTK driven proliferation.

Example 9: OST Inhibition Blocks Proliferation of EGFR Mutant NSCLC with T790M Mutation Materials and Methods Cell Culture and Cell Line Derivation The H1975 and A549 cell lines were purchased from ATCC (Manassas, Va.), the PC9 cell line was a gift from Katie Politi, and the HCC-827 and HCC-827-GR lines were gifts from Jeff Engelman (MGH, Boston Mass.). Cell lines were cultured in RPMI 1640+10% FBS supplemented with penicillin and streptomycin (Gibco, Life Technologies, Grand Island, N.Y., US) in a humidified incubator with 5% $CO_2$, and they were kept in culture no more than 4 months after resuscitation from the original stocks. No additional authentication was performed. *Mycoplasma* cell culture contamination was routinely checked and ruled out using the MycoAlert *Mycoplasma* Detection Kit (Lonza, Rockland, Me. USA). To generate a TKI resistant cell lines, either PC9 or H1975 cells were exposed to increasing concentrations of gefitinib or osimertinib, respectively. Gefitinib or Osimertinib concentrations were increased stepwise when cells resumed growth kinetics similar to the untreated parental cells over a dose range from 10 to 500 nM. Resistant cell cultures were obtained ~8-12 weeks after initiation of drug exposure. To confirm the emergence of a therapeutic resistant, MTT assays were performed after allowing the cells to grow in drug-free conditions for at least 4 days.

Proliferation Assays

Growth rates were determined by CellTiter 96 NonRadioactive Cell Proliferation Assay (Promega; Madison, Wis., USA) according to the manufacturer's directions. Briefly, NSCLC cells (2×103) untreated or treated with 10 μM NGI-1, 100 nM Gefitinib, or 1 μM Osimertinib (Selleck Chemicals), were seeded in triplicate in 96-wells plates and grown in culture medium containing 10% serum. The media was changed with or without new inhibitor every 48 h. Cell numbers were estimated after 0, 3, and 5 days by adding MTT (3-(4,5-dimethylthiazol-2-yl)-2,5-diphenyltetrazolium bromide) reagent to the wells 4 h before taking the spectrophotometric reading (absorbance at 570 nm).

Cell Cycle Distribution

For the assessment of cell cycle distribution, 1×106 cells were collected, washed once with ice-cold PBS and fixed in ice-cold 70% ethanol overnight at −20° C. Thereafter, cells were washed twice with PBS and incubated for 30 min at room temperature in 200 μL of Guava Cell Cycle Reagent (Guava Technologies). Cytofluorometric acquisitions were performed on a LSRII cytometer (BD Biosciences). First-line analysis was performed with Flow Jo software, upon gating of the events characterized by normal forward and side scatter parameters and discrimination of doublets in a FSC-A vs. FSC-H bivariate plot. Approximately 30,000 cells were analyzed per experiment, and the mean value was obtained from 3 independent assays.

Deep Sequencing of EGFR Mutations

Somatic mutations were identified and quantified from cell-line DNA using an enhanced version of the previously published Error-Suppressed Deep Sequencing method (Narayan et al., *Cancer Res.*, 72(14):3492-8 (2012), Goldberg et al., *Clin Cancer Res.*, 24(8):1872-80 (2018)). Genomic DNA was purified from cell lines and fragmented to an average size of ~200 bp on the Covaris E210 system. The following parameters were used for fragmentation: Duty cycle=20%, Intensity=5, Cycle per burst=200, Time=255 seconds. 10 ng of fragmented genomic DNA was used for next generation sequencing library preparation. High-throughput DNA sequencing was performed in 75 base-pair, paired-end mode on an Illumina HiSeq2500 instrument. Allelic fraction of mutant DNA was calculated based on mutant and wild-type sequence counts obtained from next-generation sequencing data.

Statistics

Data points are reported as experimental averages and error bars represent standard deviations or standard errors, as indicated, from at least three independent experiments. No samples were excluded from the analysis. The Chi-square test was used for cell line sensitivity comparisons. Otherwise statistical significance was determined using a two-sided Student's t-test with Graph-Pad Prism 6 (GraphPad Software Inc.). A P value<0.05 or less was considered to be statistically significant.

Results

The selective effect of NGI-1 on EGFR dependent lung cancer proliferation in the cell line screen led to further investigation of its effects in the setting of NSCLC TKI resistance. Gefitinib resistant cultures of the EGFR exon 19 deletion containing PC-9 cell line were generated through serial passaging in the presence of gefitinib as described in Materials and Methods. These cell lines, referred to as PC9-GR1 and PC9-GR2, were analyzed by EGFR sequencing and demonstrated to have the T790M resistance mutation. Because EGFR membrane localization and activation can be reduced through OST inhibition (Lopez-Sambrooks et al., *Nat Chem Biol.*, 12(12):1023-30 (2016)), a mechanism that is independent of the intracellular kinase domain, the effects of NGI-1 were examined on proliferation of these resistant PC9 cell lines. NGI-1 reduced the proliferation of both parental and T790M expressing PC9 cell lines by ~90% (p<0.001; FIG. 9A-9C). NGI-1 also caused a G1 arrest in both GR cell lines (60% vs 40% p<0.05 in PC9-GR1 and 80% vs 60% p<0.05 in PC9-GR2), consistent with the block in proliferation (FIG. 9D-9E). This data indicates that despite the EGFR-T790M mutation, the EGFR remains sensitive to inhibition of N-linked glycosylation.

Example 10: OST Inhibition Re-Sensitizes EGFR T790M NSCLC to EGFR TKIs

Materials and Methods

Redistribution of plasma membrane phosphatidylserine (PS) is a marker of apoptosis and was assessed by annexin V phycoerythrin (BD Biosciences) according to the manufacturer's protocol. Briefly, 1×106 cells/sample were collected, washed in PBS, pelleted, and resuspended in incubation buffer (10 mm HEPES/NaOH, pH 7.4, 140 mm NaCl, 2.5 mm $CaCl_2$) containing 1% annexin V and 1% 7-Amino-actinomycin D or propidium iodide, to identify dead cells. The samples were kept in the dark and incubated for 15 min prior to analysis by flow cytometry on a LSRII cytometer (BD Biosciences) using BD FACSDiva software (BD Biosciences). First-line analysis was performed with Flow Jo software. Approximately 50,000 cells were analyzed per experiment, and the mean value was obtained from 3 independent assays.

Clonogenic Survival Assays

Clonogenic survival assays were performed with cells treated in the presence of TKI inhibitors or NGI-1. Cultures were grown for 14 days, washed once with 1×PBS, and stained with 0.25% crystal violet in 80% methanol. Colonies with >50 cells were counted and clonogenic cell survival differences for each treatment were compared using survival curves generated from the linear quadratic equation using GraphPad Prism7 (GraphPad Software Inc.).

Western Blot Analysis

Western blot analyses were performed as previously described (Lopez-Sambrooks et al., Nat Chem Biol., 12(12): 1023-30 (2016)). Cell fractionation and recovery of cell surface proteins was performed with HCC827 and HCC827-GR cells using Qproteome Plasma Membrane Protein kit (Qiagen, Gaitherberg Md.) according the manufacturer's protocol. Immunoprecipitation of EGFR was performed on whole cell lysate of intact HCC827 and HCC827-GR cell monolayers using Protein A magnetic beads (Cell Signaling) to isolate EGFR coupled to rabbit anti-EGFR (1:100) antibody from Cell Signaling (Danvers, Mass., USA). Equilibrated Protein A magnetic beads equilibrated with a whole cell lysate were used as negative controls for non-specific protein binding. The following primary antibodies were used: rabbit anti-EGFR (1:1,000) antibody from Santa Cruz biotechnology, Inc. (Santa Cruz, Calif.); and rabbit anti-pEGFR-Y1068 (1:1,000), rabbit anti-MET (1:1,000), rabbit anti-pMET-Y1234/1235 (1:500) from Cell Signaling (Danvers, Mass., USA), anti-GADPH (HRP-60004 Proteintech; 1:10,000). The nitrocellulose-bound primary antibodies, were detected with anti-rabbit IgG horseradish peroxidase-linked antibody or anti-mouse IgG horseradish peroxidase-linked antibody (EMD Millipore; Temecula, Calif. USA), and were detected by the enhanced chemoluminescence staining ECL (GE Healthcare-Amersham Pharmacia, Buckinghamshire, U.K.). For phospho-protein array analysis, H1975 and H1975-OR cells were cultured in 6-well plates in serum-containing medium. The Human Phospho-Protein Array kit (ARY001B; R&D Systems) was used to simultaneously detect the relative level of tyrosine phosphorylation of human receptor tyrosine kinases (RTKs) according to the manufacturer's protocol.

Results

Unlike gefitinib or erlotinib, NGI-1 does not induce apoptosis in parental PC9 cells (FIG. 10A; left panel). NGI-1 treatment alone also has no pro-apoptotic effect in the PC9-GR cells. However, the combination of NGI-1 and erlotinib treatment for 48 h was sufficient to induce apoptosis in PC9-GR cell lines as measured by Annexin V flow cytometry (10% vs 40% p<0.05 FIG. 10B; right panel). The combined treatment, however, could not induce apoptosis in EGFR independent lung cancer such as the KRAS mutant A549 cells. Treatment with NGI-1 and erlotinib also produced a greater reduction of EGFR phosphorylation measured by phosphoblot analysis (and reduced clonogenic survival by more than 30% compared to treatment with either inhibitor alone (p<0.05, FIG. 10C).

The effects of NGI-1 on PC9 and PC9-GR cell proliferation can be accounted for by inhibition of EGFR glycosylation, which is invariant between the cell lines. However, a mechanism to account for NGI-1's re-sensitization of PC9 cells with EGFR T790M to erlotinib was not readily explained. The data indicates that an erlotinib sensitive target is present in the PC9 GR cell lines. To further investigate this phenomenon, deep sequencing of the PC9-GR cell lines was performed to determine proportions of the wild type, exon 19 deletion mutation, and T790M EGFR alleles (Table 2).

TABLE 2

Sequencing Details

| Cell Line | Mutations Found | Reference Sequence | Mutant Sequence | Mutant Read Count | Wild-Type Read Count | Percent Mutant |
|---|---|---|---|---|---|---|
| PC9-GR1 | EGFR Exon 19 Del | GCTTTCGGAGATGTTGCTTC (SEQ ID NO: 1) TCTTAATTCCTTGATAGC (SEQ ID NO: 2) | | 10485 | 3064 | 77.4 |
| PC9-GR1 | EGFR T790M | CTGCGTGATGAGC (SEQ ID NO: 3) | | 3432 | 31155 | 9.9 |
| PC9-GR2 | EGFR Exon 19 Del | GCTTTCGGAGATGTTGCTTC (SEQ ID NO: 4) TCTTAATTCCTTGATAGC (SEQ ID NO: 5) | | 5280 | 1599 | 76.8 |
| PC9-GR2 | EGFR T790M | CTGCGTGATGAGC (SEQ ID NO: 6) | | 1485 | 12314 | 10.8 |
| H1975 | EGRF L858R | CAGATTTTGGGCTGGCCAA (SEQ ID NO: 7) ACTGCTGGGTGCGGAAGA (SEQ ID NO: 8) | | 7241 | 12885 | 36.0 |
| H1975 | EGFR T790M | CTGCGTGATGAGC (SEQ ID NO: 9) | | 7516 | 10340 | 42.1 |
| H1975 OR | EGFR L858R | CAGATTTTGGGCTGGCCAA (SEQ ID NO: 10) ACTGCTGGGTGCGGAAGA (SEQ ID NO: 11) | | 16564 | 8759 | 65.4 |
| H1975 OR | EGRF T790M | CTGCGTGATGAGC (SEQ ID NO: 12) | | 16085 | 7952 | 66.9 |

Comparison of the number of reads for each mutation versus the number of wild type reads showed that the exon 19 deletion is found in a ratio of approximately 7:2. This ratio is consistent with amplification of the allele encoding the exon 19 deletion. In comparison, the ratio of the T790M methionine mutation to the wild type threonine sequence is approximately 1:7, showing that although it effectively confers resistance to erlotinib, this mutation is only present in a small fraction of the EGFR alleles. Sequencing data for both PC9-GR cell lines was similar indicating the outgrowth of a common resistant clone that has an allele ratio of 2:5:1 for wild type, Exon19 deletion, and exon 19 deletion/T790M EGFR. This persistence of amplified EGFR alleles with the activating exon 19 deletion mutation thus provides the explanation for a combined effect of OST inhibition with erlotinib and indicates that NGI-1 disrupts protein from the allele with T790M while erlotinib targets the other five alleles with Exon 19 deletion and no T790M resistance mutation. Together the data indicate that inhibition of EGFR-T790M glycosylation reduces EGFR phosphorylation and survival signaling and re-sensitizes EGFR mutant NSCLC to EGFR TKIs.

Example 11: OST Inhibition Re-Sensitizes EGFR Mutant NSCLC with MET Amplification to EGFR TKIs Lung cancer cells driven by RTKs other than EGFR, such as the FGFR1 dependent H1580, are sensitive to OST inhibition with NGI-1 (Lopez-Sambrooks et al., Nat Chem Biol., 12(12):1023-30 (2016)). Because therapeutic resistance to EGFR TKIs can also be mediated by other co-expressed RTKs, the effects of NGI-1 on MET amplified HCC827-GR cells (Engelman et al., Science, 316(5827): 1039-43 (2007)) was examined. Proliferation of both parental and HCC827-GR cells were sensitive to NGI-1 treatment with a reduction of proliferation by 80% (p<0.005; FIG. 11A-11B). In HCC-827-GR cells a significant G1 arrest was again observed (75% vs 45% p<0.05; FIG. 11C) similar to effects in PC9-GR cells. NGI-1 treatment was not sufficient to induce apoptosis in HCC827-GR cells, however, NGI-1 was able to re-sensitize these cells to erlotinib with significant induction of apoptosis (10% vs 50% p<0.005; FIG. 11D-11E). In agreement with these findings clonogenic survival was also decreased by more than 60% in HCC827-GR cells using both inhibitors (p<0.005 FIG. 11F). These results indicate that OST inhibitors may be able to overcome MET-mediated resistance to EGFR kinase inhibitors.

Example 12: NGI-1 Blocks EGFR and Met Co-Localization

Materials and Methods
Microscopy
For immunofluorescence, HCC827-GR cell lines were grown on glass coverslips to 80% confluence. Cell cultures were washed with PBS and fixed with 4% (w/v) formaldehyde in PBS for 30 min at 37° C. After washing with PBS, cells were permeabilized with 0.1% v/v Triton X-100 in PBS for 10 min, rinsed three times in PBS and treated with 5% w/v bovine serum albumin for 1 h. Cells were then incubated overnight at 4° C. with mouse anti-EGFR pAb (sc-03; Santa Cruz Biotechnology; 1:800) and rabbit anti-MET mAb (Cell Signaling; 1:1,000) primary antibodies and for 1 h at room temperature with either Alexa Fluor 543-conjugated goat anti-rabbit IgG or Alexa Fluor 488-conjugated goat anti-mouse IgG (ThermoFisher Scientific; 1:1,000) secondary antibodies. All antibodies were diluted in PBS containing 5% w/v bovine serum albumin. Nuclei were stained using ToPro3 (Invitrogen). Confocal cellular images were captured with an inverted Zeiss LSM 510 Pascal laser confocal microscope (Carl Zeiss, Jenna, Germany), using a 63/1.4 Plan-Apochromat objective.
Results
To elucidate a mechanism for the combined effect of NGI-1 and erlotinib in HCC827-GR cells changes in RTK phosphorylation were evaluated. MET phosphorylation was sensitive to NGI-1 in parental cells but was not affected in MET amplified HCC827-GR cells. EGFR phosphorylation, however, was significantly reduced by both NGI-1 and erlotinib in HCC827-GR cells, and eliminated by a combination of both inhibitors. The complete inhibition of EGFR phosphorylation, similar to treatment of HCC827 parental cells with erlotinib alone, provides a mechanistic explanation for increased apoptosis and reduced clonogenic survival with combined erlotinib and NGI-1 treatment. However, because MET phosphorylation was not affected these observations could not provide a clear rationale for why EGFR phosphorylation was reduced.

EGFR and MET localization after NGI-1 treatment were investigated using a cell fractionation approach. MET was only detected at the plasma membrane in the setting of MET amplification, showing the potential for increased EGFR and MET interactions in the HCC827-GR cells. NGI-1 treatment reduced EGFR and MET in the plasma membrane fraction demonstrating an effect on trafficking for both receptors. Analysis of the non-membrane fraction showed a second NGI-1 effect with inhibition of pro-MET processing to the mature receptor and elimination of mature receptor phosphorylation. In the setting of MET amplification, however, pro-MET processing and phosphorylation was increased at baseline and not blocked by NGI-1. The production of mature MET in HCC827-GR in the presence of NGI-1 provides a reasonable explanation for why NGI-1 does not reduce global MET phosphorylation. In contrast, NGI-1 reduced EGFR phosphorylation in the non-membrane fraction in both HCC827 and HCC827-GR cells.

Based on these results it was believed that decreased EGFR phosphorylation in HCC827-GR could be caused by an effect of NGI-1 on EGFR and MET receptor interactions. In support of this, immune precipitation experiments of EGFR showed reduced association with MET in both parental and GR cell lines. MET localization in HCC827-GR cells was examined using confocal microscopy with a phosphospecific MET antibody. Phosphorylated MET was detected near the cell surface in both control and NGI-1 treated samples. However, EGFR was detected near the cell surface in control HCC827-GR cells samples but not in NGI-1 treated samples, again demonstrating a dissociation of interactions between phosphorylated MET and EGFR. Together the data show that although NGI-1 does not reduce MET processing when it is over-expressed it does alter MET trafficking and also reduces EGFR and MET interactions. These results indicate that NGI-1 reduces MET dependent activation of EGFR phosphorylation by altering RTK localization in the cell.

Example 13: OST Inhibition Re-Sensitizes Osimertinib Resistant H1975 Cells to Osimertinib Third generation irreversible TKI inhibitors have been developed to successfully treat EGFR mutant NSCLC with T790M mutations. However, similar to first and second generation inhibitors, therapeutic resistance also develops. An osimertinib resistant NSCLC model was generated using the H1975 cell line, known to have both the L858R and T790M EGFR mutations. Deep sequencing of EGFR in this cell line revealed a ratio of ~4:1 for both L858R and T790M mutations compared to wild type EGFR (Table 2), indicating a T790M mutation in cis with L858R (1:1 ratio) as well as amplification of this allele. The T790M cells were then exposed to increasing concentrations of osimertinib as described in materials and methods to produce the H1975-

OR cell line. This resistant cell line was also sequenced and re-demonstrated the identical EGFR mutations as well as the absence of the C797S mutation, a known osimertinib resistance mutation. This data indicates that osimertinib resistance in H1975 cells is not mediated by genetic alterations of the EGFR.

The effects of osimertinib and NGI-1 on parental H1975 and H1975-OR cells were compared (FIG. 12A-12B). The results demonstrated that H1975 cells were sensitive and H1975-OR cells were resistant to osimertinib. However, like the previously described EGFR TKI resistant cell lines (PC9-GR, HCC827-GR), NGI-1 reduced proliferation of both parental and H1975-OR cell lines by more than 70% ($p<0.001$). Again, the block in proliferation was accompanied by a G1 arrest for both H1975 (40% vs 60% $p<0.05$) and H1975-OR cells (45% vs 75% $p<0.05$; FIG. 12C-12D). NGI-1 blocked proliferation of H1975 expressing EGFR T790M cells, similar to effects in PC9-GR cells with EGFR T790M, and consistent with the dependency of EGFR on N-linked glycosylation for cell surface expression. Combination experiments of NGI-1 plus osimertinib in H1975 cells also demonstrated re-sensitization to the TKI as measured by a significant enhancement of apoptosis (20% vs 50%, $p<0.05$, FIG. 12E-12F) and a significant reduction of clonogenic survival by greater than 80% ($p<0.0001$, FIG. 12G). The effects of NGI-1 on H1975-OR cells indicate that just as the PC9-GR and HCC827-GR cell lines achieved TKI resistance through parallel glycoprotein signaling, H1975-OR also circumvents EGFR signaling by stimulating signaling cascades that are glycoprotein dependent. Taken together this in vitro data indicate that NGI-1 treatment in combination with osimertinib can overcome therapeutic resistance to 3rd generation TKIs in EGFR-T790M expressing cells.

During the course of these studies, work detailing H1975-OR cells was published (Tang et al., *Oncotarget*, 7(49): 81598-610 (2016)). This work indicated that H1975-OR cells have reduced EGFR activation and increased ERK and AKT signaling, two major downstream proteins of the EGFR pathway. This finding is similar to the H1975 resistant cell line, indicating isolation of a similar H1975 resistant clone. Notably Tang et. al. could not identify a discrete resistance mechanism and the RTK phospho-array screen did not show up-regulation of receptor activation, and thus it is believed that osimertinib therapeutic resistance could be regulated by individual or groups of glycoproteins in this cell line.

Example 14: Formulation and Imaging of NGI-1 Nanoparticle Activity In Vivo

Materials and Methods

NGI-1 Nanoparticle (NP) Preparation

Polyethylene glycol (PEG)-b-Polylactic acid (PLA) diblock polymer (Mw PEG=5 kDa, Mw PLA=10 kDa) was purchased from Polysciences, Inc. (Warrington, Pa., USA). Dimethylsulfoxide were obtained from J. T. Baker (Avantor Performance Materials, Central Valley, Pa., USA). Polyethyleneimine (PEI; branched—average Mw~800, average Mn~600) was purchased from Sigma-Aldrich (USA). PLA-PEG NPs were synthesized using a nanoprecipitation technique, similar to one previously reported (17). Briefly, to create control NPs, 100 mg of polymer was dissolved in 5 ml DMSO at RT for 2 h. The polymer solution was then divided into 200 µL aliquots. Each 200 µL aliquot was added drop-wise to 1 mL deionized (DI) water under strong vortex to create a NP suspension. These suspensions were immediately pooled and diluted 5× with DI water. This diluted suspension was then transferred to an Amicon Ultracell 100 k centrifugal filter unit, and centrifuged at 4000 g, 4° C. for 30 min. The NPs were washed twice with DI water and centrifuged for another 30 min each time. After a final wash with DI water, the NPs were then centrifuged for 1 h to achieve a final concentration of 100 mg NP/mL DI water. The final NP suspension was then either immediately used for in vivo or in vitro experiments, or snap-frozen at −80° C. until use.

For drug-loaded NPs, NGI-1 was dissolved in DMSO at a concentration of 50 mg/ml, and PEI was dissolved in DMSO at 50 mg/ml. The NGI-1 and PEI solutions were then mixed at a 6:1 ratio (by weight) of PEI:drug. The solution was vortexed for ~10 s and then incubated at room temperature for 15 min. After the 15 min incubation period, the PEI/NG-1 solution was then added to the PLA-PEG solution at a 10% ratio of NGI-1:PLA-PEG by weight. This combined solution was briefly vortexed and then water-bath sonicated to ensure uniform mixing. The solution was then added dropwise to diH2O under vortex at a final ratio of 1:5 organic:aqueous phase. These suspensions were then pooled, diluted, and filtered, washed, and frozen and stored or used as above. For PEI-only loaded control NPs, PEI was dissolved in DMSO at a concentration of 50 mg/ml, the PEI solution was then added to the PLA-PEG solution at a 60% ratio of PEI:PLA-PEG by weight. This combined solution was briefly vortexed and then water-bath sonicated to ensure uniform mixing. The solution was then added dropwise to diH2O under vortex at a final ratio of 1:5 organic:aqueous phase. These suspensions were then pooled, diluted, and filtered, washed, and frozen and stored or used as above. All NP preparations were tested for particle size distribution by dynamic light scattering (DLS) using a Malvern Nano-ZS (Malvern Instruments).

To assess particle loading a 100 µL solution of a nanoparticle sample was lyophilized in a pre-weighed eppendorf tube to measure particle yield. Drug loading was determined by dissolving 10 mg of NPs in 1 ml of acetonitrile (ACN) for 24 h at RT. The dissolved NP solution was then size-filtered at 0.22 µM and the filtrate was analyzed using a Shimadzu HPLC System (SpectraLab Scientific, Markham, ON, Canada) and compared against a previously established standard curve for NGI-1. Drug loading was repeated with three technical replicates per batch of NPs.

NGI-1 Imaging In Vivo

Bioluminescent imaging of mice bearing PC9 ERlucT flank tumors were generated as previously described (18). Tumors were grown in six week old female athymic Swiss nu/nu mice (Envigo) by subcutaneous flank implantation of ~1×107 cells into the hind limb. Ten days following injection, mice bearing palpable tumors were anesthetized with a 1% isoflurane/air mixture and given a single I.P. dose of 150 mg/kg luciferin in normal saline. Bioluminescent imaging was performed from 5 to 30 minutes after luciferin administration, and mice were anesthetized and kept warm with a temperature controlled bed during image acquisition. Signal intensity was quantified for a region of interest (ROI) for each tumor over the imaging time period to determine the peak of bioluminescent activity. Tumor bioluminescence prior to drug treatment was used to establish a baseline of activity and to calculate induction of Luc activity. After obtaining baseline images, mice were treated i.v. with blank nanoparticles or 20 mg/Kg of NGI-1 nanoparticles. Tumor bioluminescence was assessed at day 1 and day 2 after treatment. All experimental procedures were approved in accordance with IACUC and Yale university institutional guidelines for animal care and ethics and guidelines for the welfare and use of animals in cancer research.

Results

NGI-1 is a drug-like compound with favorable physicochemical properties; however, solubility remains a significant challenge for in vivo translation of this inhibitor. To test the hypothesis that NGI-1 could enhance TKI therapy in EGFR mutant and TKI resistant NSCLC, a NGI-1 nanoparticle (NGI-NP) formulation was developed by nanoprecipitation of a NGI-1 PEI complex. All nanoparticle preparations were confirmed by DLS and the average particle size was 120±10 nm. To assess the activity of the NGI-1 NPs a PC9 cell line with stable expression of the ER-LucT glycosylation reporter (Contessa at al., *Clin Cancer Res.*, 16(12): 3205-14 (2010)), a luciferase engineered to be expressed in the endoplasmic reticulum with N-linked glycosylation sites, was established. Under normal cell conditions glycosylation of the luciferase blocks activity and luminescence. However, under conditions of decreased glycosylation luciferase activity is restored with a measurable increase in luciferase activity. Equivalent concentrations of NGI-1, either dissolved in DMSO or via NP, activated luminescence~6 fold after 24 h in these PC9-ERLucT cells in vitro (FIG. 13A).

To test whether intravenous delivery of NGI-1-NP could alter N-linked glycosylation in vivo, serial bioluminescent imaging of PC9-ERLucT xenograft tumors was performed. Luminescence was quantified to estimate the magnitude and duration of NLG inhibition after a single i.v. injection of either NGI-1-NP (20 mg/Kg) or blank NPs. The results demonstrated a significant induction of bioluminescence at 24 hours in mice that received NGI-1 NPs (1.5 fold, p=0.04; FIG. 13B), and 2.0 fold enhancement at 48 h (p=0.01). This data confirmed the efficacy of the NGI-1 when administered as a NP formulation and indicated that daily treatment was not necessary to achieve sustained OST inhibition.

Example 15: NGI-1 Reduces Growth of EGFR Mutant, TKI-Resistant NSCLC In Vivo

Materials and Methods

NGI-1 Therapeutic Studies in Xenograft Tumors

The effects of NGI-1 were evaluated in Six-to-eight-week old female athymic Swiss nu/nu mice bearing bilateral flank xenograft tumors. Five days after inoculation, mice were randomized to receive i.v. NGI-1 NPs (20 mg/kg) or blank NPs three times per week for a total of 8 doses. TKI inhibitors (erlotinib or osimertinib) were orally administered every day at a dose of 25 mg/kg and 5 mg/kg, respectively, over the same time period as NGI-1 treatment. Tumor size was measured three times per week and volume was calculated according to the formula $\pi/6 \times (length) \times (width)^2$.

Results

To evaluate the potential therapeutic effects of NGI-1 in vivo, NGI-1 was tested both alone and in combination with EGFR TKIs on tumor growth using both HCC827-GR and H1975-OR cell lines. These TKI resistance models were chosen because EGFR mutant, TKI resistant NSCLC that is not driven by an EGFR T790M allele remains the major clinical challenge in this patient population. For both HCC827-GR and H1975-OR xenografts, growing tumors were randomly assigned to receive NGI-NP or EGFR-TKI as either a monotherapy or in combination. HCC827-GR-xenografts were treated with control NPs, 25 mg/kg erlotinib, 5 mg/kg NGI-NP, or erlotinib+NGI-1-NP. Similar to in vitro findings, the combination of erlotinib and NGI-1 had the greatest impact on tumor growth. The mean tumor volume of erlotinib+NGI-NP at day 25 was 380±121 mm$^3$, significantly less than mice that received erlotinib (829±149 mm$^3$; p=0.001) or NGI-1-NP (940±283 mm$^3$; p=0.001) alone (FIG. 13C). Similar results favoring the combined treatment were observed in the H1975-OR xenografts. In this resistant line, the combination of osimertinib and NGI-NP caused a comparatively larger reduction in tumor growth. The mean tumor volume at day 78 for the osimertinib+NGI-1-NP group was 68±117 mm$^3$. In comparison tumor volumes for blank NPs (926±253 mm3; p=0.001), 5 mg/kg osimertinib (584±296 mm$^3$; p=0.001) and 5 mg/kg NGI-1-NP (531±142 mm$^3$; p=0.001) were significantly greater (FIG. 7D). In this xenograft model, the combined therapy group caused an ~50 day delay in tumor growth. For both in vivo experiments, there was no evidence of toxicity or significant weight loss in animals treated with NGI-NP. Taken together, these results indicate that the combination of an EGFR TKI with NGI-1 provides a potential therapeutic approach for NSCLC with resistance to EGFR inhibitors.

The emergence of therapeutic resistance to EGFR TKIs prevents long term disease control and a cure for patients with EGFR mutant NSCLC. Tumor cell adaptation to EGFR targeted therapy is a familiar pattern that has been observed for 1st, 2nd, and 3rd generation inhibitors (Lee et al., *Ann Oncol.*, 24(8):2080-7 (2013), Chong et al., *Nat Med.*, 19(11): 1389-400 (2013)) and arises from both selection of existing tumor cell clones or from spontaneous acquisition of mechanisms for therapeutic resistance (Hata et al., *Nat Med.*, 22(3):262-9 (2016)). Similar to the clinical observations from other disease sites employing TKIs, recurrent kinase domain mutations (i.e., T790M or C797S) that eliminate EGFR TKI action are a major form of therapeutic resistance that can be further targeted through structure based modeling and the ingenuity of medicinal chemistry. However, a significant portion of the EGFR TKI resistant population initially develops bypass mechanisms, which are not responsive to EGFR targeting, and ultimately even tumors with kinase domain resistance mutations will also undergo progression through an EGFR kinase insensitive mechanism. Example 8-15 demonstrate that a small molecule inhibitor of the OST can overcome EGFR TKI therapeutic resistance, both in settings of EGFR dependent and independent resistance, and identify inhibition of N-linked glycosylation as a strategy for treating EGFR mutant NSCLC.

The EGFR is a highly glycosylated protein with 11 canonical N-linked glycosylation sequons (NXS/T) and one non-canonical NXC site (Ullrich et al., *Nature*, 309(5967): 418-25 (1984)). Either complete or partial inhibition of this post-translational modification alters the receptor's stability, localization, and function (Lopez-Sambrooks et al., *Nat Chem Biol.*, 12(12):1023-30 (2016), Contessa et al., *Cancer Res.*, 68(10):3803-9 (2008), Tsuda et al., *J Biol Chem.*, 275(29):21988-94 (2000)) indicating that blocking N-linked glycosylation is an approach for reducing EGFR driven signaling. Recently an OST inhibitor was described that targets the catalytic subunit and causes partial inhibition of N-linked glycosylation, an effect that is consistent with an allosteric mechanism of action. Examples 8-15 demonstrate that a kinase domain mutant EGFR, with or without the T790M mutation, is sensitive to partial inhibition of N-linked glycosylation by pharmacologic inhibition of the OST. The data confirms the belief that glycosylation of the extracellular domain is a key regulator of receptor function that remains crucial in the setting of kinase domain resistance mutations. Inhibition of glycosylation thus has advantages of providing a kinase domain independent mechanism for EGFR inhibition, which couples favorably with kinase domain targeting, as well as the potential for targeting other RTKs and glycoproteins that contribute to tumor cell survival signaling.

Investigation into the synergistic effects of NGI-1 and EGFR TKIs also provided new insights into the cellular mechanism of EGFR TKI resistance. In the PC9-GR cell line the combined effect of NGI-1 plus erlotinib led to the observation that a minority of alleles harboring the T790M mutation can drive TKI resistance. This data has implications for TKI therapy where the affinity of TKIs may vary for Exon 19 deletions, L858R point mutations, and T790M resistance mutations. For example, the acquisition of a C797S mutation on a single allele could drive 3rd generation TKI resistance and be sensitive to 4th generation EGFR TKIs, yet EGFR alleles with only an exon 19 deletion would be insensitive to this new class of allosteric inhibitors (Jia et al., Nature, 534(7605):129-32 (2016)). The results investigating TKI resistance in the setting of MET amplification also provided insights into bypass mechanism of resistance. Although reduction of MET glycosylation reduces MET phosphorylation in the HCC827 cell line, a significant effect in the MET amplified HCC827-GR cell line was not seen. In this model of TKI resistance, interference of EGFR and MET interactions was associated with reduced EGFR phosphorylation. This indicates changes in RTK trafficking and localization may also be important for establishing a TKI resistant phenotype. The inability of NGI-1 to block MET activation or processing of the pro-receptor to the mature form in the setting of MET amplification is itself of interest as EGFR overexpression and amplification does not cause insensitivity to NGI-1. This difference between MET and EGFGR reflects distinct requirements for receptor processing and maturation in the secretory pathway and indicates that EGFR may be more sensitive to inhibition of N-linked glycosylation by NGI-1 than other RTKs.

EGFR TKI therapeutic resistance (including the EGFR T790M mutation) is largely characterized by bypass mechanisms initiated by plasma membrane receptors. Although downstream mutations of the Ras/MAPK pathway have been described (de Mello et al., World J Clin Oncol., 2(11):367-76 (2011), Pao et al., PLoS Med., 2(1):e17 (2005)), whether tumor cells become absolutely dependent on these mutations for proliferation and survival remains unclear. On the genetic level, in addition to MET, mutations or amplification of ErbB2 have also been observed after EGFR TKI resistance develops (Landi and Cappuzzo, Expert Rev Anticancer Ther., 13(10):1219-28 (2013)). AXL and IGF-1R are additional glycoproteins implicated in TKI resistance through initiation of parallel and compensatory survival signaling (Vazquez-Martin et al., Sci Rep., 3:2560 (2013), Byers et al., Clin Cancer Res., 19(1):279-90 (2013)), and it has been demonstrated that RTK stimulation by growth factors rescues EGFR dependent NSCLC cell lines from TKI therapy (Yoshida et al., Clin Cancer Res., 20(15): 4059-74 (2014), Wilson et al., Nature, 487(7408):505-9 (2012)). The analysis of clinical and cell culture samples has also implicated epithelial to mesenchymal transition as a cellular maneuver to evade drug toxicity. CRIPTO1, NRP2, and TGFB have all been identified as factors that induce EMT and cause EGFR TKI resistance (Park et al., J Clin Invest., 124(7):3003-15 (2014), Gemmill et al., Sci Signal, 10(462) (2017), Yao et al., Proc Natl Acad Sci USA, 107 (35):15535-40 (2010)). Even more recently β-adrenergic signaling and 11-6 signaling have been demonstrated to mediate therapeutic resistance in EGFR mutant NSCLC (Nilsson et al., Sci Transl Med., 9(415) (2017)). Together these mechanisms of resistance can be practically classified with respect to the proteins involved, and thus the majority of EGFR TKI resistance can be ascribed to preservation of and dependence on cell surface glycoprotein signaling. In this context, the discovery of NGI-1 and demonstration of therapeutic effect is noteworthy as it indicates that OST inhibition may be effective against diverse resistance mechanisms.

On the cellular level, EGFR TKI resistance manifests itself with cell cycle progression, proliferation, and tumor growth. Although EGFR inhibition typically induces a cell cycle arrest in the G1 phase followed by apoptosis (Song et al., Cancer Res., 66(11):5542-8 (2006), Helfrich et al., Clin Cancer Res., 12(23):7117-25 (2006), de La Motte Rouge et al., Cancer Res., 67(13):6253-62 (2007)), bypass mechanisms either uncouple or replace EGFR dependent progression through cell cycle checkpoints. The importance of dysregulated cell cycle check points as a mechanism of EGFR TKI therapeutic resistance has recently been emphasized by a large genomic analysis of serial patient samples where co-occurring mutations or copy number variations of cell cycle regulatory genes (eg CDK4 and CDK6), were a important indicators of progression free survival (Blakely et al., Nat Genet., 49(12):1693-704 (2017)). The ability of NGI-1 to induce G1 arrest in EGFR TKI resistant cells is therefore likely to be a fundamental consequence of the inhibitor, and when coupled with EGFR kinase inhibition, leads to restoration of an apoptotic response and cell death.

Targeting the OST and disrupting N-linked glycosylation in eukaryotic cells is anticipated to affect multiple downstream glycoprotein targets. Until now, and with the discovery a partial inhibitor of N-linked glycosylation, blockade of this post-translational modification has not been investigated due to anticipated toxicity. Indeed tunicamycin, which blocks the first committed step in glycan precursor biosynthesis and all N-linked glycosylation has significant toxicity both in vitro and in vivo (Contessa at al., Clin Cancer Res., 16(12):3205-14 (2010)). NGI-1 on the other hand was identified in a cell based phenotypic HTS that inherently selected against small molecules which induce cell death. The results disclosed herein demonstrate a relatively selective effect on proliferation for EGFR and ErbB family receptor driven lung cancer through the profiling of 94 lung cancer cell lines. Specificity for RTK (and other glycoprotein) driven proliferation is also consistent with observations of no significant toxicity in non-transformed cell lines, primary human dermal fibroblasts, and neural progenitor cells (Lopez-Sambrooks et al., Nat Chem Biol., 12(12): 1023-30 (2016), Hafirassou et al., Cell Rep., 21(13):3900-13 (2017), Puschnik et al., Cell Rep., 21(11):3032-39 (2017)). The in vivo pharmacokinetic challenges of NGI-1 were overcome using a nanoparticle formulation to effectively deliver the drug to the tumor by intravenous injection. The re-sensitization of TKI resistant HCC827-GR and H1975-OR to EGFR TKIs without significant side effects thus shows for the first time that targeting N-linked glycosylation is feasible in vivo.

In summary, a small molecule inhibitor of the OST partially inhibits N-linked glycosylation and re-sensitizes EGFR mutant NSCLC to EGFR TKIs. Targeting N-linked glycosylation has the advantage of disrupting the dependence of NSCLC tumor cells on cell surface receptor signaling and couples well with EGFR TKIs to produce blockade of both primary and redundant mechanism of cell growth. Demonstration of significant tumor growth delay with little toxicity provides a strong rationale for use of this targeted approach for reducing oncogenic signaling in NSCLC.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. Particles for delivery of one or more small molecule, non-polymeric therapeutic, prophylactic or diagnostic agents comprising
    a) a core comprising a complex formed by the ionic association of the one or more small molecule, non-polymeric therapeutic, prophylactic, or diagnostic agents and one or more polycationic polymers, and
    b) an outer layer comprising one or more amphiphilic block copolymers non-covalently associated on the outside of the complex.

2. The particles of claim 1, wherein the complex forms nanoparticles having an average diameter of between 5 and 500 nm, inclusive.

3. The particles of claim 2, wherein the nanoparticles have a diameter of between 20 nm and about 500 nm, between about 25 nm and about 250 nm, between about 25 nm and about 150 nm, between about 50 nm and about 150 nm, or between about 50 nm and about 100 nm.

4. The particles of claim 1, wherein at least one of the one or more amphiphilic block copolymers is a polyester-polyalkylene oxide block polymer.

5. The particles of claim 4, wherein the polyester-polyalkylene oxide block polymer is a poly(D,L-lactide)-poly(ethylene glycol) diblock polymer.

6. The particles of claim 1, wherein at least one of the one or more polycationic polymers is polyethyleneimine.

7. The particles of claim 1, wherein at least one of the one or more polycationic polymers has a molecular weight between about 5,000 Daltons and about 50,000 Daltons.

8. The particles of claim 1, wherein the one or more small molecule, non-polymeric therapeutic agents are selected from the group consisting of chemotherapeutic agents, anti-angiogenesis agents, immunomodulators, and antiinfectives.

9. The particles of claim 1, wherein at least one of the one or more small molecule, non-polymeric therapeutic agents directly or indirectly reduces or inhibits N-glycosylation of one or more receptor tyrosine kinases, by about 10%, 20%, 30%, 40%, 50%, 60%, 70%, 80%, 90%, or more than 90%.

10. The particles of claim 9, wherein at least one of the one or more receptor tyrosine kinases is one or more EGFR family members, FGFR family members, or combinations thereof.

11. The particles of claim 1, wherein at least one of the one or more small molecule, non-polymeric therapeutic agents is an inhibitor of oligosaccharyltransferase.

12. The particles of claim 1, wherein at least one of the one or more small molecule, non-polymeric therapeutic agents is a compound of Formula I:

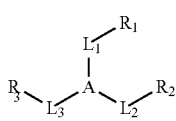

Formula I wherein,
A is unsubstituted aryl, substituted aryl, unsubstituted polyaryl, substituted polyaryl, substituted heteroaryl, unsubstituted heteroaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl;

$L_1$ and $L_3$ are independently, —$SO_2$—, —NHC(O)—, —$NR^{a'}$C(O)—, —C(O)NH—, —C(O)$NR^{a'}$—, —C(O)O—, —OC(O)—, —C(O)—, —C(O)OCH$_2$—, —$SO_2NR^{a'}$—, —CH$_2R^{a'}$—, —O—, —$NR^{a'}$H—, —$NR^{a'}$—, —OCONH—, —NHCOO—, —OCON$R^{a'}$—, —$NR^{a'}$COO—, —NHCONH—, —$NR^{a'}$CONH—, —NHCON$R^{a'}$—, —$NR^{a'}$CON$R^{a''}$—, —CHOH—, —C$R^{a'}$OH—, unsubstituted alkyl, substituted alkyl, substituted alkylene, substituted alkenyl, unsubstituted alkenyl, substituted alkylamino, unsubstituted alkylamino, substituted carbonyl, or unsubstituted carbonyl;

$L_2$ is absent, —$SO_2$—, —NHC(O)—, —$NR^{a'}$C(O)—, —C(O)NH—, —C(O)$NR^{a'}$—, —C(O)O—, —OC(O)—, —C(O)—, —C(O)OCH$_2$—, —$SO_2NR^{a'}$—, —CH$_2R^{a'}$—, —O—, —$NR^{a'}$H—, —$NR^{a'}$—, —OCONH—, —NHCOO—, —OCON$R^{a'}$—, —$NR^{a'}$COO—, —NHCONH—, —$NR^{a'}$CONH—, —NHCON$R^{a'}$—, —$NR^{a'}$CON$R^{a''}$—, —CHOH—, —C$R^{a'}$OH—, unsubstituted alkyl, substituted alkyl, substituted alkylene, substituted alkenyl, unsubstituted alkenyl, substituted alkylamino, unsubstituted alkylamino, substituted carbonyl, or unsubstituted carbonyl;

$R^{a'}$ and $R^{a''}$ are hydrogen, halogen, hydroxyl, unsubstituted alkyl, substituted alkyl, substituted alkylene, unsubstituted alkylene, substituted alkenyl, unsubstituted alkenyl, substituted alkylamino, unsubstituted alkylamino, substituted carbonyl, or unsubstituted carbonyl, an aryl group, or a heterocyclic group;

$R_1$ is unsubstituted dialkylamine, substituted dialkylamine, substituted $C_3$-$C_{20}$ heterocyclyl, unsubstituted $C_3$-$C_{20}$ heterocyclyl, substituted N-aryl-N-alkylamine, unsubstituted N-aryl-N-alkylamine, substituted aralkylamine, or unsubstituted aralkylamine;

$R_2$ is hydrogen, substituted $C_3$-$C_{20}$ heterocyclyl, unsubstituted $C_3$-$C_{20}$ heterocyclyl, substituted $C_3$-$C_{20}$ cycloalkyl, unsubstituted $C_3$-$C_{20}$ cycloalkyl, substituted dialkylamine, or unsubstituted dialkylamine; and $R_3$ is substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, or unsubstituted $C_3$-$C_{20}$ heterocyclyl.

13. The particles of claim 1, wherein at least one of the one or more small molecule, non-polymeric therapeutic agents is 5-(dimethylsulfamoyl)-N-(5-methyl-1,3-thiazol-2-yl)-2-(pyrrolidin-1-yl)benzamide.

14. A method of delivering one or more small molecule, non-polymeric therapeutic, prophylactic or diagnostic agents to a subject comprising administering a pharmaceutical composition comprising the particles of claim 1 to the subject.

15. The method of claim 14, wherein at least one of the one or more small molecule, non-polymeric therapeutic agents is a compound of Formula I:

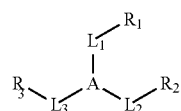

Formula I wherein,

A is unsubstituted aryl, substituted aryl, unsubstituted polyaryl, substituted polyaryl, substituted heteroaryl, unsubstituted heteroaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, unsubstituted $C_3$-$C_{20}$ heterocyclyl, substituted $C_3$-$C_{20}$ cycloalkenyl, unsubstituted $C_3$-$C_{20}$ cycloalkenyl, substituted $C_3$-$C_{20}$ cycloalkynyl, or unsubstituted $C_3$-$C_{20}$ cycloalkynyl;

$L_1$ and $L_3$ are independently, —$SO_2$—, —NHC(O)—, —$NR^{a'}$C(O)—, —C(O)NH—, —C(O)$NR^{a'}$—, —C(O)O—, —OC(O)—, —C(O)—, —C(O)$OCH_2$—, —$SO_2NR^{a'}$—, —$CH_2R^{a'}$—, —O—, —$NR^{a'}$H—, —$NR^{a'}$—, —OCONH—, —NHCOO—, —OCON$R^{a'}$—, —$NR^{a'}$COO—, —NHCONH—, —$NR^{a'}$CONH—, —NHCON$R^{a'}$—, —$NR^{a'}$CON $R^{a''}$—, —CHOH—, —C $R^{a'}$OH—, unsubstituted alkyl, substituted alkyl, substituted alkylene, substituted alkenyl, unsubstituted alkenyl, substituted alkylamino, unsubstituted alkylamino, substituted carbonyl, or unsubstituted carbonyl;

$L_2$ is absent, —$SO_2$—, —NHC(O)—, —$NR^{a'}$C(O)—, —C(O)NH—, —C(O)$NR^{a'}$—, —C(O)O—, —OC(O)—, —C(O)—, —C(O)$OCH_2$—, —$SO_2NR^{a'}$—, —$CH_2R^{a'}$—, —O—, —$NR^{a'}$H—, —$NR^{a'}$—, —OCONH—, —NHCOO—, —OCON$R^{a'}$—, —$NR^{a'}$COO—, —NHCONH—, —$NR^{a'}$CONH—, —NHCON$R^{a'}$—, —$NR^{a'}$CON $R^{a''}$—, —CHOH—, —C $R^{a'}$OH—, unsubstituted alkyl, substituted alkyl, substituted alkylene, substituted alkenyl, unsubstituted alkenyl, substituted alkylamino, unsubstituted alkylamino, substituted carbonyl, or unsubstituted carbonyl; $R^{a'}$ and $R^{a'''}$ are hydrogen, halogen, hydroxyl, unsubstituted alkyl, substituted alkyl, substituted alkylene, unsubstituted alkylene, substituted alkenyl, unsubstituted alkenyl, substituted alkylamino, unsubstituted alkylamino, substituted carbonyl, or unsubstituted carbonyl, an aryl group, or a heterocyclic group;

wherein $R^{a'}$ and $R^{a'''}$ are hydrogen, halogen, hydroxyl, unsubstituted alkyl, substituted alkyl, substituted alkylene, unsubstituted alkylene, substituted alkenyl, unsubstituted alkenyl, substituted alkylamino, unsubstituted alkylamino, substituted carbonyl, or unsubstituted carbonyl, an aryl group, or a heterocyclic group;

$R_1$ is unsubstituted dialkylamine, substituted dialkylamine, substituted $C_3$-$C_{20}$ heterocyclyl, unsubstituted $C_3$-$C_{20}$ heterocyclyl, substituted N-aryl-N-alkylamine, unsubstituted N-aryl-N-alkylamine, substituted aralkylamine, or unsubstituted aralkylamine;

$R_2$ is hydrogen, substituted $C_3$-$C_{20}$ heterocyclyl, unsubstituted $C_3$-$C_{20}$ heterocyclyl, substituted $C_3$-$C_{20}$ cycloalkyl, unsubstituted $C_3$-$C_{20}$ cycloalkyl, substituted dialkylamine, or unsubstituted dialkylamine; and $R_3$ is substituted heteroaryl, unsubstituted heteroaryl, substituted aryl, unsubstituted aryl, unsubstituted polyaryl, substituted polyaryl, substituted polyheteroaryl, unsubstituted polyheteroaryl, substituted $C_3$-$C_{20}$ cycloalkyl, unsubstituted $C_3$-$C_{20}$ cycloalkyl, substituted $C_3$-$C_{20}$ heterocyclyl, or unsubstituted $C_3$-$C_{20}$ heterocyclyl.

16. The method of claim 15, wherein the subject has cancer.

17. The method of claim 16, where in the cancer is non-small-cell lung cancer or glioma.

18. The method of claim 17, wherein the pharmaceutical composition is administered in combination with a chemotherapeutic agent, radiotherapy, or a combination thereof.

19. The method of claim 18, where in the cancer is associated with one or more mutations in one or more receptor tyrosine kinases.

20. Particles for delivery of one or more therapeutic agents comprising
  a) a core comprising a complex formed by the ionic association of the one or more therapeutic agents and one or more polycationic polymers, and
  b) an outer layer comprising one or more amphiphilic block copolymers non-covalently associated on the outside of the complex,
  wherein the one or more therapeutic agents reduce or inhibit N-glycosylation.

21. The particles of claim 20, wherein the one or more therapeutic agents are selected from the group consisting of proteins, peptides, sugars, lipids, nucleic acids, or small molecules.

22. Particles for delivery of one or more therapeutic agents comprising
  a) a core comprising a complex formed by the ionic association of the one or more therapeutic agents and one or more polycationic polymers, and
  b) an outer layer comprising one or more amphiphilic block copolymers non-covalently associated on the outside of the complex,
  wherein the one or more therapeutic agents are selected from the group consisting of proteins, peptides, sugars, lipids, nucleic acids, or small molecules, and
  wherein the one or more therapeutic agents reduce N-glycosylation of one or more receptor tyrosine kinases by about 10%, 20%, 30%, 40%, 50%, 60%, 70%, 80%, 90%, or more than 90%.

* * * * *

```
                           SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 1
gctttcggag atgttgcttc                                                  20

<210> SEQ ID NO 2
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 2
tcttaattcc ttgatagc                                                    18

<210> SEQ ID NO 3
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 3
ctgcgtgatg agc                                                         13

<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4
gctttcggag atgttgcttc                                                  20

<210> SEQ ID NO 5
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 5
tcttaattcc ttgatagc                                                    18

<210> SEQ ID NO 6
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 6
```

-continued ctgcgtgatg agc                                                      13

<210> SEQ ID NO 7
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 7
cagattttgg gctggccaa                                                19

<210> SEQ ID NO 8
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 8
actgctgggt gcggaaga                                                 18

<210> SEQ ID NO 9
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 9
ctgcgtgatg agc                                                      13

<210> SEQ ID NO 10
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 10
cagattttgg gctggccaa                                                19

<210> SEQ ID NO 11
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 11
actgctgggt gcggaaga                                                 18

<210> SEQ ID NO 12
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 12
ctgcgtgatg agc                                                      13